(12) United States Patent
Brown et al.

(10) Patent No.: US 9,127,005 B2
(45) Date of Patent: Sep. 8, 2015

(54) ISOFORM SELECTIVE PHOSPHOLIPASE D INHIBITORS

(75) Inventors: H. Alex Brown, Franklin, TN (US); Craig W. Lindsley, Brentwood, TN (US); Alex G. Waterson, Murfreesboro, TN (US); Sarah A. Scott, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 573 days.

(21) Appl. No.: 13/386,397

(22) PCT Filed: Jul. 23, 2010

(86) PCT No.: PCT/US2010/043045
§ 371 (c)(1),
(2), (4) Date: May 1, 2012

(87) PCT Pub. No.: WO2011/011680
PCT Pub. Date: Jan. 27, 2011

(65) Prior Publication Data
US 2012/0214832 A1    Aug. 23, 2012

Related U.S. Application Data

(60) Provisional application No. 61/228,492, filed on Jul. 24, 2009.

(51) Int. Cl.
*A61K 31/438* (2006.01)
*C07D 471/10* (2006.01)
(52) U.S. Cl.
CPC ..................................... *C07D 471/10* (2013.01)
(58) Field of Classification Search
CPC ...................................................... C07D 471/10
USPC .......................................................... 514/278
See application file for complete search history.

(56) References Cited

U.S. PATENT DOCUMENTS 6,187,559 B1    2/2001    Steed et al. ................... 435/69.1
8,263,608 B2    9/2012    Shi et al. ........................ 514/278
(Continued)

FOREIGN PATENT DOCUMENTS

AU    2010275526    2/2012
BR    112012001586.9    3/2012
(Continued)

OTHER PUBLICATIONS

Communication Pursuant to Rules 161(2) and 162 EPC issued Mar. 20, 2012 for European Application No. 10802947.1, which is a national phase of PCT/US2010/043045 filed Jul. 23, 2010 and later published as WO 2011/011680 on Jan. 27, 2011 (Applicant—Vanderbilt University // Inventor—H. Alex Brown, et al.) (2 pages).
(Continued)

*Primary Examiner* — San-Ming Hui
(74) *Attorney, Agent, or Firm* — Ballard Spahr LLP

(57) ABSTRACT

Disclosed are isoform selective Phospholipase D inhibitors. In one aspect, the disclosed compounds can have a structure represented by a formula (I): Also disclosed are methods of making and using the compounds. Also disclosed are pharmaceutical compositions and kits comprising the compounds. This abstract is intended as a scanning tool for purposes of searching in the particular art and is not intended to be limiting of the present invention.

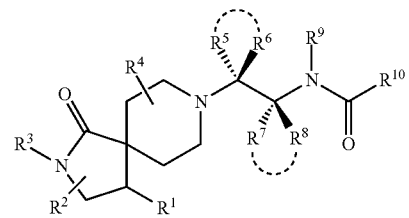

20 Claims, 15 Drawing Sheets

(56) References Cited

U.S. PATENT DOCUMENTS

| | | |
|---|---|---|
| 2004/0029244 A1 | 2/2004 | Williger |
| 2006/0172363 A1 | 8/2006 | Ryu et al. ............ 435/198 |
| 2008/0300298 A1 | 12/2008 | Arbiser |
| 2010/0009970 A1 | 1/2010 | Johansen |
| 2012/0184600 A1 | 7/2012 | Liu |

FOREIGN PATENT DOCUMENTS

| | | |
|---|---|---|
| CA | 2768940 | 1/2012 |
| CN | 201080042304.4 | 3/2012 |
| EP | 10802947.1 | 2/2012 |
| IL | 217720 | 1/2012 |
| IN | 1661/DELNP/2012 | 2/2012 |
| JP | 2012-521826 | 1/2012 |
| KR | 2012-7004698 | 2/2012 |
| MX | MX/a/2012/001064 | 1/2012 |
| RU | 2012106657 | 2/2012 |
| SG | 201200525-2 | 1/2012 |
| WO | WO 96/41634 | 12/1996 |
| WO | PCT/US2010/036660 | 5/2010 |
| WO | PCT/US2010/043045 | 7/2010 |
| WO | PCT/US2012/058192 | 9/2012 |
| WO | PCT/US2013/074496 | 12/2013 |
| WO | PCT/US2013/074502 | 12/2013 |

OTHER PUBLICATIONS

Voluntary Amendment before examination filed Oct. 1, 2012 for European Application No. 10802947.1, which is a national phase of PCT/US2010/043045 filed Jul. 23, 2010 and later published as WO 2011/011680 on Jan. 27, 2011 (Applicant—Vanderbilt University // Inventor—H. Alex Brown, et al.) (15 pages).
Supplementary European search report and opinion issued Dec. 13, 2012 for European Application No. 10802947.1, which is a national phase of PCT/US2010/043045 filed Jul. 23, 2010 and later published as WO 2011/011680 on Jan. 27, 2011 (Applicant—Vanderbilt University // Inventor—H. Alex Brown, et al.) (7 pages).
Invitation to declare maintenance of application issued Jan. 2, 2013 for European Application No. 10802947.1, which is a national phase of PCT/US2010/043045 filed Jul. 23, 2010 and later published as WO 2011/011680 on Jan. 27, 2011 (Applicant—Vanderbilt University // Inventor—H. Alex Brown, et al.) (1 page).
International Search Report issued Sep. 17, 2010 by the International Searching Authority for Application PCT/US2010/043045 filed Jul. 23, 2010 and later published as WO 2011/011680 on Jan. 27, 2011 (Applicant—Vanderbilt University // Inventor—H. Alex Brown, et al.) (1 page).
Written Opinion issued Sep. 17, 2010 by the International Searching Authority for Application PCT/US2010/043045 filed Jul. 23, 2010 and later published as WO 2011/011680 on Jan. 27, 2011 (Applicant—Vanderbilt University // Inventor—H. Alex Brown, et al.) (5 pages).
International Preliminary Report on Patentability issued Jan. 24, 2012 by the International Searching Authority for Application PCT/US2010/043045 filed Jul. 23, 2010 and later published as WO 2011/011680 on Jan. 27, 2011 (Applicant—Vanderbilt University // Inventor—H. Alex Brown, et al.) (6 pages).
Andresen, et al., "The role of phosphatidic acid in the regulation of the Ras/MEK/Erk signaling cascade," *FEBS Letters* 2002, 531(1): 65-8.
Brown, et al., "ADP-ribosylation factor (ARF), a small GTP-dependent regulatory protein, stimulates phospholipase D activity." *Cell* 1993, 75: 1137-1144.
Brown, et al., "Biochemical Analysis of Phospholipase D." In *Methods in Enzymology, vol. 434, Lipidomics and Bioactive Lipids: Lipids and Cell Signaling* 2007. Edited by H. Alex Brown. Elsevier. pp. 49-87.
Eliás, et al., "Molecular diversity of phospholipase D in angiosperms," *BMC Genomics* 2002, 3(1): 2.

Foster DA. "Regulation of mTOR by phosphatidic acid?" *Cancer Res.* 2007, 67(1):1-4.
Henage, et al., Kinetic analysis of a mammalian Phospholipase D: Allosteric modulation by monomeric GTPases, Protein kinase C and polyphosphoinosites. *J. Biol. Chem.* 2006, 281: 3408-3417.
Ivanova, P.T., et al. "Glycerophospholipid identification and quantitation by electrospray ionization mass spectrometry," In *Methods in Enzymology, vol. 432, Lipidomics and Bioactive Lipids: Mass spectrometry based lipid analysis*, 2007. Edited by H. Alex Brown. Elsevier. pp. 21-57.
Kang, et al., "Autoregulation of phospholipase D activity is coupled to selective induction of phospholipase D1 expression to promote invasion of breast cancer cells," *International Journal of Cancer* 2011, 128(4): 805-816.
Korolkovas, "Essentials of medicinal chemistry, isosteric substitutions," in *Essentials of Medicinal Chemistry* 1988, New York, Wiley & Sons, pp. 78-82.
Lavieri, et al., "Design and synthesis of isoform-selective phospholipase D (PLD) inhibitors. Part II. Identification of the 1,3,8-triazaspiro[4,5]decan-4-one privileged structure that engenders PLD2 selectivity," *Bioorganic & Medicinal Chemistry Letters* 2009, 19(8): 2240-2243.
Ponting and Kerr, "A novel family of phospholipase D homologues that includes phospholipid synthases and putative endonucleases: identification of duplicated repeats and potential active site residues," *Protein Sci.* 1996, 5(5):914-922.
Scott, et al., "Design of isoform-selective phospholipase D inhibitors that modulate cancer cell invasiveness," *Nature Chemical Biology* 2009, 5(2): 108-117.
Selvy, et al., "Phospholipase D: Enzymology, Functionality, and Chemical Modulation," *Chemical Reviews* 2011, 111: 6064-6119.
Stuckey and Dixon, "Crystal structure of a phospholipase D family member," *Nat Struct Biol.* 1999, 6(3): 278-284.
Sun and Chen, "mTOR signaling: PLD takes center stage," *Cell Cycle.* 2008, 7(20): 3118-3123.
Vander Heiden, et al., "Understanding the Warburg effect: the metabolic requirements of cell proliferation," *Science.* 2009, 324(5930):1029-1033.
Walker and Brown, "Measurement of G protein stimulated phospholipase D activity in intact cells." In *Methods in Molecular Biology vol. 237: G Protein Signaling: Methods and Protocols* 2004, edited by A.V. Smrcka. Humana Press Inc., pp. 89-97.
Wermuth, "Molecular Variations based on Isosteric Replacements," *Practice of Medicinal Chemistry* 1996, 203-237.
Yang, et al., "Transphosphatidylation by phospholipase D," *J Biol Chem.* 1967, 242(3): 477-484.
Alessi, D. R., et al. (1997) "Characterization of a 3-phosphoinositide-dependent protein kinase which phosphorylates and activates protein kinase B." *Curr. Biol.* 7: 261-269.
Bellacosa, A., et al. (1991) "A retroviral oncogene, akt, encoding a serine-threonine kinase containing an SH2-like region." *Science* 254: 274-277.
Berge, S.M., et al. (1977) "Pharmaceutical Salts." *J. Pharm. Sci.* 66: 1-19.
Bertrand, R., et al. (1994) "Induction of a common pathway of apoptosis by staurosporine." *Exp. Cell Res.* 211: 314-321.
Bundgaard, et al. (1992) "(C) Means to enhance penetration: (1) Prodrugs as a means to improve the delivery of peptide drugs." *Advanced Drug Delivery Reviews* 8(1): 1-38.
Cantley, L.C., (2002) "The phosphoinositide 3-kinase pathway." *Science* 296: 1655-1657.
Cheng, et al. (2009) "PI3K signaling in glioma-animal models and therapeutic challenges." *Brain Pathol.* 19: 112-120.
Chung, J. et al. (1992) "Rapamycin-FKBP specifically blocks growth-dependent activation of and signaling by the 70 kd S6 protein kinases." *Cell* 69: 1227-1236.
Colley, W. C., et al. (1997) "Phospholipase D2, a distinct phospholipase D isoform with novel regulatory properties that provokes cytoskeletal reorganization." *Curr. Biol.* 7: 191-201.
Datta, S. R. et al. (1997) "Akt phosphorylation of BAD couples survival signals to the cell-intrinsic death machinery." *Cell* 91: 231-241.
Dowler, S., et al. (2002) "Protein lipid overlay assay." *Sci. STKE* 6: 6.

(56) References Cited

OTHER PUBLICATIONS

Edwards and Apicella (2006) "*Neisseria gonorrhoeae* PLD directly interacts with Akt kinase upon infection of primary, human, cervical epithelial cells." *Cell Microbiol.* 8: 1253-1271.
Egan, D. F. et al. (2011) "Phosphorylation of ULK1 (hATG1) by AMP-activated protein kinase connects energy sensing to mitophagy." *Science* 331: 456-461.
Fang, Y. et al. (2001) "Phosphatidic acid-mediated mitogenic activation of mTOR signaling." *Science* 294: 1942-1945.
Foster, D., et al. (2003) "Phospholipase D in cell proliferation and cancer." *Mol. Cancer Res.* 1: 789-800.
Foster, D.A. (2009) "Phosphatidic acid signaling to mTOR: signals for the survival of human cancer cells." *Biochim Biophys. Actas* 1791: 949-955.
Franke, T. F., et al. (1995) "The protein kinase encoded by the Akt proto-oncogene is a target of the PDGF-activated phosphatidylinositol 3-kinase." *Cell* 81: 727-736.
Furnari, F.B., et al. (2007) "Malignant astrocytec glioma: genetics, biology, and paths to treatment." *Gene Dev.* 21: 2683-2710.
Garcia-Calvo, M., et al. (1998) "Inhibition of human caspases by peptide-based and macromolecular inhibitors." *J. Biol. Chem.* 273(49): 32608-32613.
Giannone, R., et al. (2007) "Dual-tagging system for the affinity purification of mammalian protein complexes." *Biotech.* 43: 296-302.
Grant no. U54 MH084659 awarded by the National Institute of Health (NIH).
Haas-Kogan, D., et al. (1998) "Protein kinase B (PKB/Akt) activity is elevated in glioblastoma cells due to mutation of the tumor suppressor PTEN/MMAC." *Curr. Biol.* 8: 1195-1198.
Hahn-Windgassen, A. et al. (2005) "Akt activates the mammalian target of rapamycin by regulating cellular ATP level and AMPK activity." *J. Biolog. Chem.* 280: 32081-32089.
Hammond, S. M., et al. (1995) "Human ADP-ribosylation factor-activated phosphatidylcholine-specific phospholipase D defines a new and highly conserved gene family." *J. Biol. Chem.* 270: 29640-29643.
Hardie, D. G. (2007) "AMP-activated/SNF1 protein kinases: conserved guardians of cellular energy." *Nat. Rev. Mol. Cell Bio.* 8: 774-785.
Hawley, S. A. et al. (1996) "Characterization of the AMP-activated protein kinase from rat liver and identification of threonine 172 as the major site at which it phosphorylates AMP-activated protein kinase." *J. Biol. Chem.* 271: 27879-27887.
Higuchi et al. (1975) Prodrugs as Novel Drug Delivery Systems, American Chemical Society.
Hirai, H., et al. (2010) "MK-2206, an allosteric Akt inhibitor, enhances antitumor efficacy by standard chemotherapeutic agents or molecular targeted drugs in vitro and in vivo." *Mol. Cancer Ther.* 9: 1956-1967.
Huang, B. X., et al. (2011) "Phosphatidylserine is a critical modulator for Akt activation." *J. Cell Biol.* 192: 979-992.
Jacobsen, M. D. et al. (1996) "Role of Ced-3/ICE-family proteases in staurosporine-induced programmed cell death." *J. Cell Biol.* 133: 1041-1051.
James, S. R., et al. (1996) "Specific binding of the Akt-1 protein kinase to phosphatidylinositol 3,4,5-trisphosphate without subsequent activation." *Biochem. J.* 315: 709-713.
Jung, C. H. et al. (2010) "mTOR regulation of autophagy." *FEBS Lett.* 584: 1287-1295.
Kabeya, Y., et al. (2000) "LC3, a mammalian homologue of yeast Apg8p, is localized in autophagosome membranes after processing." *EMBO J.* 19: 5720-5728.
Keating, R., et al. (2007) "Virus-specific CD8+ T cells in the liver: armed and ready to kill." *J. Immunol.* 178(5): 2737-2745.
Kennedy, S. G. et al. (1997) "The PI 3-kinase/Akt signaling pathway delivers an anti-apoptotic signal." *Genes & Development* 11: 701-713.
Kihara, A. (2001) "Beclin-phosphatidylinositol 3-kinase complex functions at the trans-Golgi network." *EMBO Reports* 2: 330-335.
Kim, J. et al. (2011) "AMPK and mTOR regulate autophagy through direct phosphorylation of Ulk1." *Nature Cell Bio.* 13: 132-141.
Kimura, S., et al. (2007) "Dissection of the autophagosome maturation process by a novel reporter protein, tandem fluorescent-tagged LC3." *Autophagy* 3: 452-460.
Kohn, A. D., et al. (1996) "Expression of a constitutively active Akt Ser/Thr kinase in 3T3-L1 adipocytes stimulates glucose uptake and glucose transporter 4 translocation." *J. Biol. Chem.* 271: 31372-31378.
Komatsu, M., et al. (2005) "Impairment of starvation-induced and constitutive autophagy in Atg7-deficient mice." *J. Cell Biol.* 169: 425-434.
Kroemer, G., et al. (2010) "Autophagy and the integrated stress response." *Mol. Cell* 40: 280-293.
Kumar, C., et al. (2001) "Expression, purification, characterization and homology modeling of active Akt/PKB, a key enzyme involved in cell survival signaling." *Biochim. Biophys. Acta.* 1526: 257-268.
Lakadamyali, M., et al. (2004) "Endocytosis of influenza viruses." *Microbes Infect.* 6(10): 929-936.
Lam, et al. (2005) "Arrested spread of vesicular stomatitis virus infections in vitro depends on interferon-mediated antiviral activity." *Biotechnol. Bioeng.* 90(7): 793-804.
Lavieri, R. R., et al. (2010) "Design, synthesis, and biological evaluation of halogenated N-(2-(4-oxo-l-phenyl-1,3,8-triazaspiro[4.5]decan-8-yl)ethyl)benzamides: discovery of an isoform-selective small moleculae phospholipase D2 inhibitor." *J. Med. Chem.* 53: 6706-6719.
Lewis, J. A., et al. (2009) "Design and synthesis of isoform-selective phospholipase D (PLD) inhibitors. Part I: Impact of alternative halogenated privileged structures for PLD1 specificity." *Bioorg. Med. Chem. Lett.* 19: 1916-1920.
Liang, X.H., et al. (1999) "Induction of autophagy and inhibition of tumorigenesis by beclin 1." *Nature* 402: 672-676.
Libermann, T.A., et al. (1985) "Amplification, enhanced expression and possible rearrangement of EGF receptor gene in primary human brain tumours of glial origin." *Nature* 313: 144-147.
Mahajan, K., et al. (2010) "Ack1 mediated AKT/PKB tyrosine 176 phosphorylation regulates its activation." *PLoS ONE* 5: e9646.
Manning and Cantley (2007) "AKT/PKB signaling: navigating downstream." *Cell* 129: 1261-1274.
Matsunaga, K., et al. (2009) "Two Beclin 1-binding proteins, Atg14L and Rubicon, reciprocally regulate autophagy at different stages." *Nat. Cell Biol.* 11: 385-396.
Myers, et al. (2011) "Quantitative analysis of glycerophospholipids by LC-MS: acquisition, data handling, and interpretation." *Biochim. Biophys. Acta* 1811: 748-757.
Nielsen and Bundgaard (1988) "Glycolamide esters as biolabile prodrugs of carboxylic acid agents: Synthesis, stability, bioconversion, and physicochemical properties." *J. of Pharmaceutical Sciences* 77(4): 285-298.
Ravikumar, B., et al. (2009) "Mammalian macroautophagy at a glance." *J. Cell Sci.* 122: 1707-1711.
Sarbassov, D. D., et al. (2005) "Phosphorylation and regulation of Akt/PKB by the Rictor-mTOR Complex." *Science* 307: 1098-1101.
Scott, S.A., et al. (2013) "Regulation of phospholipase D activity and phosphatidic acid production after purinergic (P2Y6) receptor stimulation." *J. Biol. Chem.* 288: 20477-20487.
Shin, S.I., et al. (1975) "Tumorigenicity of virus-transformed cells in nude mice is correlated specifically with anchorage independent growth in vitro." *Proc. Natl. Acad. Sci. U.S.A.* 72: 4435-4439.
Singh, S. K., et al. (2004) "Identification of human brain tumour initiating cells." *Nat. Cell Biol.* 432: 396-401.
Sun, H., et al. (1999) "PTEN modulates cell cycle progression and cell survival by regulating phosphatidylinositol 3,4,5-triphosphate and Akt/protein kinase B signaling pathway." *Proc. Natl. Acad. Sci. U.S.A.* 96: 6199-6204.
Sun, Q. et al. (2008) "Identification of Barkor as a mammalian autophagy-specific factor for Beclin 1 and class III phosphatidylinositol 3-kinase." *Proc. Natl. Acad. Sci. U.S.A.* 105: 19211-19216.

(56) References Cited

OTHER PUBLICATIONS

Thomas, C., et al. (2002) "High-resolution structure of the pleckstrin homology domain of protein kinase b/akt bound to phosphatidylinositol (3,4,5)-triphosphate." *Curr. Biol.* 12: 1256-1262.

Thoreen, C. C., et al. (2009) "An ATP-competitive mammalian target of rapamycin inhibitor reveals rapamycin-resistant functions of mTORC1." *J. Biol. Chem.* 284(12): 8023-8032.

Tsujimoto and Shimizu (2005) "Another way to die: autophagic programmed cell death." *Cell Death Differ.* 12 Suppl 2: 1528-1534.

Vance and Vance (2008) "Physiological consequences of disruption of mammalian phospholipid biosynthetic genes." *J. Lipid Res.* 50 Suppl: S132-7.

Wang, Q. J., et al. (2006) "Induction of autophagy in axonal dystrophy and degeneration." *J. Neurosci.* 26: 8057-8068.

Wang, J., et al. (2010) "Notch promotes radioresistance of glioma stem cells." *Stem Cells* 28: 17-28.

Yao, F. et al. (1998) "Tetracycline repressor, tetR, rather than the tetR-mammalian cell transcription factor fusion derivatives, regulates inducible gene expression in mammalian cells." *Hum. Gene Ther.* 9: 1939-1950.

Requirement for Restriction issued on Apr. 1, 2014 for U.S. Appl. No. 14/103,795, filed Dec. 11, 2013 and published as U.S. Pat. No. 2014-0163055 A1 on Jun. 12, 2014 (Applicant—Vanderbilt University // Inventor—Brown et al.) (7 pages).

Response to Restriction filed on Jun. 2, 2014 for U.S. Appl. No. 14/103,795, filed Dec. 11, 2013 and published as U.S. Pat. No. 2014-0163055 A1 on Jun. 12, 2014 (Applicant—Vanderbilt University // Inventor—Brown et al.) ( 7 pages).

Non-Final Office Action issued on Aug. 25, 2014 for U.S. Appl. No. 14/103,795, filed Dec. 11, 2013 and published as U.S. Pat. No. 2014-0163055 A1 on Jun. 12, 1024 (Applicant—Vanderbilt University // Inventor—Brown et al.) (7 pages).

Hsu et al, "Phospholipase D signaling pathway is involved in lung cancer-derived IL-8 increased osteoclastogenesis," Carcinogenesis, vol. 31, No. 4, pp. 587-596, (2010).

Nozawa et al., "Inhibition of Platelet-derived Growth Factor-induced Cell Growth Signaling by a Short Interfering RNA for EWS-Fli1 via Down-regulation of Phospholipase D2 in Ewing Sarcoma Cells," The Journal of Biological Chemistry, vol. 280, No. 30, Issue of Jul. 29, pp. 27544-27551, (2005).

Paruch et al., "CCR5 signaling through phospholipase D involves p44/42 MAP-kinases and promotes HIV-1 LTR-directed gene expression," The FASEB Journal, vol. 21, No. 14, pp. 4038-4046 (Dec. 2007).

International Preliminary Report on Patentability issued Apr. 1, 2014 for International Patent Application No. PCT/US2012/058192, which was filed on Sep. 30, 2012 and published as WO/2013/049773 on Apr. 4, 2013 (Inventor—Brown, et al.; Applicant—Vanderbilt University) (pp. 1-6).

International Search Report and Written Opinion issued Dec. 4, 2012 for International Patent Application No. PCT/US2012/058192, which was filed on Sep. 30, 2012 and published as WO/2013/049773 on Apr. 4, 2013 (Inventor—Brown, et al.; Applicant—Vanderbilt University)(pp. 1-8).

International Search Report issued Apr. 15, 2014 for International Patent Application No. PCT/US2013/074502, which was filed on Dec. 11, 2013 and published as WO/2014/093557 on Jun. 19, 2014 (Inventor—Brown, et al.; Applicant—Vanderbilt University)(pp. 1-2).

International Search Report issued Apr. 25, 2014 for International Patent Application No. PCT/US2013/074496, which was filed on Dec. 11, 2013 and published as WO/2014/093553 on Jun. 19, 2014 (Inventor—Brown, et al.; Applicant—Vanderbilt University)(pp. 1-2).

Restriction Requirement issued Feb. 9, 2015 for U.S. Appl. No. 14/103,795, filed Dec. 11, 2013 and published as U.S. Pat. No. 2014/0163055 on Jun. 12, 2014 (Inventor—Brown, et al.; Applicant—Vanderbilt University) (pp. 1-10).

Response to Non-Final Office Action filed Nov. 25, 2014 for U.S. Appl. No. 14/103,795, filed Dec. 11, 2013 and published as U.S. Pat. No. 2014/0163055 on Jun. 12, 2014 (Inventor—Brown, et al.; Applicant—Vanderbilt University) (pp. 1-15).

U.S. Appl. No. 61/228,492, filed Jul. 24, 2009, H. Alex Brown (Vanderbilt University).

U.S. Appl. No. 61/541,935, filed Sep. 30, 2011, H. Alex Brown (Vanderbilt University).

U.S. Appl. No. 14/348,036, Craig W. Lindsley (Vanderbilt University).

U.S. Appl. No. 61/736,003, filed Dec. 11, 2012, H. Alex Brown (Vanderbilt University).

U.S. Appl. No. 14/103,819, filed Dec. 11, 2013, H. Alex Brown (Vanderbilt University).

U.S. Appl. No. 61/735,998, filed Dec. 11, 2013, H. Alex Brown (Vanderbilt University).

Restriction Requirement issued Mar. 16, 2015 for U.S. Appl. No. 14/103,819, which was filed on Dec. 11, 2013 and published as U.S. Pat. No. 2014/0378524 A1 on Dec. 25, 2014 (Inventor—Brown// Applicant—Vanderbilt University) (7 pages).

Restriction Requirement issued Feb. 9, 2015 for U.S. Appl. No. 14/103,795, which was filed on Dec. 11, 2013 and published as U.S. Pat. No. 2014/0163055 on Jun. 12, 2014 (Inventor—Brown//Applicant—Vanderbilt University) (10 pages).

ISOFORM SELECTIVE PHOSPHOLIPASE D INHIBITORS

CROSS-REFERENCE TO RELATED APPLICATIONS

This application claims the benefit of U.S. Application No. 61/228,492, filed Jul. 24, 2009; which is hereby incorporated herein by reference in entirety

BACKGROUND

Phospholipase D (PLD; EC3.1.4.4.) enzymes are phosphodiesterases that hydrolyze phospholipids to phosphatidic acid (PA) are their free head groups. In mammalian cells the principal substrate is phosphatidylcholine (PC), and the production of PA has broad biological functions. PA regulates biophysical properties of cellular membranes, acts as a second messenger to alter activities of many enzymes and proteins, and is subsequently metabolized to diacylglycerols and lysophosphatidic acids by lipid phosphate phosphatase and phospholipase $A_2$, respectively. Diacylglycerols derived from PCs are important cellular signaling molecules and lysophosphatidic acid is released as an extracellular messenger that affects many cell types. Evidence supports a role for PLD in regulated exocytosis, cell proliferation, membrane trafficking, and tumor formation.

Isoenzymes of PLD have been cloned from animals, fungi, plants, bacteria, and viruses. Two mammalian PLD genes (PLD1 and PLD2) have been identified, and several splice variant protein products have been characterized. The mammalian isoenzymes have a conserved primary sequence and domain structure but are differentially regulated by upstream signaling pathways. Both enzymes are members of the PXPH-PLD subfamily that have a pleckstrin homology (PH) and phox homology (PX) domains in tandem at their N terminal (Eliás M, Potocký M, Cvrcková F, Zárskjý V., "Molecular diversity of phospholipase D in angiosperms," BMC Genomics. 2002; 3(1):2. Epub 2002 Feb. 1) and are hypothesized to have pseudodimeric catalytic domains with invariant $HXKX_4D$ motifs (Ponting C P, Kerr I D., "A novel family of phospholipase D homologues that includes phospholipid synthases and putative endonucleases: identification of duplicated repeats and potential active site residues," Protein Sci. 1996 May; 5(5):914-22.; Stuckey J. A., Dixon J. E., "Crystal structure of a phospholipase D family member," Nat Struct Biol. 1999 March; 6(3):278-84.).

The production of PA has broad physiological impact and choline release has been suggested to play a role in acetylcholine synthesis. PLD was initially identified in plants and early experiments on purified cabbage PLD (Yang S. F., Freer S., Benson A. A., "Transphosphatidylation by phospholipase D," J Biol Chem. 1967 Feb. 10; 242(3):477-84.) established both a phosphatidylcholine phosphohydrolase activity (Eq. 1) and a competing phosphatidylcholine transphosphatidylase activity (Eq. 2).

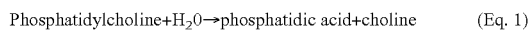
(Eq. 1)

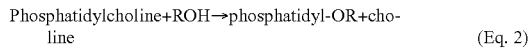
(Eq. 2)

Transfer of phosphatidyl groups from phospholipid substrates to primary alcohols (ROH) yields phosphatidylalcohols (Eq. 2). Because of their unique origin, low abundance in biological membranes, and metabolic stability, the formation of phosphatidylalcohols has been used as a specific marker for PLD activity. Specific in vitro and in vivo assay systems have been developed to allow the identification of signaling modulators, relative activities, and substrate-product relationships using electrospray ionization mass spectrometry (Brown, H. A., Gutowski, S., Moomaw, C. R., Slaughter, C., and Sternweis, P. C. (1993) ADP-ribosylation factor (ARF), a small GTP-dependent regulatory protein, stimulates phospholipase D activity. Cell 75: 1137-1144; Walker, S. J. and Brown, H. A. (2003) Measurement of G protein stimulated phospholipase D activity in intact cells. In Methods in Molecular Biology vol 237: G Protein Signaling: Methods and Protocols, edited by A.V. Smrcka.Humana Press Inc., Totowa, N.J.; and Brown, H. A., Henage, L. G., Preininger, A. M., Xiang, Y., and Exton, J. H. (2007) Biochemical Analysis of Phospholipase D. In Methods in Enzymology. 434, Lipidomics and Bioactive Lipids: Lipids and Cell Signaling. Edited by H. Alex Brown. Elsevier. pp. 49-87.).

Because of the roles of PLD and its products, the enzymatic activity of PLD is tightly regulated by a variety of hormones, neurotransmitters, growth factors, cytokines, integrins, and other cellular signals. The PLD1 isoenzyme is under extensive control both in vitro and in vivo. This tight regulation is in part the reason the enzyme was difficult to study for several decades until it was determined that phosphatidylinositol 4,5-bisphosphate (PIN was an essential regulator of catalytic activity (Brown et al., 1993). Interaction between PLD and lipid vesicles is dependent upon $PIP_2$ (Henage, L., Exton, J. and Brown, H. A. Kinetic analysis of a mammalian Phospholipase D: Kinetic analysis of a mammalian Phospholipase D: Allosteric modulation by monomeric GTPases, Protein kinase C and polyphosphoinosites. (2006) J. Biol. Chem. 281: 3408-3417.). This interaction is mediated primarily by a conserved polybasic region within a C-terminal PLD catalytic subdomain, but there also appear to be additional sites where PLD and phosphoinositides directly interact. Previous work suggests that there are distinct yet interacting binding sites for the major regulators. Mutational studies have identified PLD1 domains and amino acid sequences involved in these interactions. PLD1 activity is regulated by conventional isoforms of protein kinase C through a direct protein-protein interaction that is not dependent upon kinase activity. PLD1 is also regulated by members of the Rho and Arf GTPase families.

By contrast PLD2 has a relatively high basal activity and does not require modulation by GTPases for activation. Initially this lead to an incorrect assumption that PLD1 was the signaling isoenzyme and PLD2 was involved in more mundane housekeeping functions. Recent evidence has shown that both PLD1 and PLD2 are activated by many cell surface receptors, including tyrosine kinase growth factor receptors. The production of PA appears to be essential to mediating the downstream processes modulated by these growth promoting and cell proliferative pathways.

Previous work from a number of laboratories has suggested a role for PLD in a number of cellular processes required for growth, proliferation, transformation and tumor formation. The presence of Arf and PLD on Golgi membranes followed by reports that PA has a role in the formation of coated vesicles suggests a role in vesicle trafficking. PLD is associated with the translocation of the glucose transporter, Glut-4, to the plasma membrane and PLD activity has been implicated in the internalization of the epidermal growth factor receptor. These studies have relied on the use of primary alcohols to interfere with the formation of PA by PLD, but further support has been obtained through the expression of catalytically inactive PLD mutants and more recently using RNA interference techniques to block the expression of PLD isoenzymes. Each of these approaches has limitations, so the development of specific, isoenzyme selective inhibitors is expected to greatly complement these previous approaches. PLD couples signal-transduction networks bidirectionally to the cytoskeleton. Several findings have implicated a role for PLD in controlling cell shape, motility, chemotaxis, and vesicle trafficking. Rho, Rac, and Cdc42 have been implicated in these processes as well and each has been shown to activate PLD through protein-protein interactions.

Many studies have implicated a role for PLD in regulation of cell survival. Many signaling networks and mitogenic signals involved in modulating cell survival and apoptotic pathways have been shown to include a role for PLD. The specifics vary with cell types. In some cells PLD activity is proapoptotic, while in others PLD promotes cell survival and mitogenesis. Recent findings suggest that PLD1 activation leads to an increase in RAS-ERK/PI3K (reviewed in Andresen B T, Rizzo M A, Shome K, Romero G., "The role of phosphatidic acid in the regulation of the Ras/MEK/Erk signaling cascade," FEBS Lett. 2002 Oct. 30; 531(1):65-8. Review.) and NFκB signaling cascade (Dong Woo Kang, Mi Hee Park, Craig Lindsley, H Alex Brown and Do Sik Min, "Regulation of Phospholipase D1 signaling dynamics via enzymatic activity dependent positive feedback loop," Molecular and Cellular Biology (2009), in review.) and subsequently selective expression of PLD1 in breast cancer cells. This leads to growth factor-induced matrix metalloproteinase upregulation which is essential to cancer cell migration and metastasis. PLD generated PA has also been proposed to directly modulated the mTOR pathway, which is known to play a major role in the development of several types of human cancers (reviewed by Foster D A. "Regulation of mTOR by phosphatidic acid?" Cancer Res. 2007 Jan. 1; 67(1):1-4. Review; Sun Y, Chen J. "mTOR signaling: PLD takes center stage," Cell Cycle. 2008 October; 7(20):3118-23. Epub 2008 Oct. 27. Review.). Growth factor receptor signaling pathways, information on cell growth, nutrient status, and cellular bioenergetics are integrated through the mTOR circuit. Several recent studies suggest that the actions of many cellular oncogenes may explain the pioneering observations of Otto Warburg with regard to the propensity of most cancer cells to preferentially utilize aerobic glycolysis pathway in their cellular bioenergetics. Several recent studies have suggested that modulation of the mTOR pathway may be among the most important with respect to the development of the next generation of anti-cancer therapeutics (Vander Heiden M G, Cantley L C, Thompson C B., "Understanding the Warburg effect: the metabolic requirements of cell proliferation," Science. 2009 May 22; 324(5930):1029-33.). PLD appears to play an important role in the regulation of these key signaling and cell survival pathways. Isoenzyme selective inhibitors of PLD may provide a novel and effective mechanism for inhibition of cancer cell transformation and metastasis.

Despite previous research, there remains a need for compounds and compositions useful as isoform selective Phospholipase D inhibitors that overcome current deficiencies and that effectively treat diseases and disorders associated with Phospholipase D. The disclosed compounds, compositions, and methods address this need as well as other needs.

SUMMARY

In accordance with the purpose(s) of the invention, as embodied and broadly described herein, the invention, in one aspect, relates to isoform selective Phospholipase D inhibitors.

Disclosed are compounds comprising a structure represented by a formula:

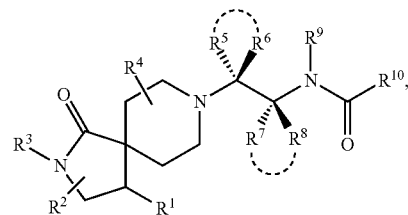

wherein ----- each independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof.

Also disclosed are compounds having a structure represented by a formula:

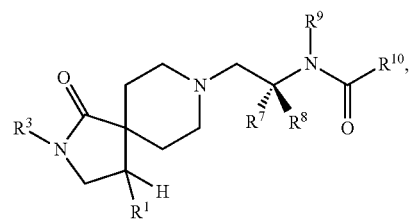

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein $R^{10}$ comprises an optionally substituted C1 to C12 organic residue selected from alkyl, aryl, heteroaryl, cycloalkyl, heterocycloalkyl, cycloalkenyl, and heterocycloalkenyl.

Also disclosed are pharmaceutical compositions comprising a therapeutically effective amount of a compound having a structure represented by a formula:

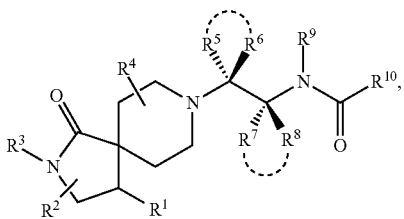

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof, and a pharmaceutically acceptable carrier.

Also disclosed are methods for preparing a compound comprising the steps of providing a compound having a structure:

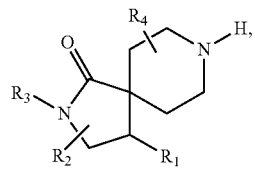

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and reacting with a compound having a structure:

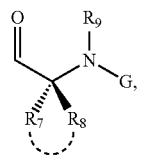

wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue, and wherein G is a protecting group.

Also disclosed are methods for preparing a compound comprising the steps of providing a compound having a structure:

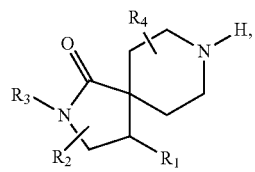

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and reacting with a compound having a structure:

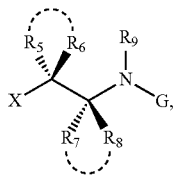

wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue, wherein G is a protecting group, and wherein X is a leaving group.

Also disclosed are methods for preparing a compound comprising the steps of providing a compound having a structure:

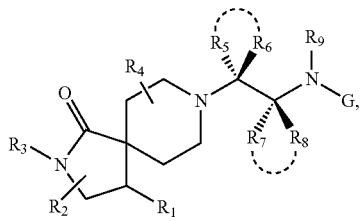

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein G is a protecting group, and reacting with a compound having a structure:

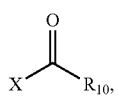

wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, and wherein X is a leaving group.

Also disclosed are the products of the disclosed methods.

Also disclosed are pharmaceutical compositions comprising a therapeutically effective amount of a disclosed product and a pharmaceutically acceptable carrier.

Also disclosed are methods for manufacturing a medicament comprising combining at least one disclosed compound or at least one product of a disclosed method with a pharmaceutically acceptable carrier or diluent.

Also disclosed are methods for the treatment of a disorder associated with PLD activity in a mammal comprising the step of administering to the mammal at least one disclosed compound or at least one product of a disclosed method in a dosage and amount effective to treat the disorder in the mammal.

Also disclosed are methods for inhibiting PLD activity in a mammal comprising the step of administering to the subject at least one disclosed compound or at least one product of a disclosed method in a dosage and amount effective to inhibit PLD activity in the subject.

Also disclosed are methods for inhibiting PLD activity in at least one cell, comprising the step of contacting the at least one cell with at least one disclosed compound or at least one product of a disclosed method in an amount effective to inhibit PLD activity response in the at least one cell.

Also disclosed are uses of a compound for PLD inhibition, the compound having a structure represented by a formula:

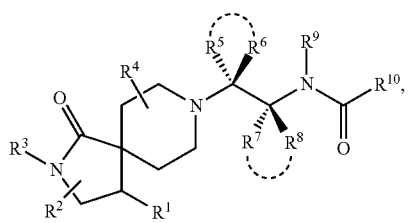

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof.

Also disclosed are uses of at least one disclosed compound or at least one product of a disclosed method in the manufacture of a medicament for the treatment of a condition associated with PLD activity.

Also disclosed are uses of at least one disclosed compound or at least one product of a disclosed method in the manufacture of a medicament for the treatment of a disorder associated with PLD activity in a mammal.

Also disclosed are kits comprising at least one disclosed compound or at least one product of a disclosed method and at least one agent known to increase PLD activity.

Also disclosed are kits comprising at least one disclosed compound or at least one product of a disclosed method and at least one agent known to decrease PLD activity.

BRIEF DESCRIPTION OF THE FIGURES

The accompanying figures, which are incorporated in and constitute a part of this specification, illustrate several aspects and together with the description serve to explain the principles of the invention.

Figure 1:
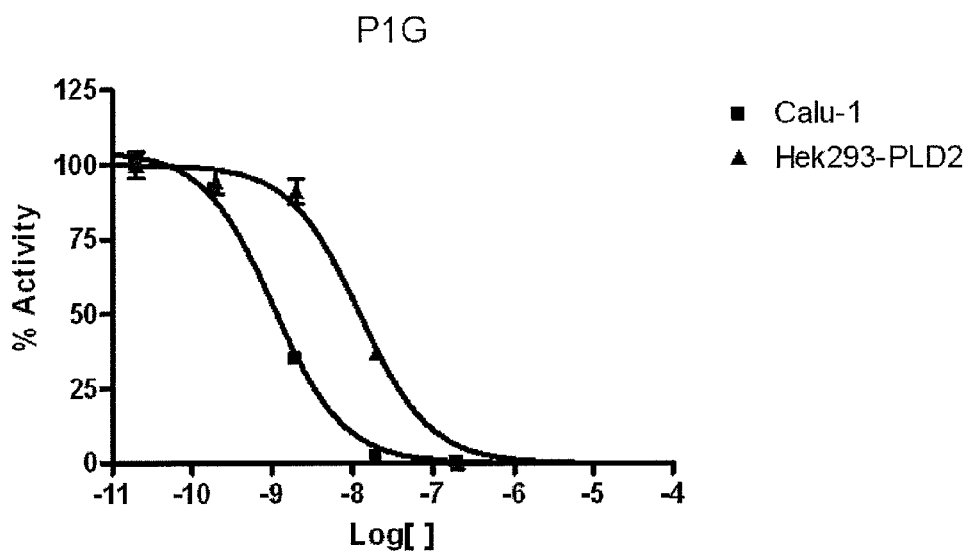
FIG. 1 shows cellular enantiopure concentration response curves for compound P1G (see TABLE 1).
Figure 2:
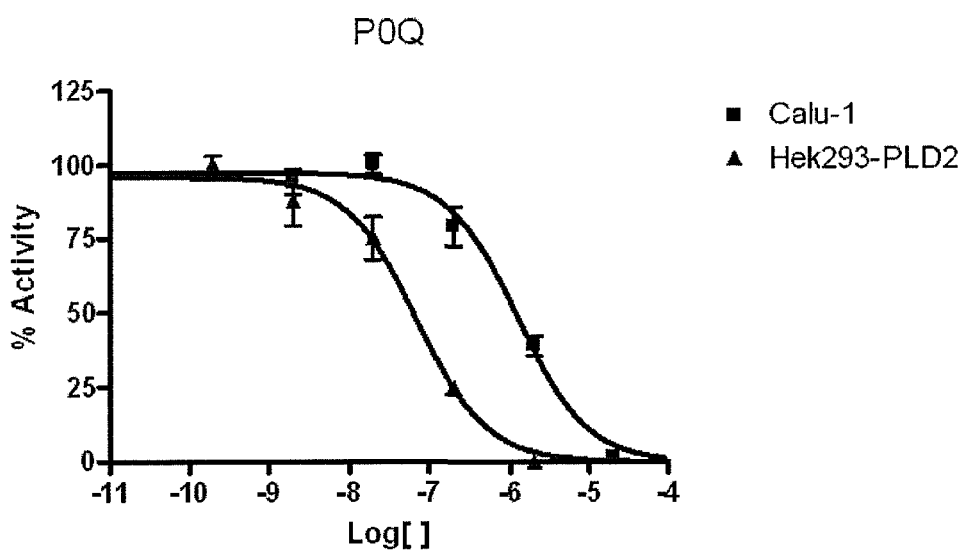
FIG. 2 shows cellular enantiopure concentration response curves for compound P0Q (see TABLE 1).
Figure 3:
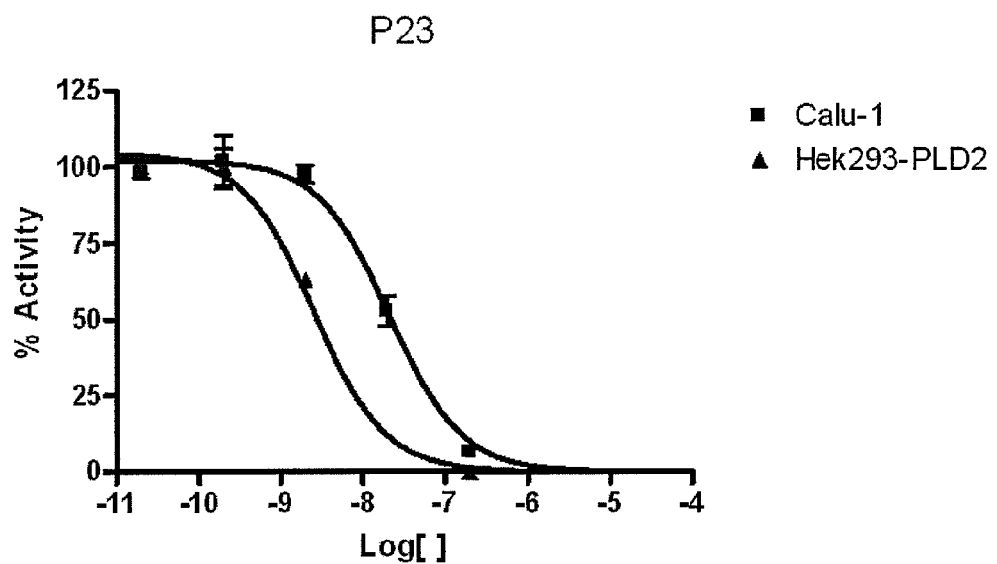
FIG. 3 shows cellular enantiopure concentration response curves for compound P23 (see TABLE 1).
Figure 4:
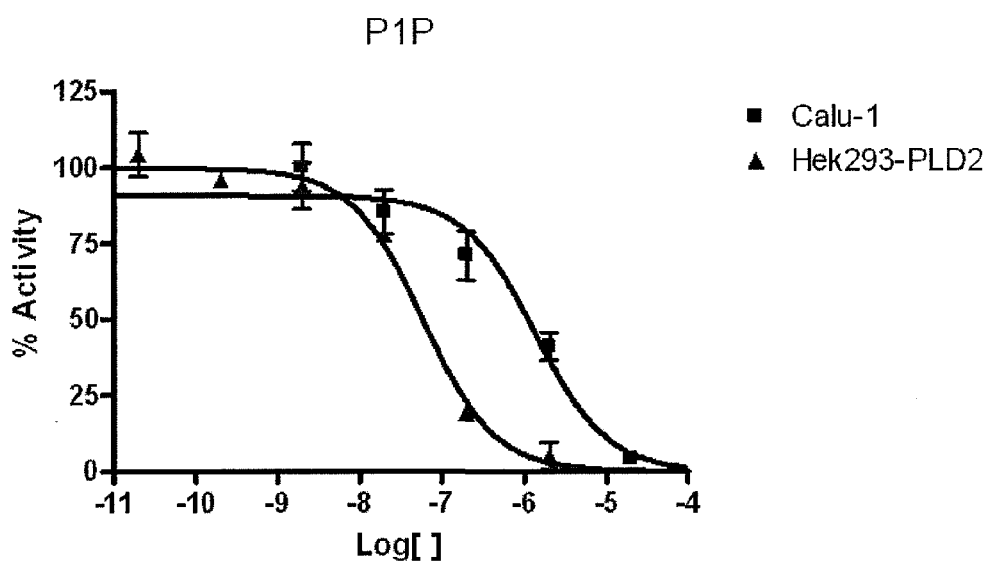
FIG. 4 shows cellular enantiopure concentration response curves for compound P1P (see TABLE 1).
Figure 5:
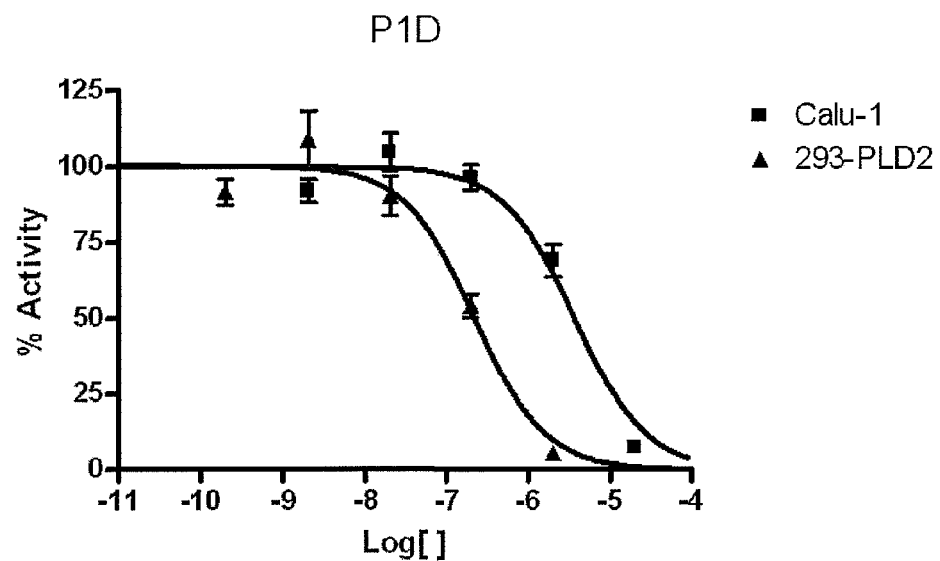
FIG. 5 shows cellular enantiopure concentration response curves for compound P1D (see TABLE 1).
Figure 6:
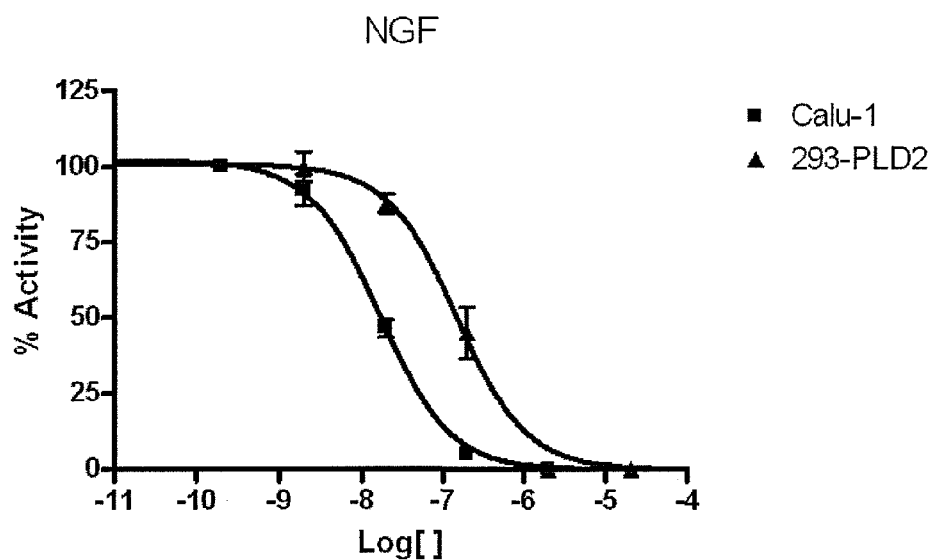
FIG. 6 shows cellular enantiopure concentration response curves for compound NGF (see TABLE 1).
Figure 7:
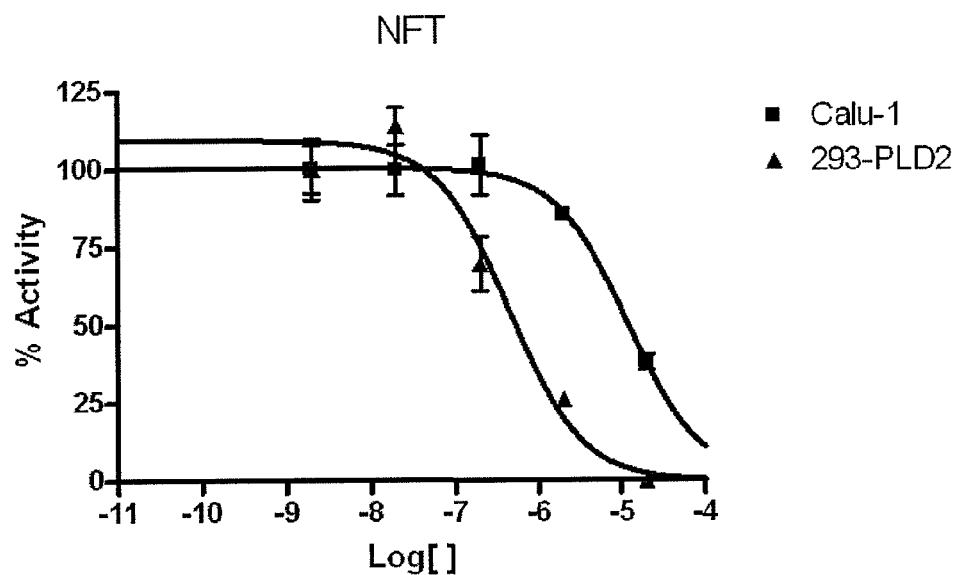
FIG. 7 shows cellular enantiopure concentration response curves for compound NFT (see TABLE 1).
Figure 8:
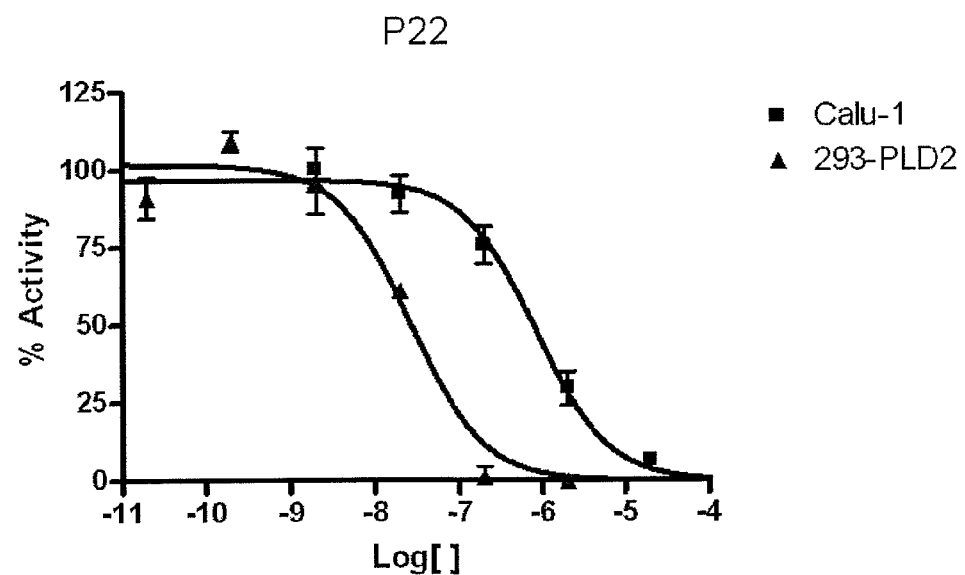
FIG. 8 shows cellular enantiopure concentration response curves for compound P22 (see TABLE 1).
Figure 9:
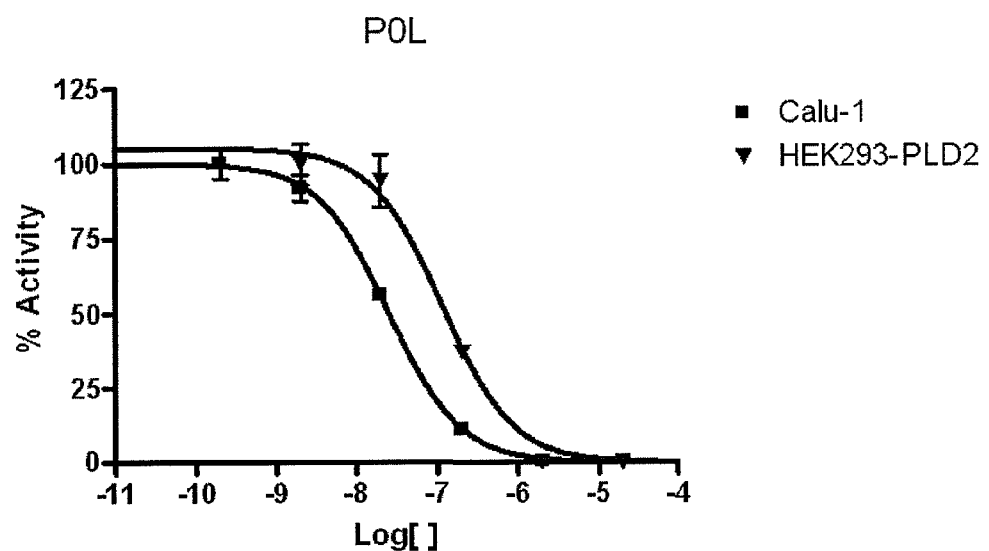
FIG. 9 shows cellular enantiopure concentration response curves for compound P0L (see TABLE 1).
Figure 10:
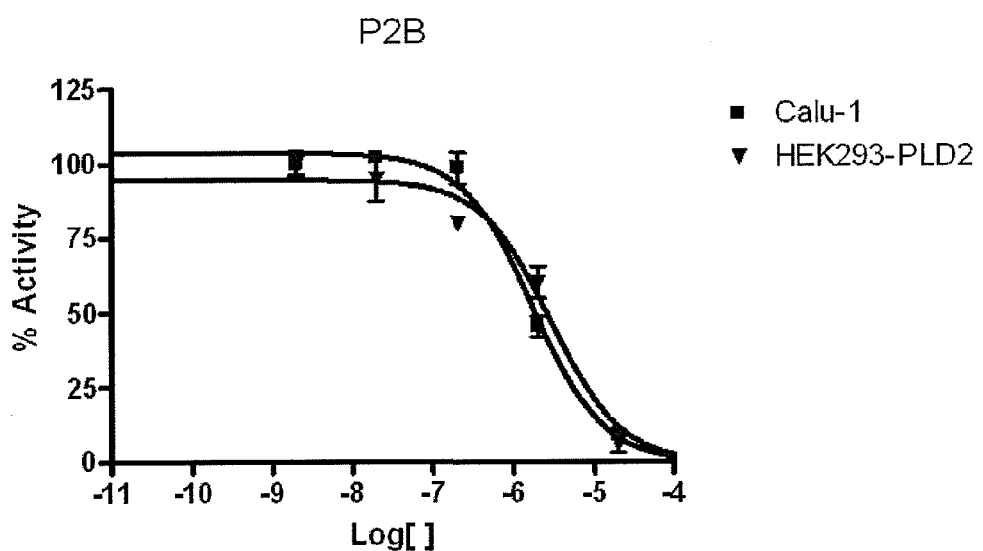
FIG. 10 shows cellular enantiopure concentration response curves for compound P2B (see TABLE 1).
Figure 11:
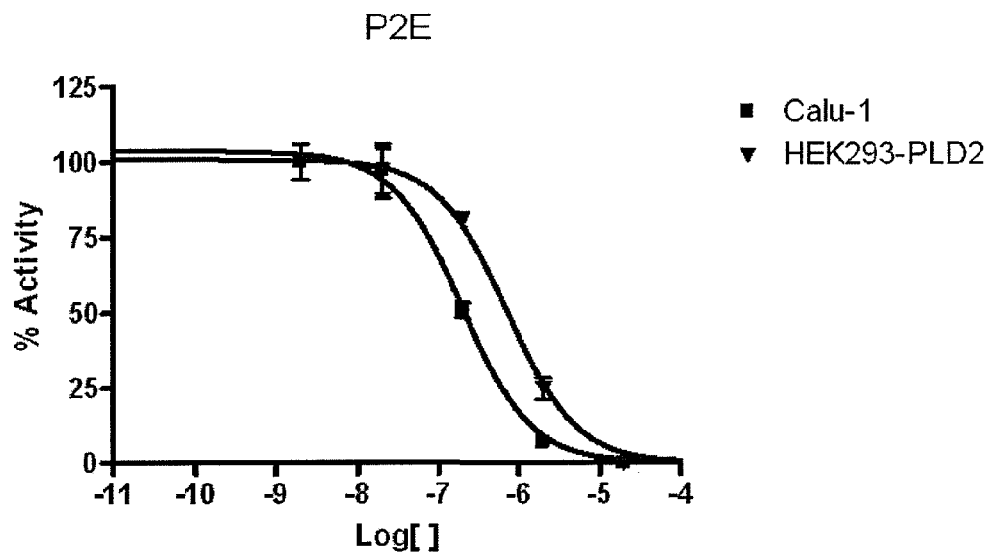
FIG. 11 shows cellular enantiopure concentration response curves for compound P2E (see TABLE 1).
Figure 12:
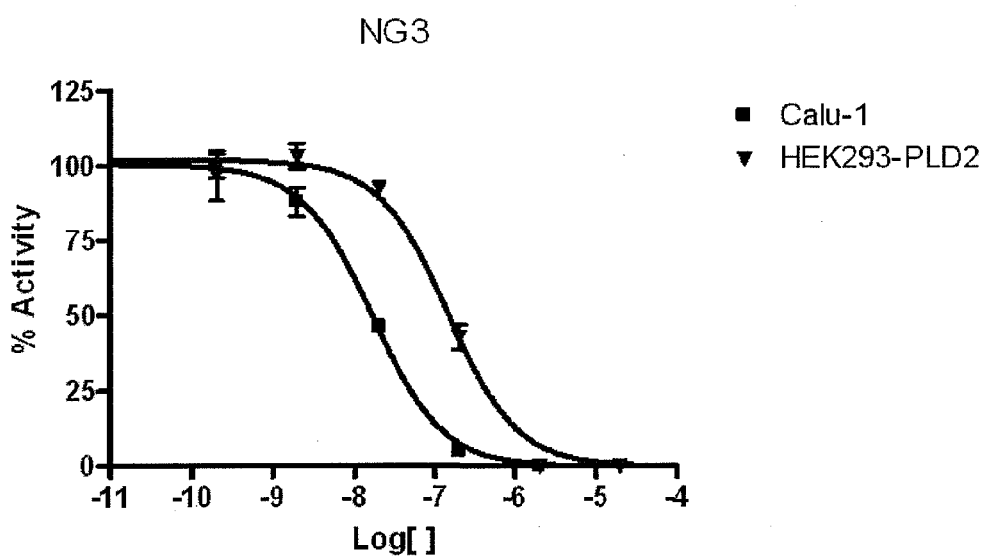
FIG. 12 shows cellular enantiopure concentration response curves for compound NG3 (see TABLE 1).
Figure 13:
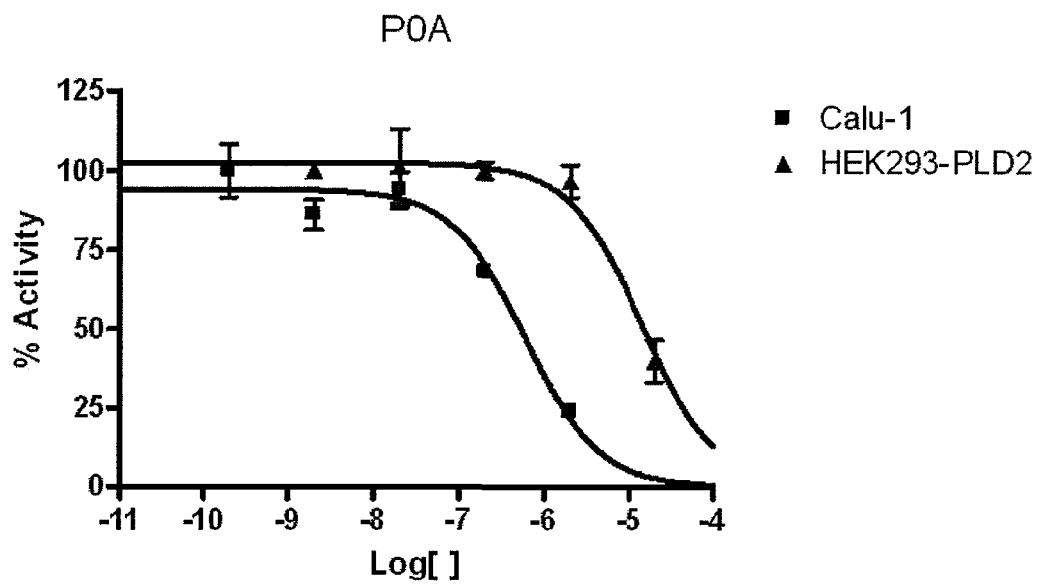
FIG. 13 shows cellular enantiopure concentration response curves for compound P0A (see TABLE 1).
Figure 14:
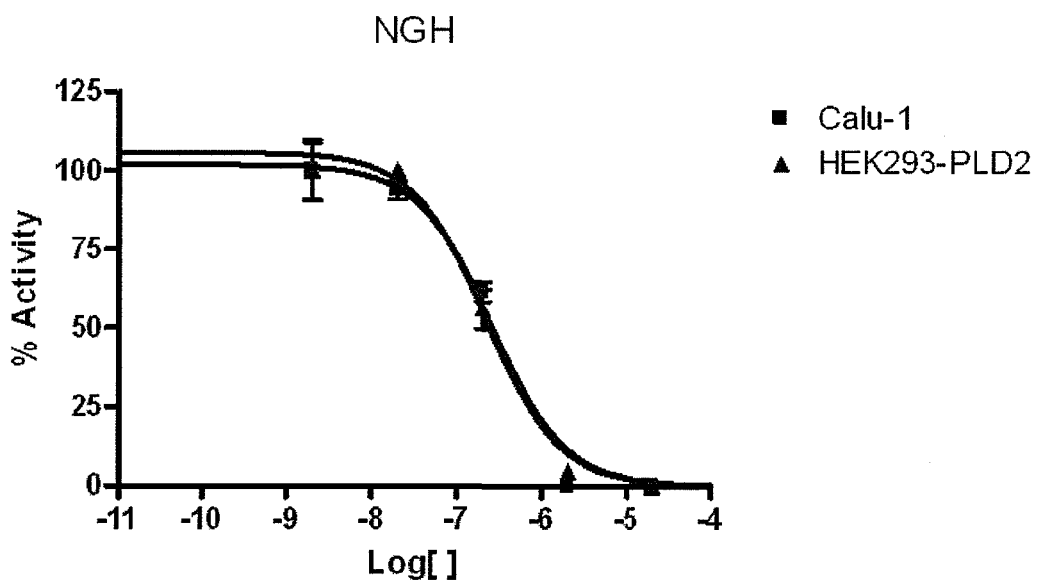
FIG. 14 shows cellular enantiopure concentration response curves for compound NGH (see TABLE 1).
Figure 15:
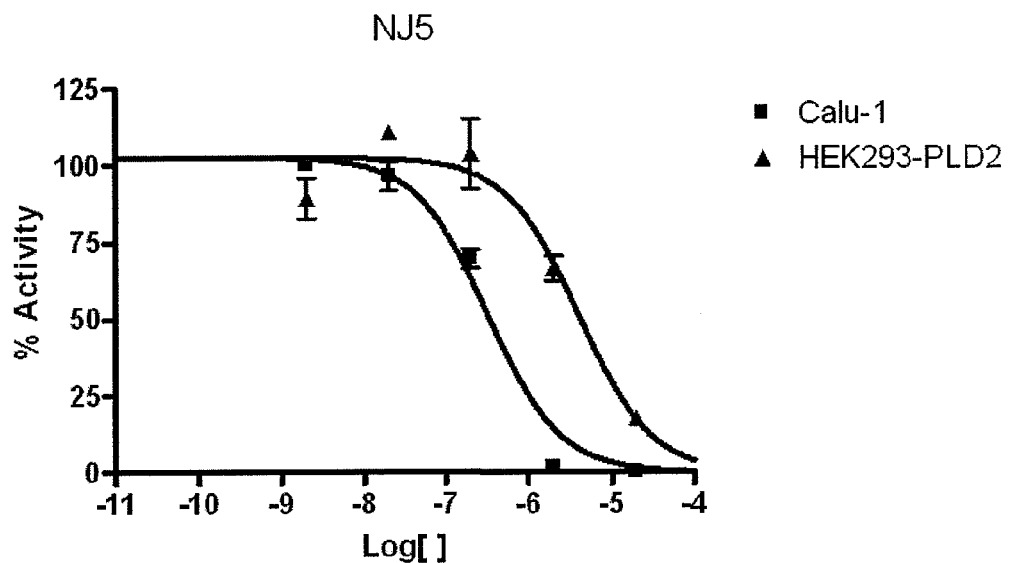
FIG. 15 shows cellular enantiopure concentration response curves for compound NJ5 (see TABLE 1).
Figure 16:
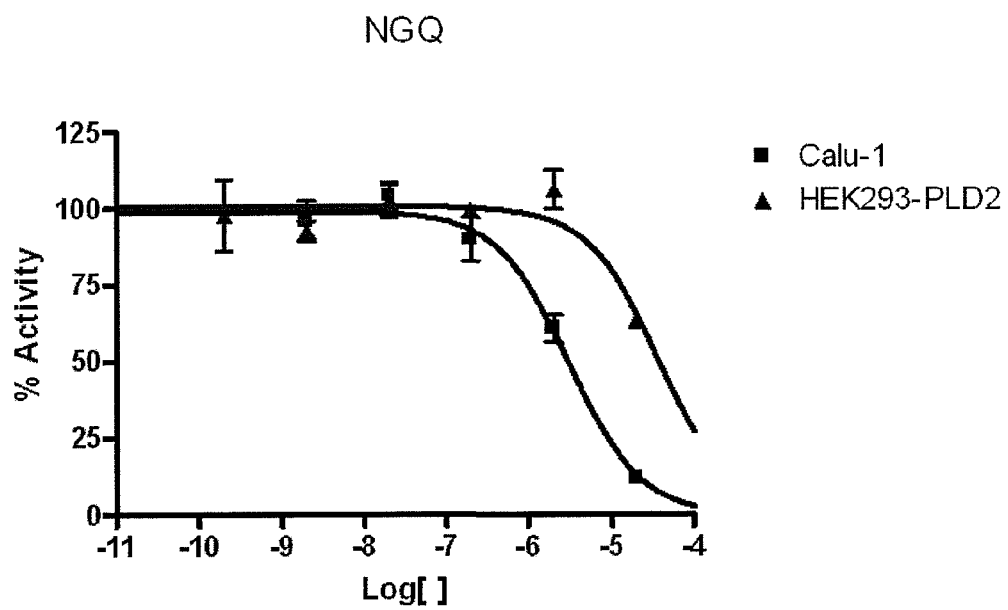
FIG. 16 shows cellular enantiopure concentration response curves for compound NGQ (see TABLE 1).
Figure 17:
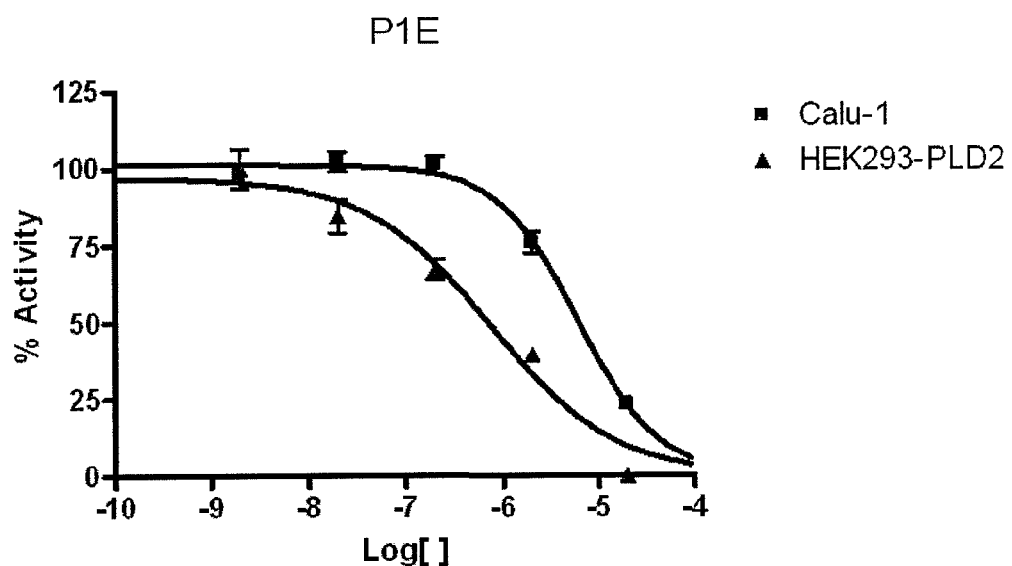
FIG. 17 shows cellular enantiopure concentration response curves for compound P1E (see TABLE 1).
Figure 18:
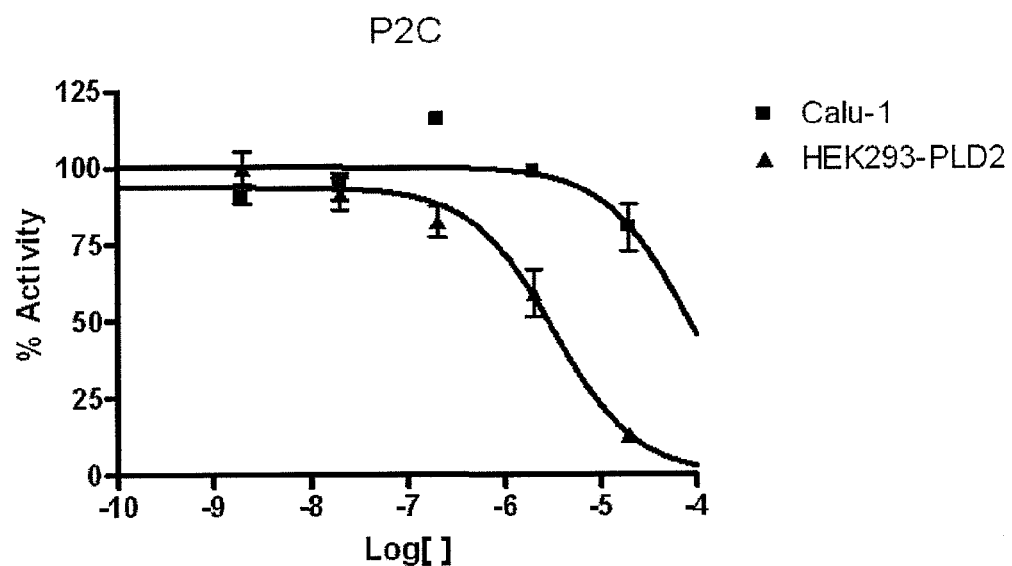
FIG. 18 shows cellular enantiopure concentration response curves for compound P2C (see TABLE 1).
Figure 19:
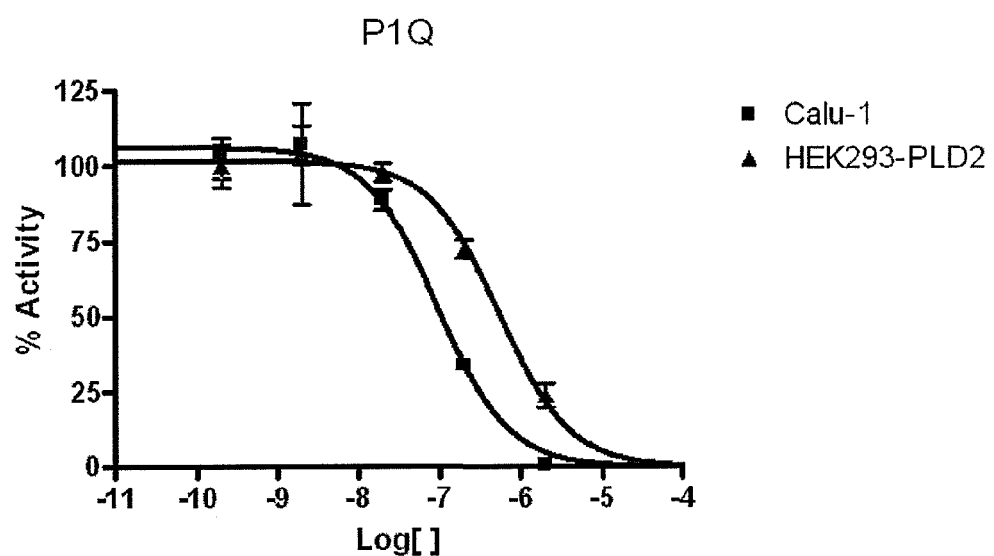
FIG. 19 shows cellular enantiopure concentration response curves for compound P1Q (see TABLE 1).
Figure 20:
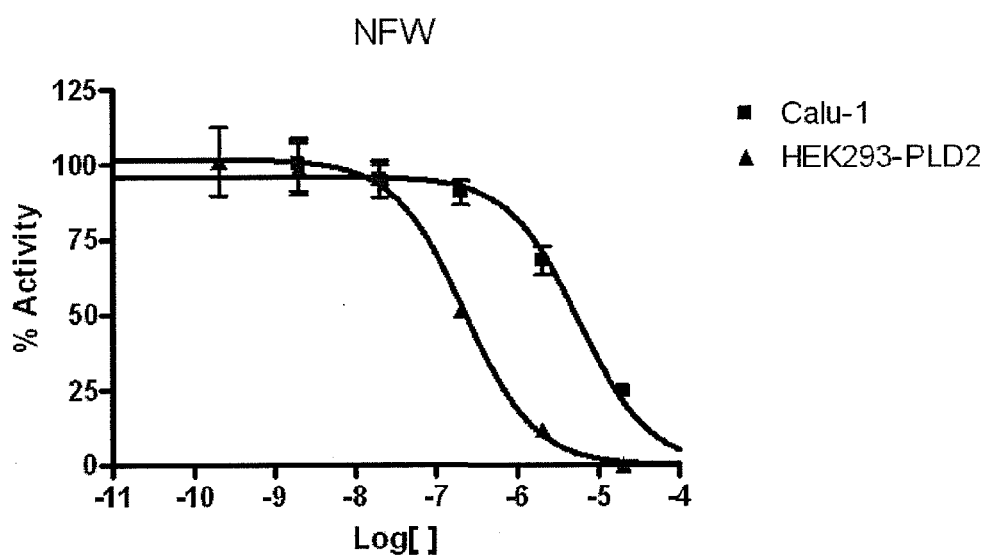
FIG. 20 shows cellular enantiopure concentration response curves for compound NFW (see TABLE 1).
Figure 21:
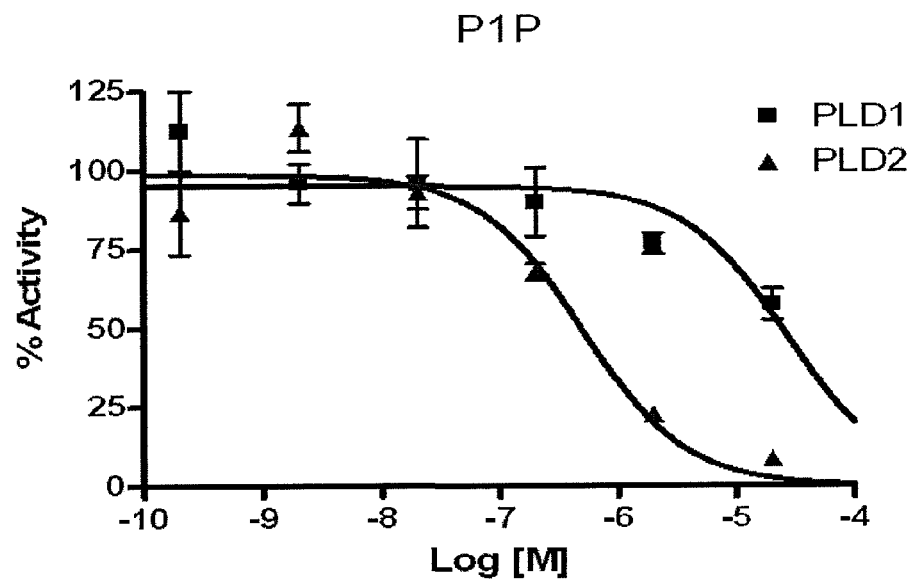
FIG. 21 shows exogenous concentration response curves for compound P1P (see TABLE 1).
Figure 22:
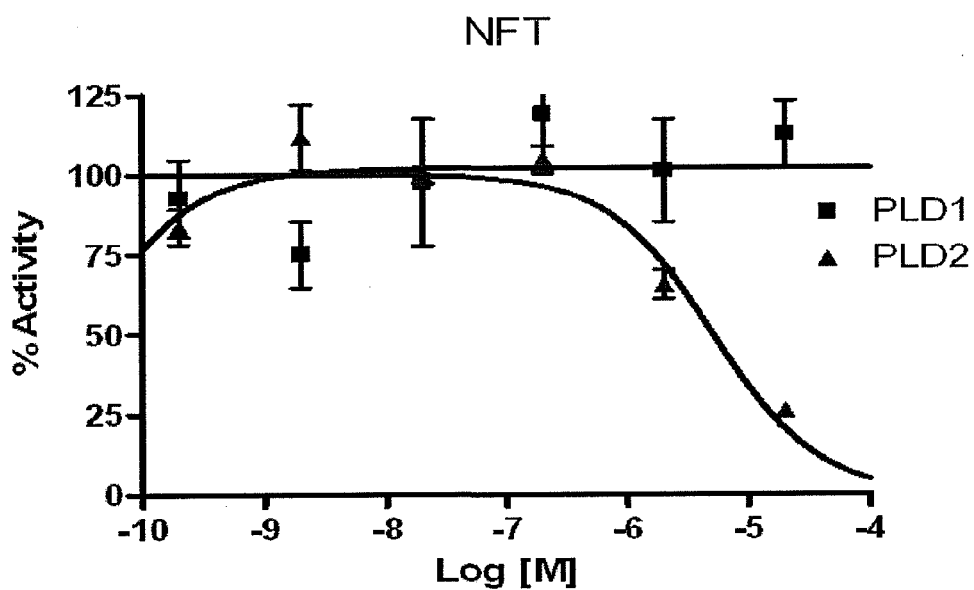
FIG. 22 shows exogenous concentration response curves for compound NFT (see TABLE 1).
Figure 23:
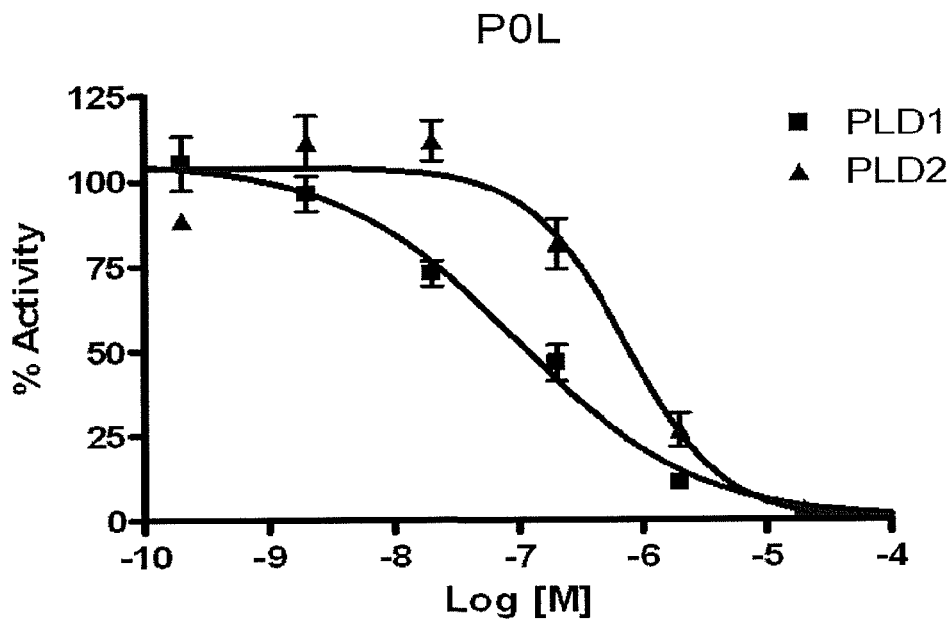
FIG. 23 shows exogenous concentration response curves for compound P0L (see TABLE 1).
Figure 24:
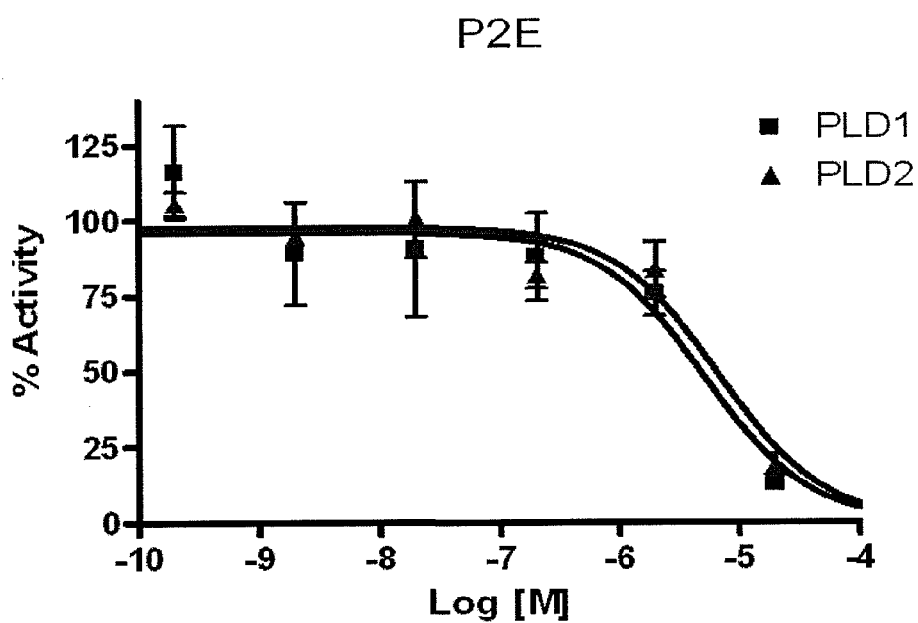
FIG. 24 shows exogenous concentration response curves for compound P2E (see TABLE 1).
Figure 25:
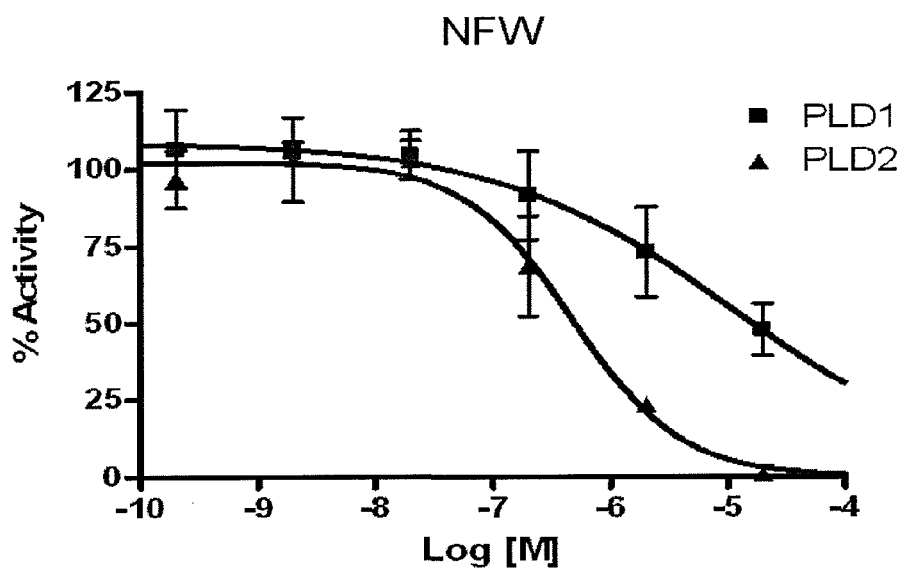
FIG. 25 shows exogenous concentration response curves for compound NFW (see TABLE 1).
Figure 26:
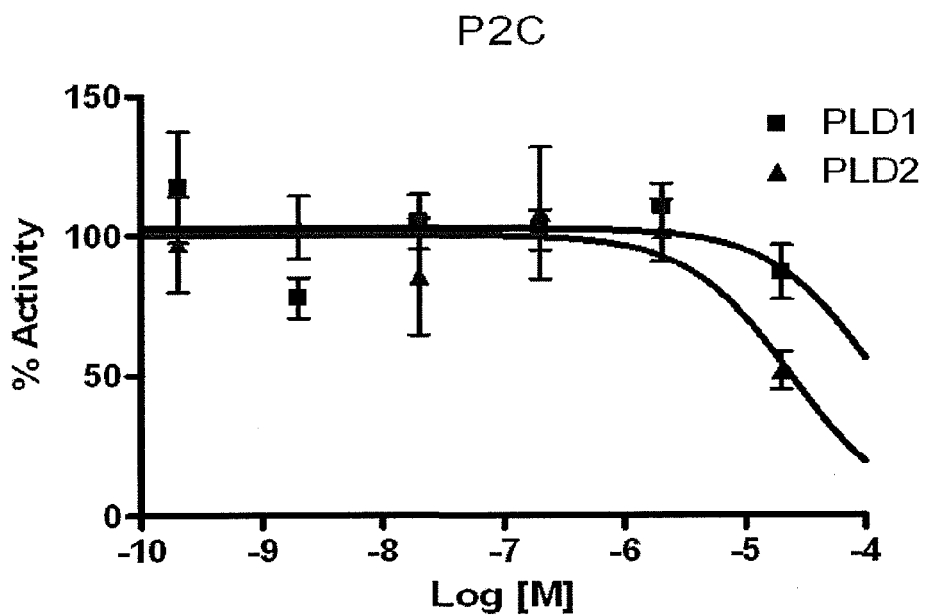
FIG. 26 shows exogenous concentration response curves for compound P2C (see TABLE 1).
Figure 27:
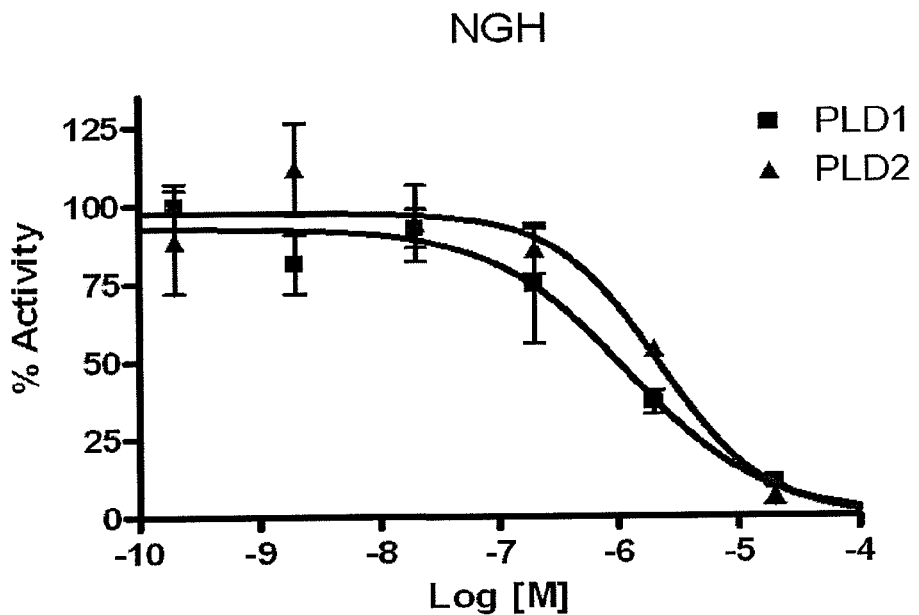
FIG. 27 shows exogenous concentration response curves for compound NGH (see TABLE 1).
Figure 28:
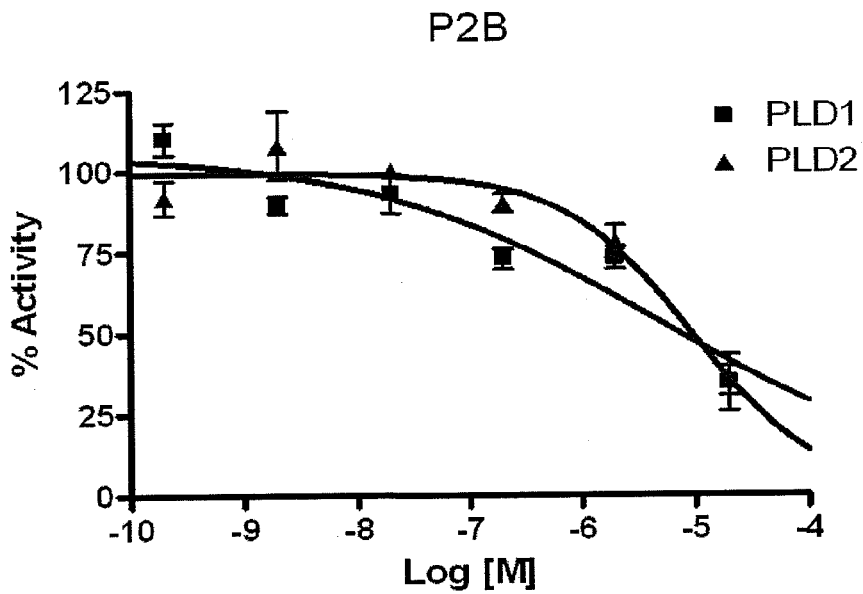
FIG. 28 shows exogenous concentration response curves for compound P2B (see TABLE 1).
Figure 29:
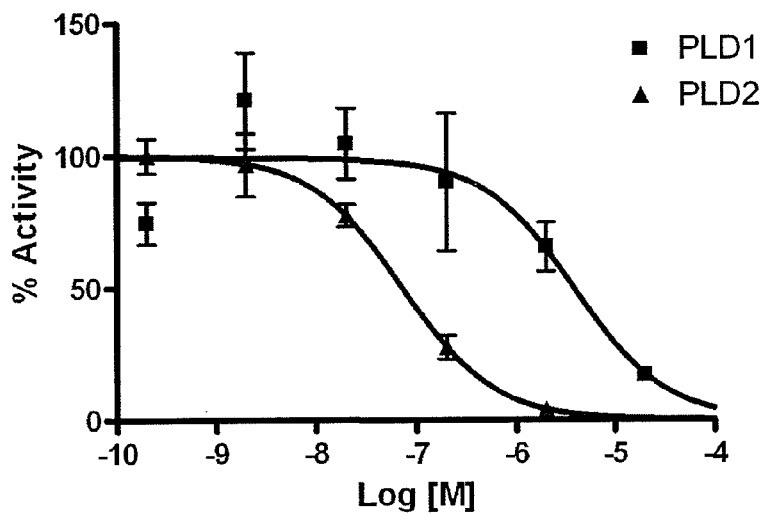
FIG. 29 shows exogenous concentration response curves for compound P22 (see TABLE 1).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "optional" or "optionally" means that the subsequently described event or circumstance may or may not occur, and that the description includes instances where said event or circumstance occurs and instances where it does not.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of from 1 to 24 carbon atoms, for example from 1 to 12 carbons, from 1 to 8 carbons, from 1 to 6 carbons, or from 1 to 4 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C═C(A$^3$A$^4$) are intended to include both the E and Z isomers. This can be presumed in structural formulae herein wherein an asymmetric alkene is present, or it can be explicitly indicated by the bond symbol C═C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A$^1$C(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined herein above. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

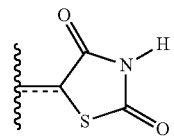

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In some aspects, a structure of a compound can be represented by a formula:

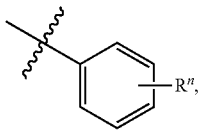

which is understood to be equivalent to a formula:

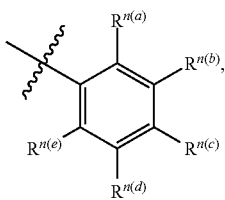

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain instances of the above defined terms may occur more than once in the structural formulae, and upon such occurrence each term shall be defined independently of the other.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by selective inhibition of Phospholipase D1" means having been subjected to a physical examination by a person of skill, for example, a physician, and found to have a condition that can be diagnosed or treated by a compound or composition that can inhibit PLD1. As a further example, "diagnosed with a need for selective inhibition of Phospholipase D2" refers to having been subjected to a physical examination by a person of skill, for example, a physician, and found to have a condition characterized by PLD2 activity. Such a diagnosis can be in reference to a disorder, such as a disease of uncontrolled cellular proliferation, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to PLD2 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "hydrolysable residue" is meant to refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. COMPOUNDS

In one aspect, the invention relates to compounds, or pharmaceutically acceptable derivatives thereof, useful as isoform selective Phospholipase D inhibitors. In general, it is contemplated that each disclosed compound or derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound comprises a structure represented by a formula:

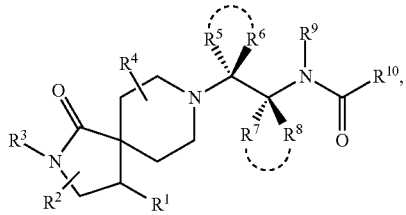

wherein ----- each independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof.

In a further aspect, a compound has a structure represented by a formula:

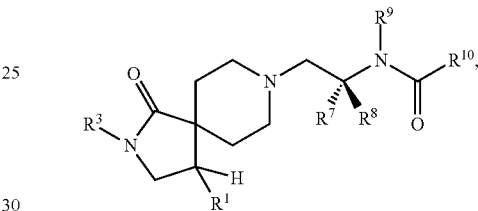

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein $R^{10}$ comprises an optionally substituted C1 to C12 organic residue selected from alkyl, aryl, heteroaryl, cycloalkyl, heterocycloalkyl, cycloalkenyl, and heterocycloalkenyl.

In a further aspect, a compound has a structure represented by a formula:

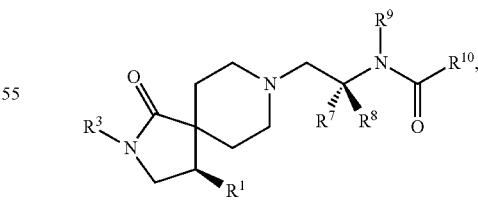

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein $R^{10}$ comprises an optionally substituted C1 to C12 organic residue selected from alkyl, aryl, heteroaryl, cycloalkyl, heterocycloalkyl, cycloalkenyl, and heterocycloalkenyl.

In a further aspect, a compound has a structure represented by a formula:

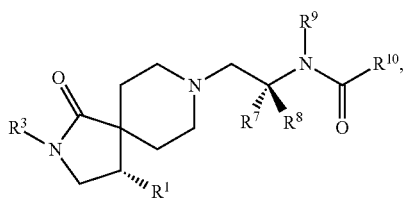

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein $R^{19}$ comprises an optionally substituted C1 to C12 organic residue selected from alkyl, aryl, heteroaryl, cycloalkyl, heterocycloalkyl, cycloalkenyl, and heterocycloalkenyl.

In a further aspect, a compound has a structure represented by a formula:

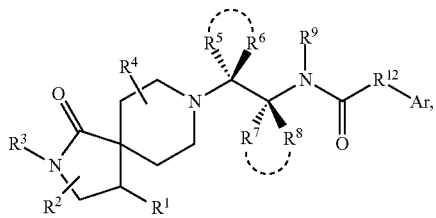

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

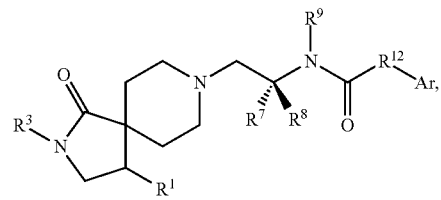

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

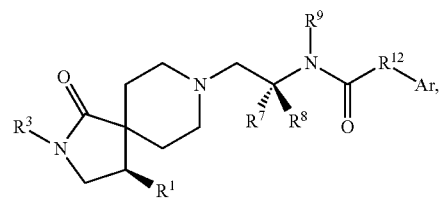

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

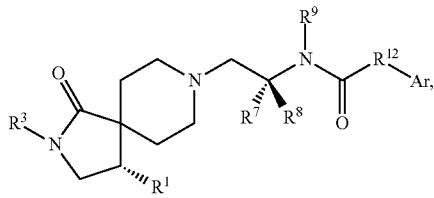

wherein R¹ is an optionally substituted C3 to C9 organic residue selected from aryl, heteroaryl, cycloalkyl, heterocycloalkyl, cycloalkenyl, and heterocycloalkenyl; wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

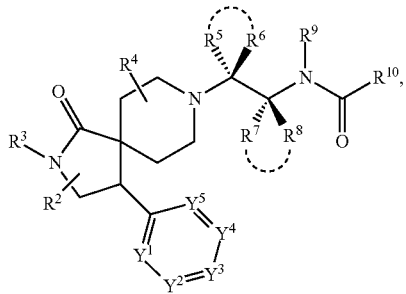

wherein each ----- independently comprises an optional covalent bond; wherein R² comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R³ comprises hydrogen, an optionally substituted C1 to C6 alkyl, an optionally substituted C3 to C6 cycloalkyl, or a hydrolysable residue; wherein R⁴ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of R⁵ and R⁶ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or R⁵ and R⁶, together with the intermediate carbon, comprise an optionally substituted C3 to C6 cycloalkyl; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or R⁷ and R⁸, together with the intermediate carbon, comprise an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹⁰ comprises an optionally substituted C1 to C12 organic residue selected from alkyl, aryl, heteroaryl, cycloalkyl, heterocycloalkyl, cycloalkenyl, and heterocycloalkenyl; and wherein each of Y¹, Y², Y³, Y⁴, and Y⁵ independently comprises N or C—R¹¹, wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

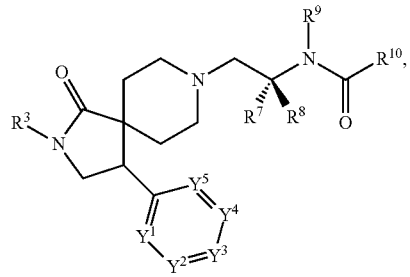

wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹⁰ comprises an optionally substituted C1 to C12 organic residue selected from alkyl, aryl, heteroaryl, cycloalkyl, heterocycloalkyl, cycloalkenyl, and heterocycloalkenyl; and wherein each of Y¹, Y², Y³, Y⁴, and Y⁵ independently comprises N or C—R¹¹, wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

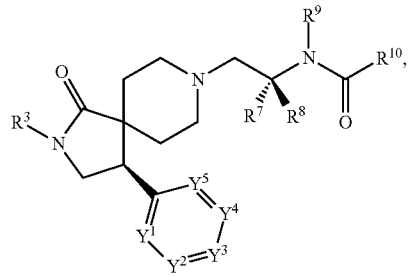

wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl; and wherein each of $Y^1, Y^2, Y^3, Y^4$, and $Y^5$ independently comprises N or $C$—$R^{11}$, wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

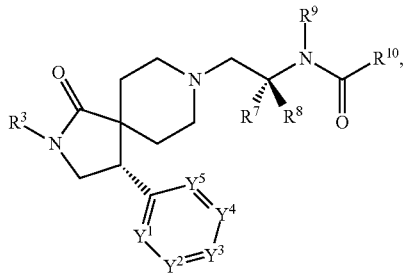

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl; and wherein each of $Y^1, Y^2, Y^3, Y^4$, and $Y^5$ independently comprises N or $C$—$R^{11}$, wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

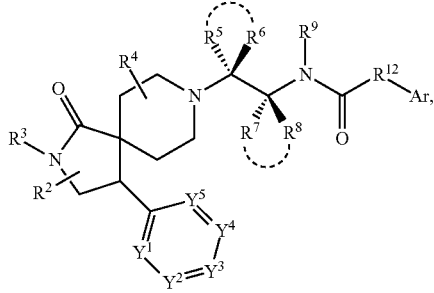

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each of $Y^1, Y^2, Y^3, Y^4$, and $Y^5$ independently comprises N or $C$—$R^{11}$, wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

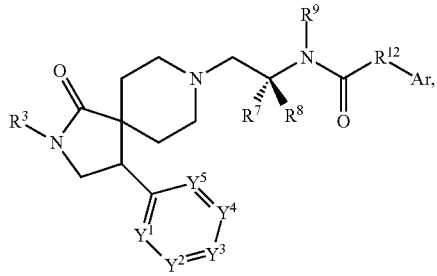

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each of $Y^1, Y^2, Y^3, Y^4$, and $Y^5$ independently comprises N or $C$—$R^{11}$, wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

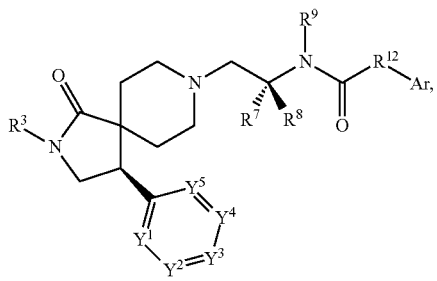

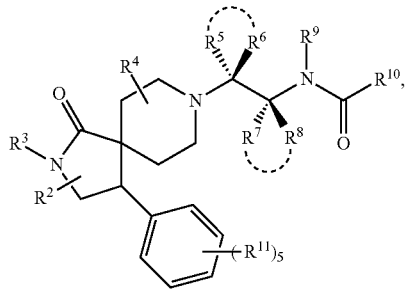

wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein each of Y¹, Y², Y³, Y⁴, and Y⁵ independently comprises N or C—R¹¹, wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

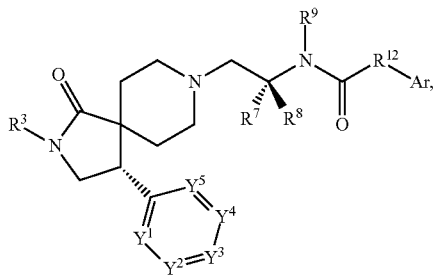

wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein each of Y¹, Y², Y³, Y⁴, and Y⁵ independently comprises N or C—R¹¹, wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

wherein each ----- independently comprises an optional covalent bond; wherein R² comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R³ comprises hydrogen, an optionally substituted C1 to C6 alkyl, an optionally substituted C3 to C6 cycloalkyl, or a hydrolysable residue; wherein R⁴ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of R⁵ and R⁶ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or R⁵ and R⁶, together with the intermediate carbon, comprise an optionally substituted C3 to C6 cycloalkyl; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or R⁷ and R⁸, together with the intermediate carbon, comprise an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹⁰ comprises an optionally substituted C1 to C12 organic residue selected from alkyl, aryl, heteroaryl, cycloalkyl, heterocycloalkyl, cycloalkenyl, and heterocycloalkenyl; and wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

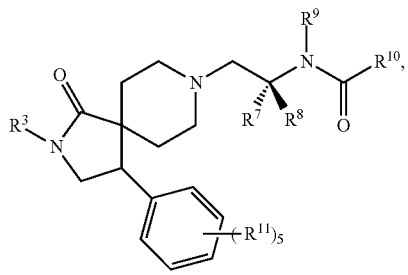

wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl; and wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

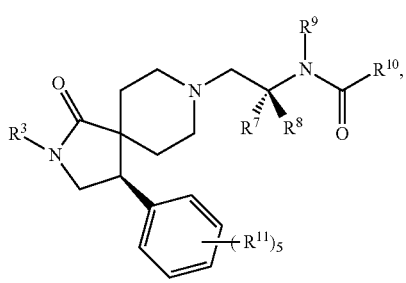

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl; and wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

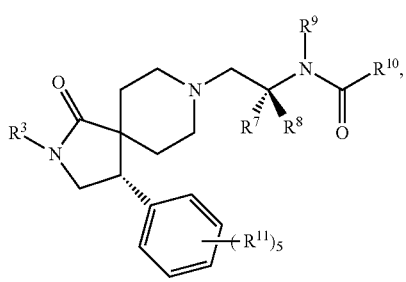

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl; and wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue.

In a further aspect, a compound has a structure represented by a formula:

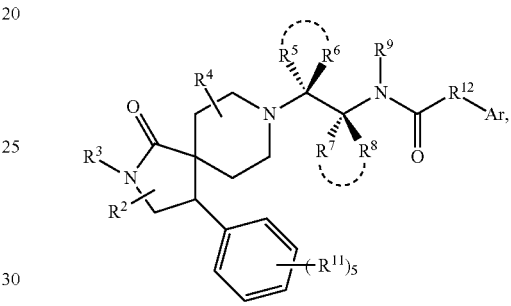

wherein each ----- independently comprises an optional covalent bond; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

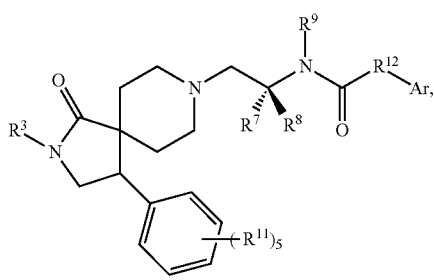

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

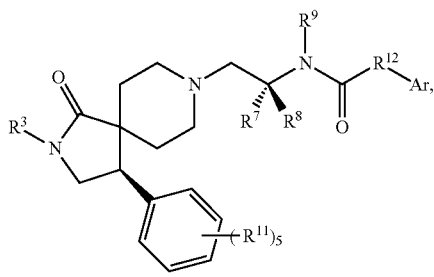

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

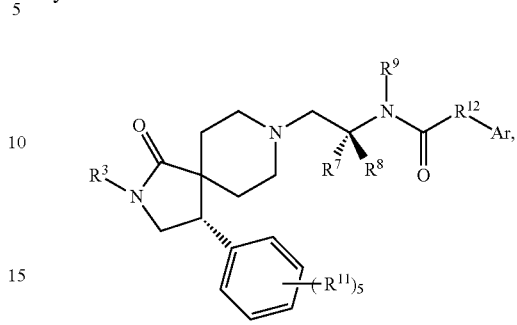

wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

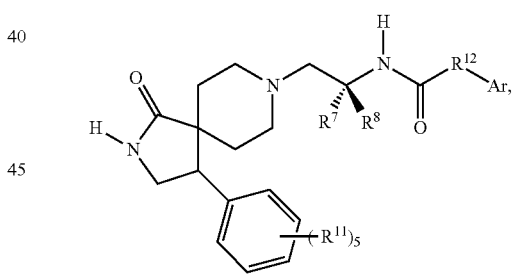

wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

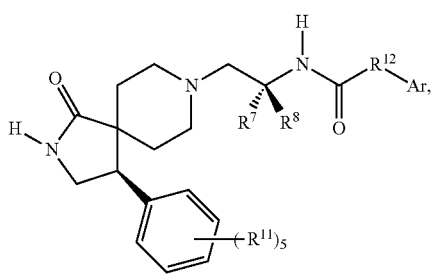

wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

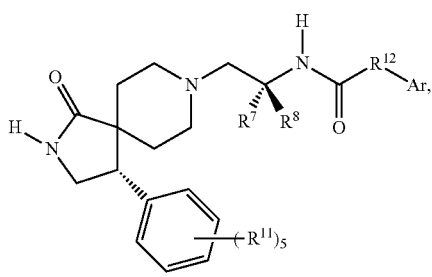

wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

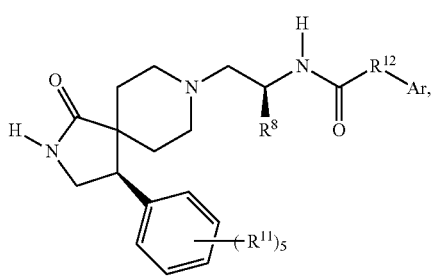

wherein R⁸ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

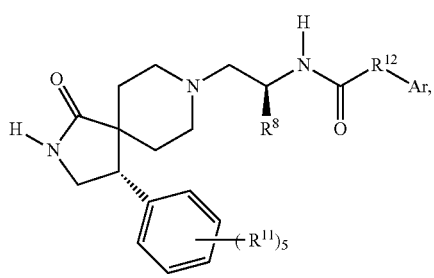

wherein R⁸ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

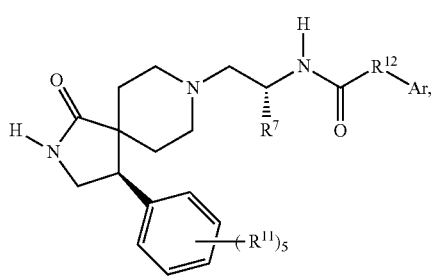

wherein R⁷ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each R¹¹ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein R¹² is a covalent bond, a C1 to C3 alkyl, or a C1 to C3 cycloalkyl; and wherein Ar is an optionally substituted C4 to C10 organic residue selected from aryl and heteroaryl.

In a further aspect, a compound has a structure represented by a formula:

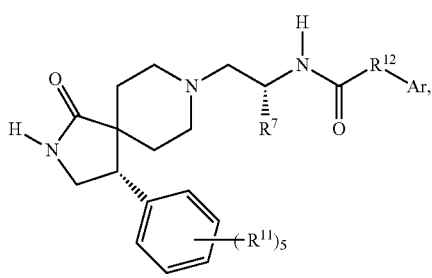

wherein $R^7$ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl.

It is understood that the disclosed compounds can be used in connection with the disclosed methods, compositions, kits, and uses.

2. $R^1$ Groups

In one aspect, $R^1$ is an optionally substituted C3 to C9 organic residue selected from aryl, heteroaryl, cycloalkyl, heterocycloalkyl, cycloalkenyl, and heterocycloalkenyl.

In a further aspect, $R^1$ is optionally substituted aryl selected from phenyl and naphthyl.

In a further aspect, $R^1$ is optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^1$ is optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^1$ is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^1$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^1$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^1$ is halophenyl, for example 4-fluorophenyl.

3. $R^2$ Groups

In one aspect, $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^2$ is hydrogen. In a further aspect, each $R^2$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^2$ is independently selected from halide, hydroxyl, trifluoromethyl, amino, cyano, nitro, azide, carboxamido, alkoxy, thiol, and alkylsulfonyl. In a further aspect, at least one $R^2$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

4. $R^3$ Groups

In one aspect, $R^3$ comprises hydrogen, an optionally substituted C1 to C6 alkyl, an optionally substituted C3 to C6 cycloalkyl, or a hydrolysable residue. In a further aspect, $R^3$ is hydrogen. In a further aspect, $R^3$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^3$ is an optionally substituted C3 to C6 cycloalkyl selected from cyclopropyl, cyclobutyl, cyclopentyl, cyclohexyl, and bicyclo[3.1.0]hexyl. In a further aspect, $R^3$ is a hydrolysable residue.

5. $R^4$ Groups

In one aspect, $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^4$ is hydrogen. In a further aspect, each $R^4$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^4$ is independently selected from halide, hydroxyl, trifluoromethyl, amino, cyano, nitro, azide, carboxamido, alkoxy, thiol, and alkylsulfonyl. In a further aspect, at least one $R^4$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

6. $R^5$ Groups

In one aspect, $R^5$ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl. In a further aspect, $R^5$ is hydrogen. In a further aspect, $R^5$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^5$ is selected from halide, hydroxyl, trifluoromethyl, amino, cyano, nitro, azide, carboxamido, alkoxy, thiol, and alkylsulfonyl. In a further aspect, $R^5$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

7. $R^6$ Groups

In one aspect, $R^6$ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl. In a further aspect, $R^6$ is hydrogen. In a further aspect, $R^6$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^6$ is selected from halide, hydroxyl, trifluoromethyl, amino, cyano, nitro, azide, carboxamido, alkoxy, thiol, and alkylsulfonyl. In a further aspect, $R^6$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^6$ is hydrogen and wherein $R^5$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^6$ is hydrogen and wherein $R^5$ is selected from halide, hydroxyl, trifluoromethyl, amino, cyano, nitro, azide, carboxamido, alkoxy, thiol, and alkylsulfonyl. In a further aspect, $R^6$ is hydrogen and wherein $R^5$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^5$ is hydrogen and wherein $R^6$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^5$ is hydrogen and wherein $R^6$ is selected from halide, hydroxyl, trifluoromethyl, amino, cyano, nitro, azide, carboxamido, alkoxy, thiol, and alkylsulfonyl. In a further aspect, $R^5$ is hydrogen and wherein $R^6$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^5$ and $R^6$, together with the intermediate carbon, comprise an optionally substituted C3 to C6 cycloalkyl. In a further aspect, wherein $R^5$ and $R^6$, together with the intermediate carbon, comprise cyclopropyl, cyclobutyl, cyclopentyl, or cyclohexyl.

8. $R^7$ Groups

In one aspect, $R^7$ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl. In a further aspect, $R^7$ is hydrogen. In a further aspect, $R^7$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^7$ is selected from halide, hydroxyl, trifluoromethyl, amino, cyano, nitro, azide, carboxamido, alkoxy, thiol, and alkylsulfonyl. In a further aspect, $R^7$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^7$ is methyl.

9. $R^8$ Groups

In one aspect, $R^8$ comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl. In a further aspect, $R^8$ is hydrogen. In a further aspect, $R^8$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^8$ is selected from halide, hydroxyl, trifluoromethyl, amino, cyano, nitro, azide, carboxamido, alkoxy, thiol, and alkylsulfonyl. In a further aspect, $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^8$ is methyl.

In a further aspect, $R^8$ is hydrogen and wherein $R^7$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^8$ is hydrogen and wherein $R^7$ is selected from halide, hydroxyl, trifluoromethyl, amino, cyano, nitro, azide, carboxamido, alkoxy, thiol, and alkylsulfonyl. In a further aspect, $R^8$ is hydrogen and wherein $R^7$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^7$ is hydrogen and wherein $R^8$ is selected from halide, hydroxyl, trifluoromethyl, amino, cyano, nitro, azide, carboxamido, alkoxy, thiol, alkylsulfonyl, and an optionally substituted C1 to C6 organic residue. In a further aspect, $R^7$ is hydrogen and wherein $R^8$ is selected from halide, hydroxyl, trifluoromethyl, amino, cyano, nitro, azide, carboxamido, alkoxy, thiol, and alkylsulfonyl. In a further aspect, $R^7$ is hydrogen and wherein $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^7$ and $R^8$, together with the intermediate carbon, comprise an optionally substituted C3 to C6 cycloalkyl. In a further aspect, $R^7$ and $R^8$, together with the intermediate carbon, comprise cyclopropyl, cyclobutyl, cyclopentyl, or cyclohexyl.

10. $R^9$ Groups

In one aspect, $R^9$ comprises hydrogen, an optionally substituted C1 to C6 alkyl, an optionally substituted C3 to C6 cycloalkyl, or a hydrolysable residue. In a further aspect, $R^9$ is hydrogen. In a further aspect, $R^9$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^9$ is an optionally substituted C3 to C6 cycloalkyl selected from cyclopropyl, cyclobutyl, cyclopentyl, and cyclohexyl. In a further aspect, $R^9$ is a hydrolysable residue.

11. $R^{10}$ Groups

In one aspect, $R^{10}$ comprises an optionally substituted C1 to C12 organic residue selected from alkyl, aryl, heteroaryl, cycloalkyl, heterocycloalkyl, cycloalkenyl, and heterocycloalkenyl. In a further aspect, $R^{10}$ is an optionally substituted alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, cyclohexyl, heptyl, cycloheptyl, octyl, cyclooctyl, nonyl, cyclononyl, decyl, cyclodecyl, undecyl, cycloundecyl, dodecyl, or cyclododecyl.

In a further aspect, $R^{10}$ is an optionally substituted aryl selected from phenyl and naphthyl.

In a further aspect, $R^{10}$ is an optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^{10}$ is an optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^{10}$ is an optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{10}$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^{10}$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{10}$ is phenylethynyl, indolyl, quinolinyl, naphthyl, phenylcyclopropyl, or fluorophenyl.

12. $R^{11}$ Groups

In one aspect, $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue, for example, methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In various aspects, from 1 to 5 $R^{11}$ groups are present in a disclosed compound. For example, 1, 2, 3, 4, 5, or 6 $R^{11}$ groups can be present. In a further aspect, no more than two R11 non-hydrogen substituents are present. In a further aspect, only one $R^{11}$ substituents is present. In a further aspect, no $R^{11}$ groups are present.

13. $R^{12}$ Groups

In one aspect, $R^{12}$ is a covalent bond, a C1 to C3 alkyl, for example, methyl, ethyl, ethenyl, ethynyl, n-propyl, or i-propyl, or a C1 to C3 cycloalkyl, for example, cyclopropyl, imidazole, 1,3-dioxolane, or 1,3,5-triazine. In a further aspect, $R^{12}$ has a structure:

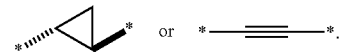

14. Ar Groups

In one aspect, Ar is an optionally substituted C4 to C10 organic residue selected from aryl and heteroaryl. In a further aspect, Ar is phenyl, indolyl, quinolinyl, naphthyl, or fluorophenyl.

15. Y Groups

In one aspect, each of $Y^1, Y^2, Y^3, Y^4$, and $Y^5$ independently comprises N or C—$R^{11}$. In various aspects, 1, 2, 3, 4, or 5 Y groups can be N. In a further aspect, no more than two of $Y^1, Y^2, Y^3, Y^4$, and $Y^5$ are N. In a further aspect, only one of $Y^1, Y^2, Y^3, Y^4$, and $Y^5$ is N. In a further aspect, each of $Y^1, Y^2, Y^3, Y^4$, and $Y^5$ independently comprises C—$R^{11}$. In a further aspect, each of $Y^1, Y^2, Y^3, Y^4$, and $Y^5$ independently comprises C—$R^{11}$ and wherein no more than two $R^{11}$ non-hydrogen substituents are present. In a further aspect, each of $Y^1, Y^2, Y^3, Y^4$, and $Y^5$ independently comprises C—$R^{11}$ and wherein only one $R^{11}$ non-hydrogen substituent is present.

16. Exemplary Compounds

In various aspects, a compound can be present as:

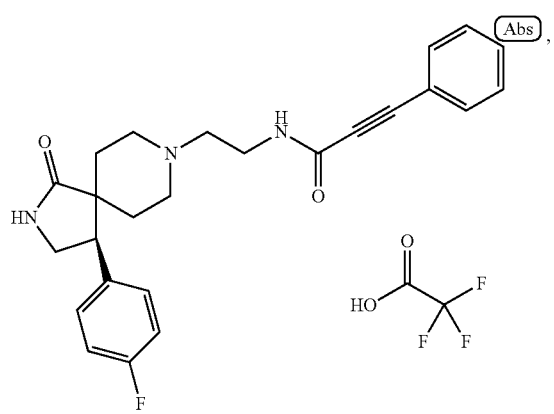

45
-continued
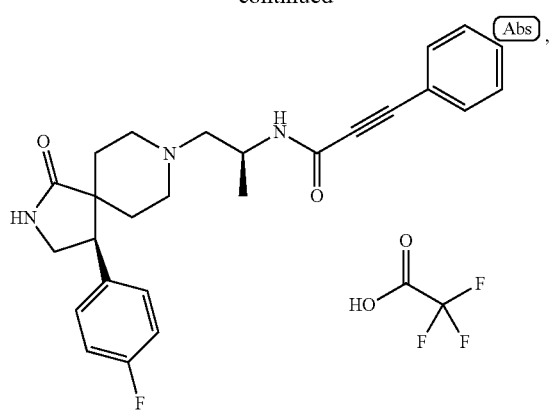
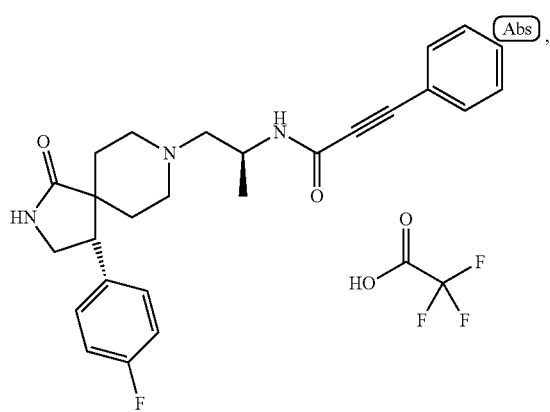
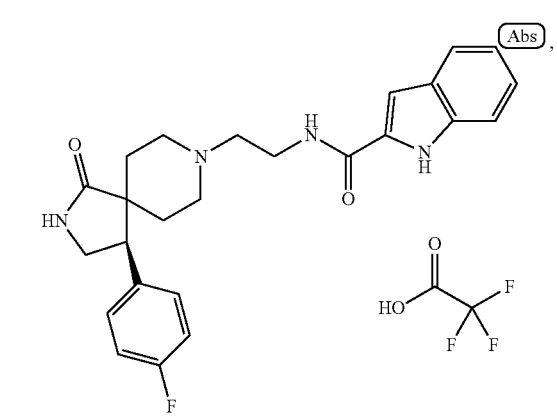
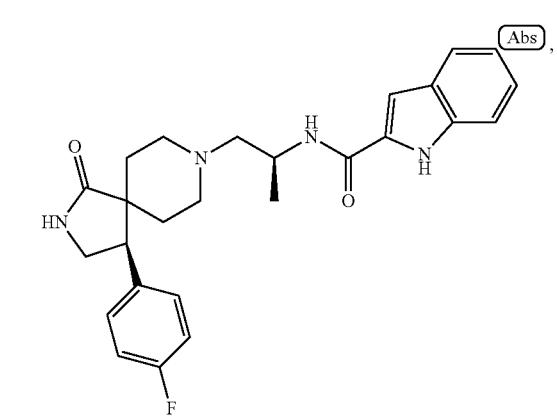
46
-continued
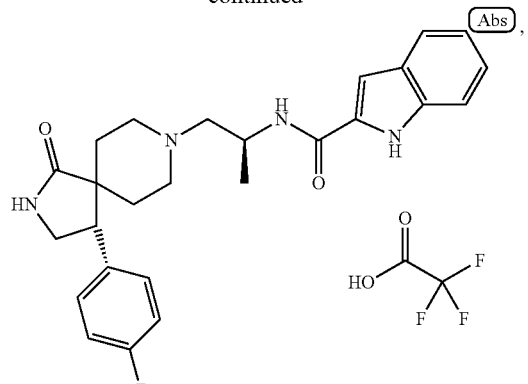
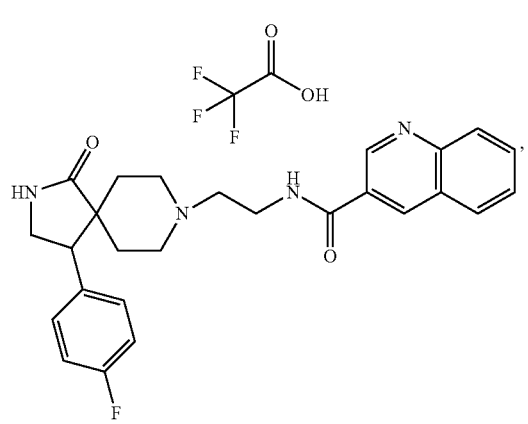
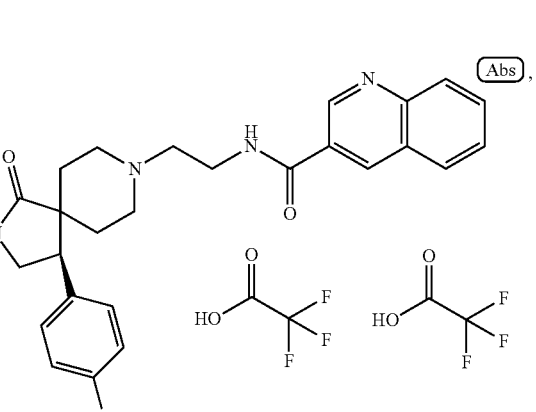
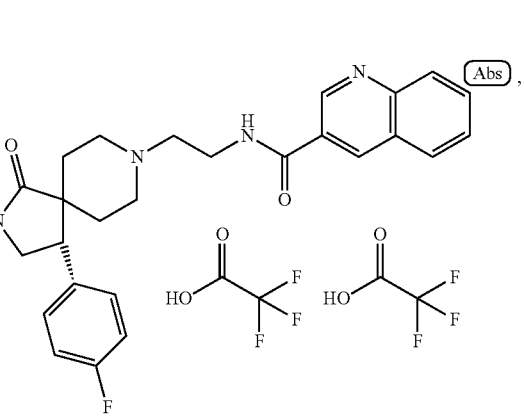

-continued
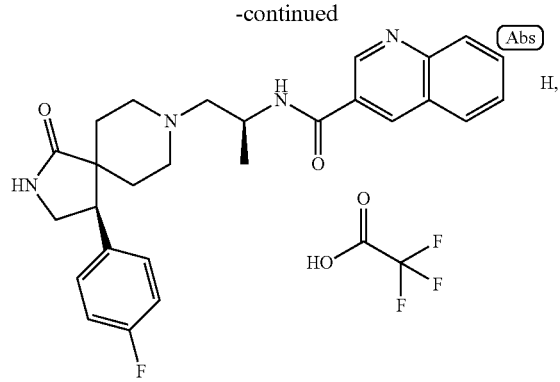
H,
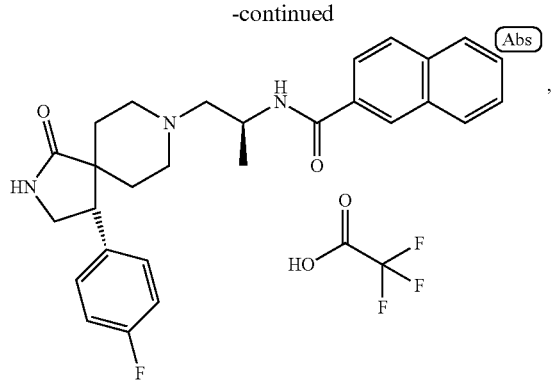
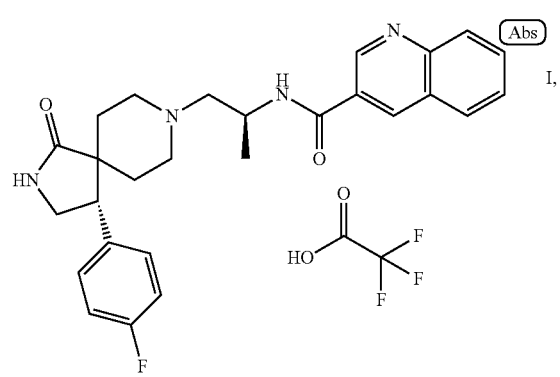
I,
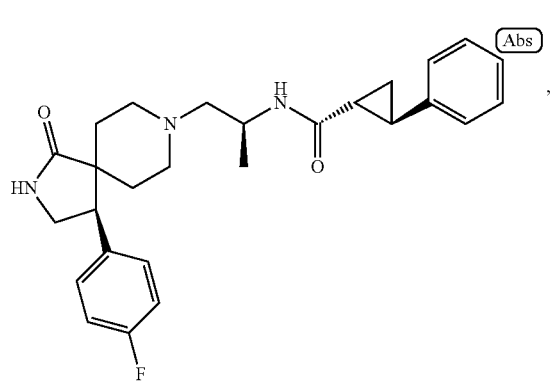
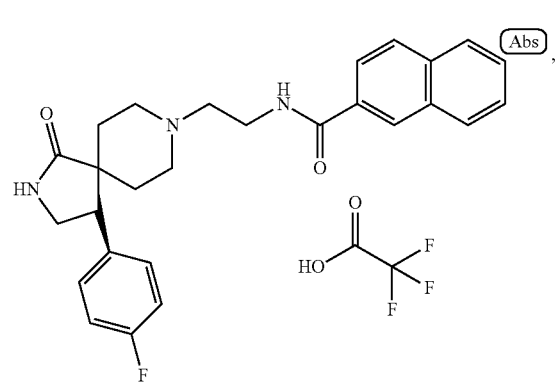
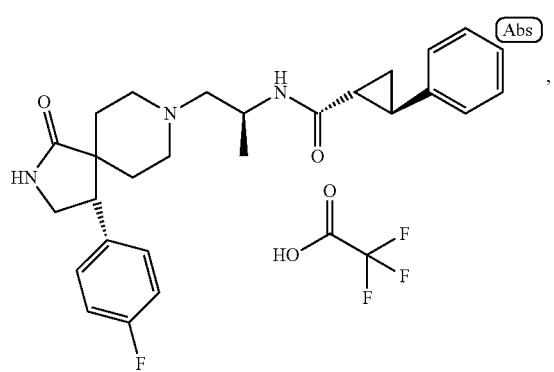
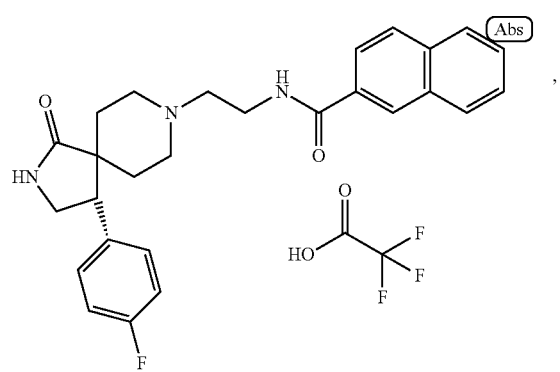

-continued

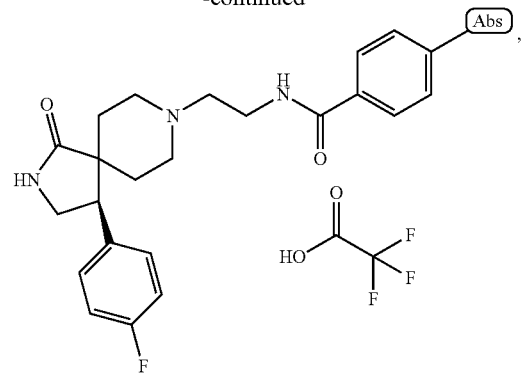

, or

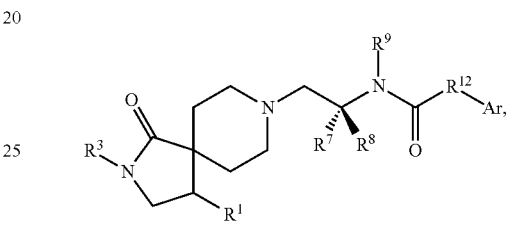

.

17. Inhibition Activity

In one aspect, the compound inhibits PLD activity; that is, a compound can inhibit PLD1 activity and/or PLD2 activity. In a further aspect, the compound inhibits PLD1 response in Calu-1 cells. In a further aspect, the compound inhibits PLD2 response in HEK293gfpPLD2 cells. In a further aspect, the compound inhibits in vitro PLD1 response. In a further aspect, the compound inhibits in vitro PLD2 response. For example, the compound can have a PLD1 $IC_{50}$ of less than about 10 μM, of less than about 5 μM, of less than about 1 μM, of less than about 500 nM, of less than about 100 nM, or of less than about 50 nM. As further examples, the compound can have a PLD2 $IC_{50}$ of less than about 10 μM, of less than about 5 μM, of less than about 1 μM, of less than about 500 nM, of less than about 100 nM, or of less than about 50 nM.

In a further aspect, the compound can have a PLD1 $IC_{50}$ of less than about 10 μM, of less than about 1 μM, of less than about 500 nM, of less than about 100 nM, of less than about 60 nM, or of less than about 20 nM. In a further aspect, the compound can have a PLD2 $IC_{50}$ of less than about 10 μM, of less than about 1 μM, of less than about 500 nM, of less than about 100 nM, of less than about 60 nM, or of less than about 20 nM.

In one aspect, a compound has a structure represented by a formula:

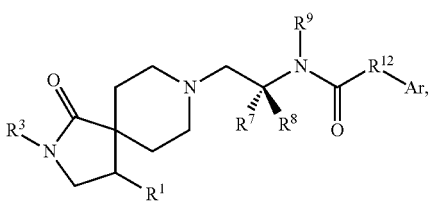

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{12}$ is a covalent bond, a C1 to C3 alkyl, or a C1 to C3 cycloalkyl; and wherein Ar is an optionally substituted C4 to C10 organic residue selected from aryl and heteroaryl, and wherein the compound inhibits PLD1 response, having an $IC_{50}$ of less than about 10 μM.

In a further aspect, a compound has a structure represented by a formula:

wherein $R^1$ is an optionally substituted C3 to C9 organic residue selected from aryl, heteroaryl, cycloalkyl, heterocycloalkyl, cycloalkenyl, and heterocycloalkenyl; wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹² is a covalent bond, a C1 to C3 alkyl, or a C1 to C3 cycloalkyl; and wherein Ar is an optionally substituted C4 to C10 organic residue selected from aryl and heteroaryl, and wherein the compound inhibits PLD2 response, having an IC₅₀ of less than about 10 μM.

18. Enantiomer-Dependent Differential PLD Inhibition

In one aspect, the R-enantiomer of a disclosed compound inhibits PLD activity more potently than the corresponding S-enantiomer. For example, a particular R-enantiomer of a disclosed compound can have an IC₅₀ for PLD1 and/or PLD2 of less than about 10 μM, of less than about 5 μM, of less than about 1 μM, of less than about 500 nM, of less than about 100 nM, or of less than about 50 nM, while the corresponding S-enantiomer of the disclosed compound has an IC₅₀ of >10 μM.

In a further aspect, the S-enantiomer of a disclosed compound inhibits PLD activity more potently than the corresponding R-enantiomer. For example, a particular S-enantiomer of a disclosed compound can have an IC₅₀ for PLD1 and/or PLD2 of less than about 10 μM, of less than about 5 μM, of less than about 1 μM, of less than about 500 nM, of less than about 100 nM, or of less than about 50 nM, while the corresponding R-enantiomer of the disclosed compound has an IC₅₀ of >10 μM.

In a further aspect, the compound exhibits a PLD1:PLD2 inhibition ratio of at least about 2:1, of at least about 3:1, of at least about 5:1, of at least about 10:1, of at least about 20:1, of at least about 50:1, or of at least about 75:1. In a further aspect, the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In one aspect, a compound has a structure represented by a formula:

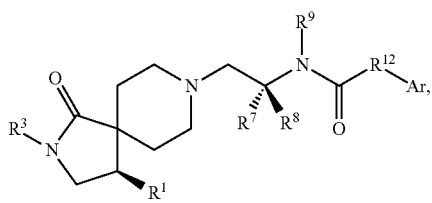

wherein R¹ is an optionally substituted C3 to C9 organic residue selected from aryl, heteroaryl, cycloalkyl, heterocycloalkyl, cycloalkenyl, and heterocycloalkenyl; wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹² is a covalent bond, a C1 to C3 alkyl, or a C1 to C3 cycloalkyl; wherein Ar is an optionally substituted C4 to C10 organic residue selected from aryl and heteroaryl, and wherein the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, a compound has a structure represented by a formula:

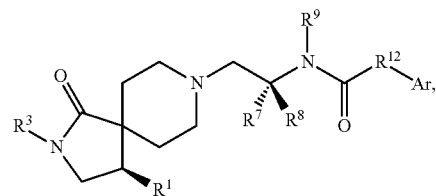

wherein R¹ is an optionally substituted C3 to C9 organic residue selected from aryl, heteroaryl, cycloalkyl, heterocycloalkyl, cycloalkenyl, and heterocycloalkenyl; wherein R³ comprises hydrogen, an optionally substituted C1 to C6 alkyl, an optionally substituted C3 to C6 cycloalkyl, or a hydrolysable residue; wherein each of R⁷ and R⁸ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹² is a covalent bond, a C1 to C3 alkyl, or a C1 to C3 cycloalkyl; wherein Ar is an optionally substituted C4 to C10 organic residue selected from aryl and heteroaryl, and wherein the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, a compound has a structure represented by a formula:

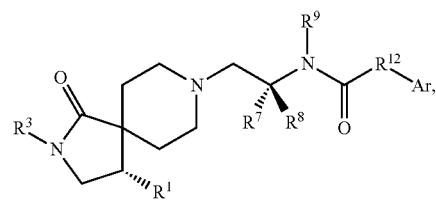

wherein R¹ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{13}$ is a covalent bond, a C1 to C3 alkyl, or a C1 to C3 cycloalkyl; wherein Ar is an optionally substituted C4 to C10 organic residue selected from aryl and heteroaryl, and wherein the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, a compound has a structure represented by a formula:

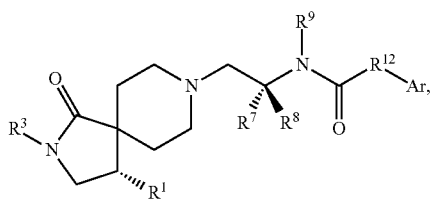

wherein $R^1$ is an optionally substituted C3 to C9 organic residue selected from aryl, heteroaryl, cycloalkyl, heterocycloalkyl, cycloalkenyl, and heterocycloalkenyl; wherein $R^3$ comprises hydrogen, an optionally substituted C1 to C6 alkyl, an optionally substituted C3 to C6 cycloalkyl, or a hydrolysable residue; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{12}$ is a covalent bond, a C1 to C3 alkyl, or a C1 to C3 cycloalkyl; wherein Ar is an optionally substituted C4 to C10 organic residue selected from aryl and heteroaryl, and wherein the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

While the disclosed compounds can be provided as a mixture of both the R-enantiomer and the S-enantiomer, it can be desired to provide the mixture of enantiomers of a disclosed compound enriched in the more potent compound. Such can be desired in order to, for example, increase the concentration of an active (or more active) enantiomer or in order to decrease the concentration of a less active (or inactive) enantiomer. Such can improve potency of a pharmaceutical preparation. Such also can minimize undesired side-effects present in a less active enantiomer and not present (or less present) in a more active enantiomer. Additionally, selection of a particular enantiomer can facilitate targeting PLD1 over PLD2 or PLD2 over PLD1.

Thus, in various aspects, a disclosed compound can be provided in a form enriched in R-enantiomer of the compound. For example, a disclosed compound can be provided in an enantiomeric excess of greater than 50%, greater than 60%, greater than 70%, greater than 75%, greater than 80%, greater than 85%, greater than 90%, greater than 95%, greater than 98%, or greater than 99% of the R-enantiomer of the compound. In one aspect, the R-enantiomer is substantially free from the S-enantiomer. For example, the "R" forms of the compounds can be provided substantially free from the "S" forms of the compounds.

TABLE 1

| | | Cellular CRCs | | | Exogenous CRCs | |
| --- | --- | --- | --- | --- | --- | --- |
| Name | Structure | Calu-1 $IC_{50}$ nM | 293-PLD2 $IC_{50}$ nM | Fold Selective | PLD1 $IC_{50}$ nM | PLD2 $IC_{50}$ nM |
| P0Q | | 1,200 | 70 | 17-fold PLD2 | | |

TABLE 1-continued
PLD INHIBITOR CONCENTRATION RESPONSE CURVES
| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| NGF | 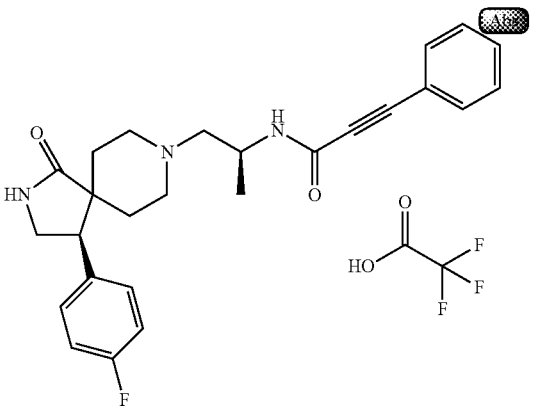 [SMILES: C[C@@H](CN1CCC2(CC1)C(=O)NC[C@@H]2c1ccc(F)cc1)NC(=O)C#Cc1ccccc1 ; O=C(O)C(F)(F)F] | 16 | 150 | | | |
| NJ5 | 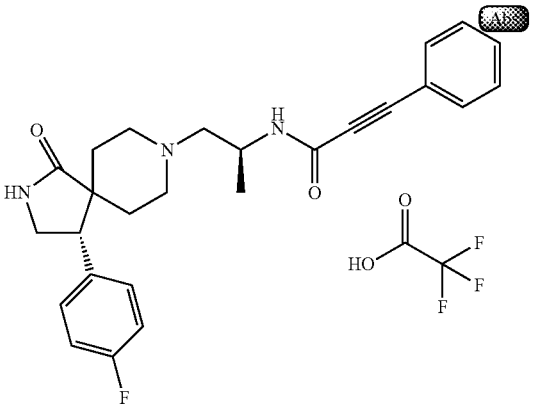 [SMILES: C[C@@H](CN1CCC2(CC1)C(=O)NC[C@H]2c1ccc(F)cc1)NC(=O)C#Cc1ccccc1 ; O=C(O)C(F)(F)F] | 320 | 4,000 | | | |
| P23 | 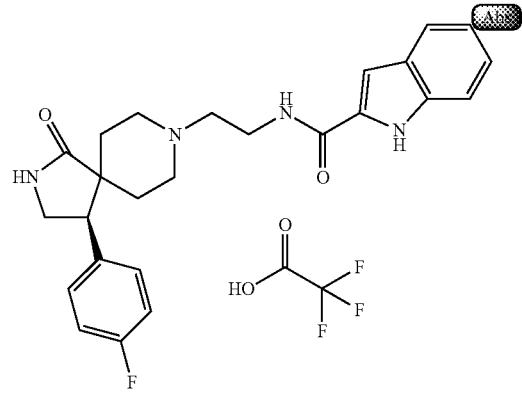 [SMILES: O=C(NCCN1CCC2(CC1)C(=O)NC[C@@H]2c1ccc(F)cc1)c1cc2ccccc2[nH]1 ; O=C(O)C(F)(F)F] | 21 | 2.5 | 8 fold PLD2 | | |

TABLE 1-continued

PLD INHIBITOR CONCENTRATION RESPONSE CURVES

| Name | Structure | Cellular CRCs | | | Exogenous CRCs | |
|---|---|---|---|---|---|---|
| | | Calu-1 IC$_{50}$ nM | 293-PLD2 IC$_{50}$ nM | Fold Selective | PLD1 IC$_{50}$ nM | PLD2 IC$_{50}$ nM |
| P1G | | 1 | 12 | | | |
| NG3 | | 16 | 140 | | | |
| CTH Racemic mixture | | 2,400 | 145 | 17-fold PLD2 | 1,970 | 450 |

TABLE 1-continued

PLD INHIBITOR CONCENTRATION RESPONSE CURVES

| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| P1P | | 1,350 | 60 | 23-fold PLD2 | >20,000 | 5,050 |
| NFT | | 12,000 | 450 | 27-fold PLDS | >20,000 | 5,050 |
| P0L | | 25 | 115 | | 100 | 725 |

TABLE 1-continued

PLD INHIBITOR CONCENTRATION RESPONSE CURVES

| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| P2E | | 200 | 700 | | 5,130 | 6,750 |
| P22 | | 820 | 26 | 32-fold PLD2 | 3,900 | 73 |
| P1D | | 3,700 | 220 | 17-Fol PLD2 | | |
| P1Q | | 93 | 540 | | | |

TABLE 1-continued

PLD INHIBITOR CONCENTRATION RESPONSE CURVES

| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| P1E | | 6,100 | 760 | 8-fold PLD2 | | |
| P0A | | 600 | 14,000 | | | |
| NGQ | | 3,000 | >20,000 | | | |

TABLE 1-continued

PLD INHIBITOR CONCENTRATION RESPONSE CURVES

| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| NFW | | 5,500 | 220 | 25 Fold PLD2 | 11,000 | 480 |
| P2C | | >20,000 | 3,175 | ~10-fold? | >20,000 | >20,000 |
| NGH | | 250 | 210 | | 1,200 | 2,240 |

TABLE 1-continued

PLD INHIBITOR CONCENTRATION RESPONSE CURVES

| | | Cellular CRCs | | | Exogenous CRCs | |
|---|---|---|---|---|---|---|
| Name | Structure | Calu-1 IC$_{50}$ nM | 293-PLD2 IC$_{50}$ nM | Fold Selective | PLD1 IC$_{50}$ nM | PLD2 IC$_{50}$ nM |
| P2B | 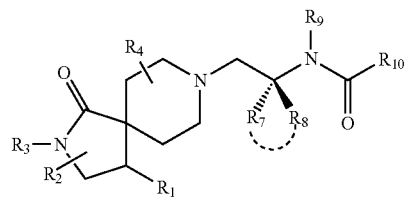 | 1,700 | 2,800 | | 5,150 | 9,440 |

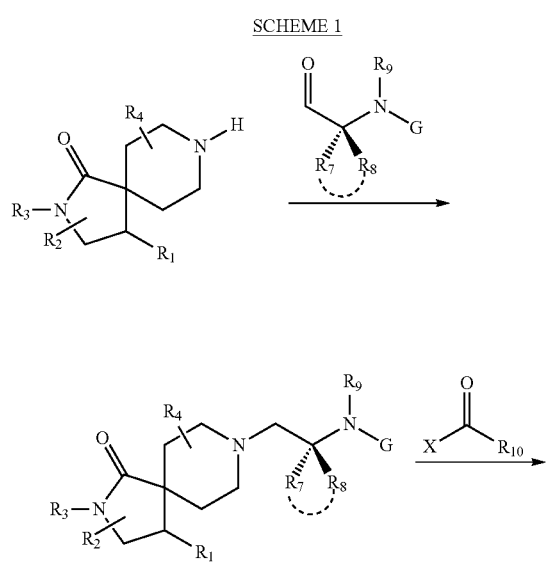

C. METHODS OF MAKING THE COMPOUNDS

In one aspect, the invention relates to methods of making compounds useful as isoform selective Phospholipase D inhibitors, which can be useful in the treatment disorder associated with PLD activity. The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein.

An exemplary synthetic route is shown in Scheme 1 below:

Generally, the method can comprise one or both of two chemical transformations. The first transformation involves a reaction between an amine functionality and a carbonyl functionality in a reductive amination reaction. The product of this reaction can, thus, be an amine, which can be isolated or carried into another chemical transformation in unisolated form. In one aspect, G can be a protecting group, which can be removed subsequent to this reaction as well as before, or concurrently with, further reaction.

Both the starting amino compound and the carbonyl compound can be prepared or obtained commercially. A stereocenter is present in the amino compound. A particular steroisomer can be obtained during preparation of the amino compound by, for example, chiral separation. One or more stereocenters are present in the product of the reaction. A particular steroisomer of the product can be obtained by, for example, chiral separation of a racemic mixture of stereoisomers.

The second transformation involves a reaction between the deprotected amine functionality and an activated carboxyl functionality, yielding an amide.

Thus, in one aspect, the invention relates to a method for preparing a compound comprising the steps of providing a compound having a structure:

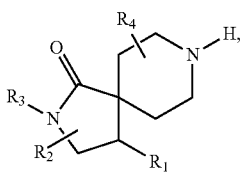

wherein R[1] is an optionally substituted C3 to C9 organic residue selected from aryl, heteroaryl, cycloalkyl, heterocycloalkyl, cycloalkenyl, and heterocycloalkenyl; wherein R[2] comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R[3] comprises hydrogen, an optionally substituted C1 to C6 alkyl, an optionally substituted C3 to C6 cycloalkyl, or a hydrolysable residue; and wherein R[4] comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and reacting with a compound having a structure:

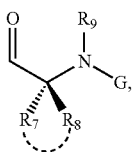

wherein each of R[7] and R[8] independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or R[7] and R[8], together with the intermediate carbon, comprise an optionally substituted C3 to C6 cycloalkyl; wherein R[9] comprises hydrogen, an optionally substituted C1 to C6 alkyl, an optionally substituted C3 to C6 cycloalkyl, or a hydrolysable residue, and wherein G is a protecting group.

In a further aspect, providing is chiral separation. In a further aspect, the method further comprises the step of reacting with a compound having a structure:

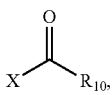

wherein R[10] comprises an optionally substituted C1 to C12 organic residue selected from alkyl, aryl, heteroaryl, cycloalkyl, heterocycloalkyl, cycloalkenyl, and heterocycloalkenyl, and wherein X is a leaving group. In a further aspect, G is tert-butyloxycarbonyl.

An alternative synthetic route is shown in Scheme 2 below:

SCHEME 2

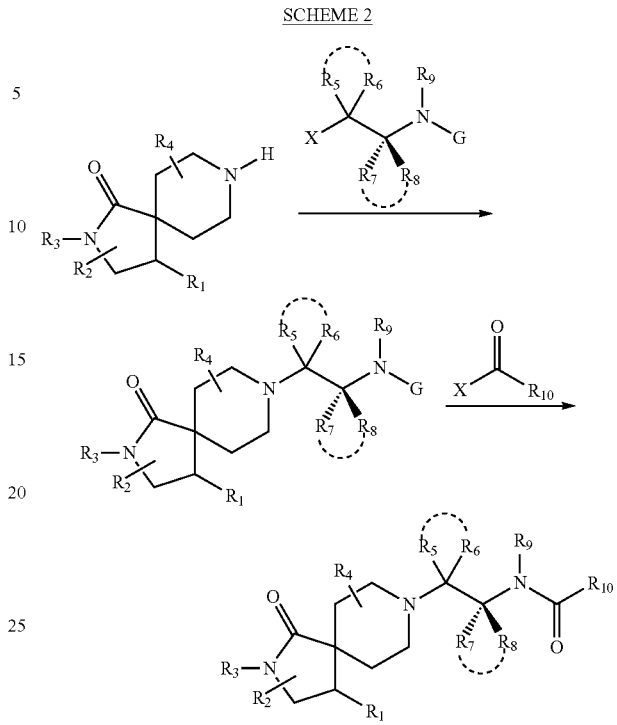

Generally, the method can comprise one or both of two chemical transformations. The first transformation involves a reaction between an amine functionality and an electrophilic alkyl functionality in a nucleophilic substitution reaction. The product of this reaction can, thus, be an amine, which can be isolated or carried into another chemical transformation in unisolated form. In one aspect, G can be a protecting group, which can be removed subsequent to this reaction as well as before, or concurrently with, further reaction.

Both the starting amino compound and the electrophilic alkyl compound can be prepared or obtained commercially. A stereocenter is present in the amino compound. A particular steroisomer can be obtained during preparation of the amino compound by, for example, chiral separation. One or more stereocenters are present in the product of the reaction. A particular steroisomer of the product can be obtained by, for example, chiral separation of a racemic mixture of stereoisomers.

The second transformation involves a reaction between the deprotected amine functionality and an activated carboxyl functionality, yielding an amide.

Thus, in a further aspect, the method comprises the steps of providing a compound having a structure:

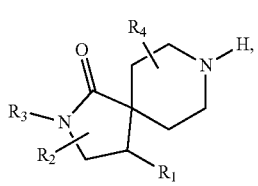

wherein R[1] is an optionally substituted C3 to C9 organic residue selected from aryl, heteroaryl, cycloalkyl, heterocycloalkyl, cycloalkenyl, and heterocycloalkenyl; wherein R[2] comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and reacting with a compound having a structure:

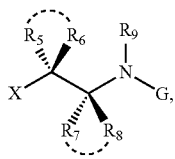

wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^1$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue, wherein G is a protecting group, and wherein X is a leaving group.

In a further aspect, providing is chiral separation.

In a further aspect, the method further comprises the step of reacting with a compound having a structure:

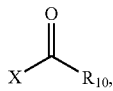

wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, and wherein X is a leaving group. In a further aspect, G is tert-butyloxycarbonyl.

In a further aspect, the method comprises the steps of providing a compound having a structure:

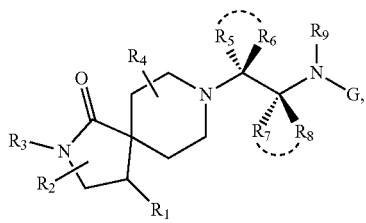

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; and wherein G is a protecting group, and reacting with a compound having a structure:

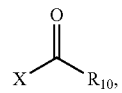

wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, and wherein X is a leaving group.

In a further aspect, providing is reacting a compound having a structure:

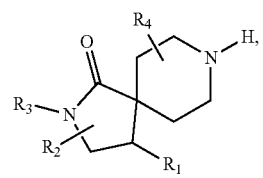

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and with a compound having a structure:

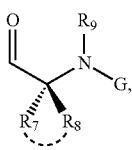

wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue, and wherein G is a protecting group.

In a further aspect, providing is reacting a compound having a structure:

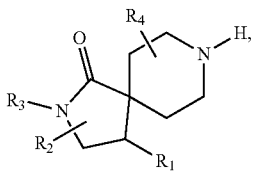

wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, with a compound having a structure:

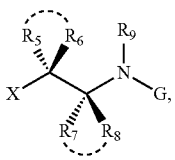

wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue, wherein G is a protecting group, and wherein X is a leaving group. In a further aspect, the method further comprises the step of chiral separation. In a further aspect, G is tert-butyloxycarbonyl.

It is understood that the disclosed methods can be used in connection with the disclosed compounds, compositions, kits, and uses.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable derivatives (e.g., salt(s)) thereof) as an active ingredient, a pharmaceutically acceptable carrier, and, optionally, other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The disclosed compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and can be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions encompass any composition made by admixing a compound of the present invention and a pharmaceutically acceptable carrier.

As used herein, the term "pharmaceutically acceptable salts" refers to salts prepared from pharmaceutically acceptable non-toxic bases or acids. When a disclosed compound is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable derivatives thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment of the disclosed conditions, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The disclosed pharmaceutical compositions can further comprise other therapeutically active compounds, as discussed further herein, which are usually applied in the treatment of the above mentioned pathological conditions.

Thus, in one aspect, the invention relates to a pharmaceutical composition comprising a therapeutically effective amount of a compound having a structure represented by a formula:

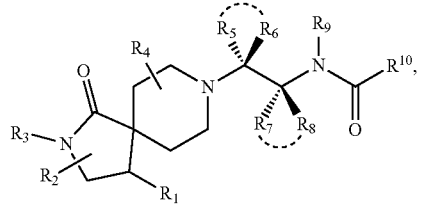

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof, and a pharmaceutically acceptable carrier.

In a further aspect, a pharmaceutical composition can comprise a therapeutically effective amount of any one or more disclosed compound and a pharmaceutically acceptable carrier. In a further aspect, a pharmaceutical composition can comprise a therapeutically effective amount of one or more product of any disclosed method and a pharmaceutically acceptable carrier. In one aspect, the invention relates to a method for manufacturing a medicament comprising combining at least one disclosed compound or at least one product of a disclosed method with a pharmaceutically acceptable carrier or diluent.

It is understood that the disclosed compositions can be prepared from the disclosed compounds. It is also understood that the disclosed compositions can be employed in the disclosed methods of using.

E. KITS

In one aspect, the invention relates to a kit comprising at least one disclosed compound or at least one product of a disclosed method and at least one agent known to increase PLD activity. In a further aspect, a kit comprises at least one disclosed compound or at least one product of a disclosed method and at least one agent known to decrease PLD activity. In a further aspect, the at least one compound or the at least one product and the at least one agent are co-formulated. In a further aspect, the at least one compound or the at least one product and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

F. METHODS OF USING COMPOUNDS, PRODUCTS, AND COMPOSITIONS

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders associated with PLD activity. Thus, in one aspect, the invention relates to a method for the treatment of a disorder associated with PLD activity in a mammal comprising the step of administering to the mammal at least one disclosed compound or at least one product of a disclosed method in a dosage and amount effective to treat the disorder in the mammal. In a further aspect, the disorder is associated with PLD activity dysfunction. In a further aspect, the PLD inhibited is PLD1. In a further aspect, the PLD inhibited is PLD2.

In a further aspect, the mammal is a human. In a further aspect, the mammal has been diagnosed with a need for treatment for the disorder prior to the administering step. In a further aspect, the method further comprises the step of identifying a mammal in need of treatment for the disorder.

In one aspect, the disorder is a disease of uncontrolled cellular proliferation. In a further aspect, the disorder is cancer. In a further aspect, the disorder is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

2. PLD Inhibition

The compounds disclosed herein are further useful for inhibiting PLD activity. Thus, in one aspect, the invention relates to a method for inhibiting PLD activity in a mammal comprising the step of administering to the subject at least one disclosed compound or at least one product of a disclosed method in a dosage and amount effective to inhibit PLD activity in the subject. In a further aspect, the PLD inhibited is PLD1. In a further aspect, the PLD inhibited is PLD2.

In a further aspect, the mammal is a human. In a further aspect, the mammal has been diagnosed with a need for PLD inhibition prior to the administering step. In a further aspect, the mammal has been diagnosed with a need for treatment of a disorder related to PLD activity prior to the administering step. In a further aspect, the method further comprises the step of identifying a mammal in need of PLD inhibition.

In a further aspect, the invention relates to a method for inhibiting PLD activity in at least one cell, comprising the step of contacting the at least one cell with at least one disclosed compound or at least one product of a disclosed method in an amount effective to inhibit PLD activity response in the at least one cell. In a further aspect, contacting is via administration to a mammal. In a further aspect, the cell is mammalian, for example, human. In a further aspect, the cell has been isolated from a mammal prior to the contacting step. In a further aspect, the PLD inhibited is PLD1. In a further aspect, the PLD inhibited is PLD2.

It is understood that the disclosed methods can be employed in connection with the disclosed compounds, methods, compositions, and kits.

G. USES

In one aspect, the invention relates to the use of a compound for PLD inhibition, the compound having a structure represented by a formula:

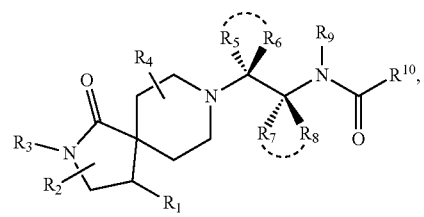

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable derivative thereof. In a further aspect, the PLD inhibited is PLD1. In a further aspect, the PLD inhibited is PLD2.

In a further aspect, the invention relates to use of at least one disclosed compound or at least one product of a disclosed method in the manufacture of a medicament for the treatment of a condition associated with PLD activity. In a further aspect, the use is in the manufacture of a medicament for the treatment of a disorder associated with PLD activity in a mammal. In a further aspect, the disorder is a disease of uncontrolled cellular proliferation. In a further aspect, the disorder is cancer. In a further aspect, the disorder is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

It is understood that the disclosed uses can be employed in connection with the disclosed compounds, methods, compositions, and kits.

In various further aspects, the invention also relates to use as therapeutic anti-cancer agent to prevent malignant migration of cancer cells to distant sites (i.e., metastasis) as well as more localized invasiveness (e.g., malignant gliomas); use for treating disorders involving signaling pathways that have been shown to be regulated by PLD, including RAS/MEK/ERK signaling cascade, NFκB, and mTOR pathways where PLD has been implicated as an essential mediator of these cell signaling and metabolic pathways; use for treating disorders involving the formation of ether-linked phospholipids where PLD plays a role in the regulated production of these molecular species. Several human cancers have been reported to result in the formation of these unusual ether-linked phospholipid species; use of PLD inhibitors in the treatment of neurological and psychiatric disorders (i.e., as outlined in the DSM IV), which can include neurodegenerative diseases; use for treating diabetes and metabolic syndrome where PLD has been associated with disorders in cellular signaling and metabolic disorders; and veterinary applications of any of the inhibitors described herein.

H. PHOSPHOLIPASE D INHIBITING ACTIVITY

The disclosed compounds and compositions can be evaluated for their ability to act as inhibitors of PLD1, PLD2, or both by any suitable known methodology known in the art. Also disclosed herein is a screening method of identifying an agent that selectively inhibits a PLD enzyme or isoenzyme. Numerous such methods are known and can be used to screen the disclosed compositions for PLD-inhibiting activity. For example, suitable screening methods are disclosed in Scott S. A., et al. Nat Chem Biol. 2009 February; 5(2):108-17; Brown, H. A., et al. Cell. 1993. 75(6):1137-44; Ivanova, P. T., et al. (2007) "Glycerophospholipid identification and quantitation by electrospray ionization mass spectrometry," In Methods in Enzymology, 432, Lipidomics and Bioactive Lipids: Mass spectrometry based lipid analysis. Edited by H. Alex Brown. Elsevier. pp. 21-57); and Brown, H. A., et al. (2007) "Biochemical Analysis of Phospholipase D." In Methods in Enzymology. 434, Lipidomics and Bioactive Lipids: Lipids and Cell Signaling. Edited by H. Alex Brown. Elsevier. pp. 49-87.

Generally, the screening method can comprise providing a sample comprising a phosholipid, a primary alcohol, and a PLD under conditions that allow the hydrolysis of the phospholipids to a phosphatidylalcohol, contacting the sample with a candidate agent, measuring enzymatic activity, comparing the enzymatic activity to a control, a decrease in enzymatic activity compared to the control identifying an agent that inhibits the PLD.

The screening method can comprise providing a sample comprising a phosholipid and a PLD under conditions that allow the hydrolysis of the phospholipids to a phosphatidic acid, contacting the sample with a candidate agent, measuring enzymatic activity, comparing the enzymatic activity to a control, a decrease in enzymatic activity compared to the control identifying an agent that inhibits the PLD.

In some aspects, the PLD is a myr-Aff-1-stimulated mammalian human PLD1 or human PLD2.

The screening method can comprise providing a cell selectively expressing a PLD isoenzyme, comprising a phosholipid, contacting the cell with a candidate agent in the presence of a primary alcohol, measuring the levels of phosphatidylalcohol in the cell, comparing the phosphatidylalcohol levels to a control, a decrease in phosphatidylalcohol levels compared to the control identifying an agent that inhibits the PLD isoenzyme.

In some aspects PLD activity in the cell is mediated predominately by PLD1. Thus, in some aspects, the cell is the human non-small-cell lung cancer (NSCLC) cell line Calu-1. In some aspects, the cell has been stimulated to activate PLD1 in the cell. For example, the cell can be stimulated with phorbol 12-myristate 13-acetate (PMA).

In some aspects PLD activity in the cell is mediated predominately by PLD2. Thus, in some aspects, the cell stably overexpresses recombinant PLD2. For example, the cell can be a HEK293 cell stably overexpressing green florescent protein (GFP)-tagged PLD2.

In some aspects, the primary alcohol of the disclosed methods is methanol, ethanol, propanol, butanol, pentanol, or octanol.

In some aspects, the primary alcohol of the disclosed methods is deuterated such that the resulting phosphatidylalcohol will be deuterated to facilitate detection. Thus, in some aspects, the primary alcohol is methanol-$d_4$, ethanol-$d_6$, propanol-$d_8$, or butanol-$d_{10}$. Other such deuterated primary alcohols are known and can be used herein. Thus, wherein the primary alcohol is butanol-$d_{10}$, the phosphatidylalcohol can be phosphatidylbutanol-$d_9$.

Enzymatic activity can be measured using standard enzyme assays known in the art. Enzyme assays generally measure either the consumption of substrate or production of product over time. A large number of different methods of measuring the concentrations of substrates and products exist and many enzymes can be assayed in several different ways.

Enzyme assays can be split into two groups according to their sampling method: continuous assays, where the assay gives a continuous reading of activity, and discontinuous assays, where samples are taken, the reaction stopped and then the concentration of substrates/products determined. Continuous assays are most convenient, with one assay giving the rate of reaction with no further work necessary. There are many different types of continuous assays, including spectrophotometric assays, fluorometric assays, calorimetric assays, chemiluminescence assays, and light scattering assays.

In spectrophotometric assays, you follow the course of the reaction by measuring a change in how much light the assay solution absorbs. If this light is in the visible region you can actually see a change in the color of the assay, these are called colorimetric assays. The MTT assay, a redox assay using a tetrazolium dye as substrate is an example of a colorimetric assay. UV light is often used, since the common coenzymes NADH and NADPH absorb UV light in their reduced forms, but do not in their oxidized forms. An oxidoreductase using NADH as a substrate could therefore be assayed by following the decrease in UV absorbance at a wavelength of 340 nm as it consumes the coenzyme.

Fluorometric assays use a difference in the fluorescence of substrate from product to measure the enzyme reaction. These assays are in general much more sensitive than spectrophotometric assays, but can suffer from interference caused by impurities and the instability of many fluorescent compounds when exposed to light.

Calorimetry is the measurement of the heat released or absorbed by chemical reactions. These assays are very general, since many reactions involve some change in heat and with use of a microcalorimeter, not much enzyme or substrate is required. These assays can be used to measure reactions that are impossible to assay in any other way.[5]

Chemiluminescence is the emission of light by a chemical reaction. Some enzyme reactions produce light and this can be measured to detect product formation. These types of assay can be extremely sensitive, since the light produced can be captured by photographic film over days or weeks, but can be hard to quantify, because not all the light released by a reaction will be detected.

Static Light Scattering measures the product of weight-averaged molar mass and concentration of macromolecules in solution. Given a fixed total concentration of one or more species over the measurement time, the scattering signal is a direct measure of the weight-averaged molar mass of the solution, which will vary as complexes form or dissociate. Hence the measurement quantifies the stoichiometry of the complexes as well as kinetics. Light scattering assays of protein kinetics is a very general technique that does not require an enzyme.

Discontinuous assays are when samples are taken from an enzyme reaction at intervals and the amount of product production or substrate consumption is measured in these samples. For example, radiometric assays measure the incorporation of radioactivity into substrates or its release from substrates. The radioactive isotopes most frequently used in these assays are $^{14}C$, $^{32}P$, $^{35}S$ and $^{125}I$. Since radioactive isotopes can allow the specific labeling of a single atom of a substrate, these assays are both extremely sensitive and specific. They are frequently used in biochemistry and are often the only way of measuring a specific reaction in crude extracts.

Chromatographic assays measure product formation by separating the reaction mixture into its components by chromatography. This is usually done by high-performance liquid chromatography (HPLC), but can also use the simpler technique of thin layer chromatography. Although this approach can need a lot of material, its sensitivity can be increased by labelling the substrates/products with a radioactive or fluorescent tag. Assay sensitivity has also been increased by switching protocols to improved chromatographic instruments (e.g. ultra-high pressure liquid chromatography) that operate at pump pressure a few-fold higher than HPLC instruments.

I. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of disclosed herein are illustrated in the following Examples. Starting materials and the requisite intermediates are in some cases commercially available, or can be prepared according to literature procedures or as illustrated herein. All reactions were carried out under an argon atmosphere employing standard chemical techniques. Solvents for extraction, washing and chromatography were HPLC grade. All reagents were purchased from Aldrich Chemical Co. at the highest commercial quality and were used without purification. Microwave-assisted reactions were conducted using a Biotage Initiator-60. All NMR spectra were recorded on a 400 MHz Bruker AMX NMR. $^1H$ chemical shifts are reported in δ values in ppm downfield from TMS as the internal standard in DMSO. Data are reported as follows: chemical shift, multiplicity (s=singlet, d=doublet, t=triplet, q=quartet, br=broad, m=multiplet), integration, coupling constant (Hz). $^{13}C$ chemical shifts are reported in δ values in ppm with the DMSO carbon peak set to 39.5 ppm. Low resolution mass spectra were obtained on an Agilent 1200 LCMS with electrospray ionization. High resolution mass spectra were recorded on a Waters QToF-API-US plus Acquity system with electrospray ionization. Analytical thin layer chromatography was performed on 250 μM silica gel 60 $F_{254}$ plates. Merck silica gel (60, particle size 0.040-0.063 mm) was used for flash column chromatography. Analytical HPLC was performed on an Agilent 1200 analytical LCMS with UV detection at 214 nm and 254 nm along with ELSD detection. Preparative purification of library compounds was performed on a custom Agilent 1200 preparative LCMS with collection triggered by mass detection. All yields refer to analytically pure and fully characterized materials ($^1H$ NMR, $^{13}C$ NMR analytical LCMS and Hi-Res MS).

1. General Method A for Amide Bond Formation

A solution containing 0.11 mmol of the appropriate acid, 0.12 mmol of EDCI, 0.12 mmol of HOBt, 3.3 mmol of triethyl amine, and 1 mL of DCM was allowed to stir for 15 min and a solution containing 1 mL of DCM and 0.1 mmol of the appropriate amine was added. The reaction mixture was rotated over the weekend. The solvent was removed under reduced pressure and the residue was submitted to mass directed HPLC purification.

2. General Method B for Amide Bond Formation

To a solution containing 0.11 mmol of the appropriate acid chloride and 1 mL of DCM was added a solution containing 0.1 mmol of the appropriate amine and 1 mL of DCM, followed by 3.3 mmol of triethyl amine. The reaction mixture was rotated over the weekend. The solvents were removed under reduced pressure and the residue was submitted to mass directed HPLC purification.

3. Example 1

N—((S)-1-((R)-4-(4-Fluorophenyl)-1-oxo-2,8-diazaspiro[4.5]decan-8-yl)propan-2-yl)-3-phenylpropiolamide 2,2,2-trifluoroacetate a. Step A: 4-(4-Fluorophenyl)-2,8-diazaspiro[4.5]decan-1-one

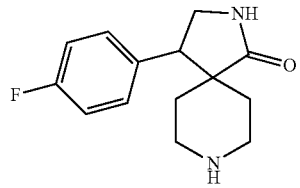 [SMILES: O=C1NCC(c2ccc(F)cc2)C12CCNCC2]

To 3.5 g (3.5 mmol) of 4-(4-fluorophenyl)-2,8-diazaspiro[4.5]decan-1-one hydrochloride was added EtOAc and 10% aqueous NaOH until dissolution occurred. The layers were separated and the aqueous layer was further extracted with ethyl acetate and DCM. The combined organic layers were dried over MgSO$_4$ and filtered. The solvents were removed under reduced pressure to give 2.75 g (90%) of 4-(4-fluorophenyl)-2,8-diazaspiro[4.5]decan-1-one as a foamy white solid: 1HNMR (400 MHz, DMSO-d6) δ ppm 7.73 (s, 1H), 7.29 (d, 1H, J=8.4 Hz), 7.28 (d, 1H, J=8.4 Hz), 7.16-7.11 (m, 2H), 3.53 (dd, 1H, J=10.4 and 7.8), 3.37-3.26 (m, 4H), 3.05-3.01 (m, 1H), 2.73-2.67 (m, 1H), 2.64-2.59 (m, 1H), 2.32-2.26 (m, 3H), and 1.52-1.43 (m, 1H); LCMS m/z: 249.2 (M+H)$^+$.

b. Step B: tert-Butyl 4-(4-fluorophenyl)-1-oxo-2,8-diazaspiro[4.5]decane-8-carboxylate

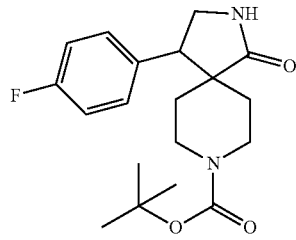 [SMILES: CC(C)(C)OC(=O)N1CCC2(CC1)C(=O)NCC2c1ccc(F)cc1]

To a solution containing 2.06 g (8.2 mmol) of the amine and 40 mL of dioxane was added 2.0 g (9.12 mmol) of BOC$_2$O followed by 1.7 mL (10.0 mmol) of DIPEA. The reaction mixture was allowed to stir at room temperature overnight. The reaction mixture was quenched by the addition of water and extracted with ethyl acetate. The combined organic extracts were washed with brine, dried over MgSO$_4$, and filtered. The solvents were removed under reduced pressure and the residue was subjected to silica gel purification to give 2.38 g (82%) of tert-butyl 4-(4-fluorophenyl)-1-oxo-2,8-diazaspiro[4.5]decane-8-carboxylate as a foamy white solid: LCMS m/z: 371.2 (M+Na)$^+$.

C. Step C: Chiral Separation

Figure 30:
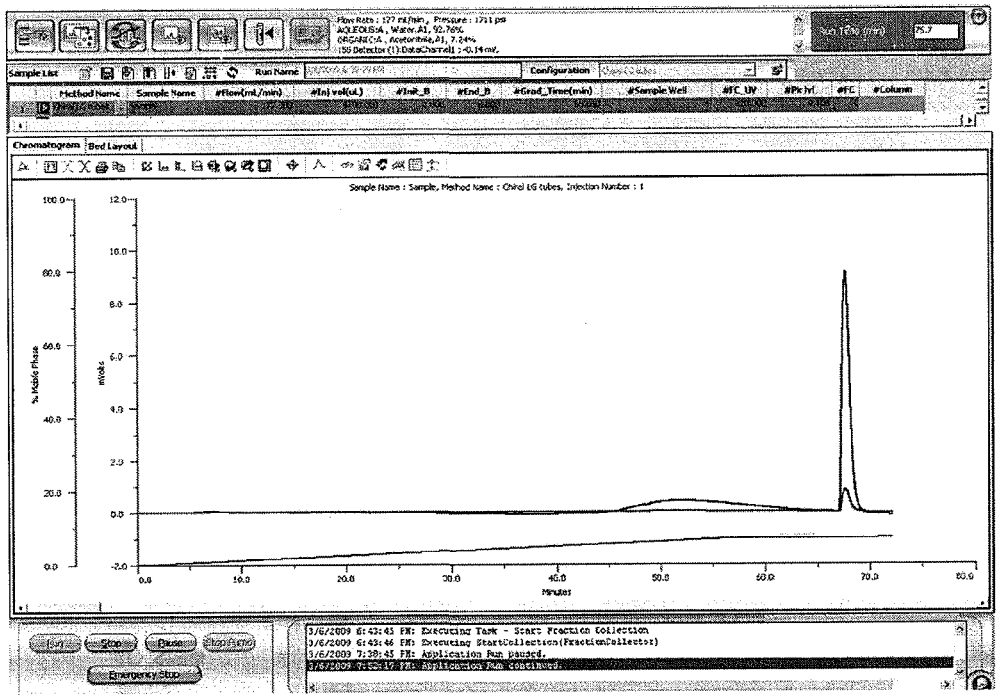
FIG. 30 shows and example chromatogram observed after chrial separation of racemate to obtain enantiompure tert-butyl 4-(4-fluorophenyl)-1-oxo-2,8-diazaspiro[4.5]decane-8-carboxylate.

Method development was conducted on an Agilent 1200 HPLC. Optimal conditions were found to be 95% Hexanes and 5% Isopropyl alcohol on a Chiraltech OJ column (10 u, 4.6×250 mm) at 1.5 ml/min. Preparative HPLC was conducted on a Gilson 215 Prep LC with pumps capable of 200 mL/min using a Chiraltech OJ 20 u, 50×250 mm. The flow rate was 177 mL/min and the peaks were collected based on a wavelength of 220 nm. The final prep conditions were altered from the analytical method due to the insoluble nature of the compound. A gradient was employed to reduce sample solvent interactions, which were responsible for poor resolution. The percentage of IPA was increased from 0% to 8% over 65 minutes. At the 62 minute mark, a 100% IPA wash allowed the sharp elution of the final peak. After rotary evaporation of the solvents, 0.99 g of each enantiomer was collected and determined to by 95% one enantiomer using the analytical method described above. An exemplary chromatogram is shown in FIG. 30.

d. Step D: (R)-4-(4-Fluorophenyl)-2,8-diazaspiro[4.5]decan-1-one

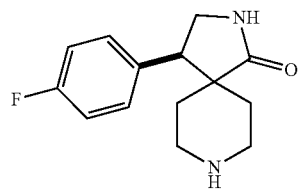

A solution containing 0.99 g (2.84 mmol) of late eluting fraction from the ChiralPak OJ column and 15 mL of DCM was treated with 1.5 mL of TFA. The reaction mixture was allowed to stir overnight. An additional 1.0 mL of TFA was added and the reaction mixture was allowed to stir for an additional 5 h. The solvents were removed under reduced pressure and the residue was partitioned between aqueous KOH and ethyl acetate. The water layer was further extracted with DCM and the combined organic layers were dried over MgSO$_4$ and filtered. The solvents were removed under reduced pressure to give 650 mg (92%) of (R)-4-(4-fluorophenyl)-2,8-diazaspiro[4.5]decan-1-one as a tan foamy solid: LCMS m/z: 249.2 (M+H)$^+$, [α]$^D$+1.67 (c=1.01, MeOH).

e. Step E: tert-Butyl (S)-1-((R)-4-(4-fluorophenyl)-1-oxo-2,8-diazaspiro[4.5]decan-8-yl)propan-2-ylcarbamate

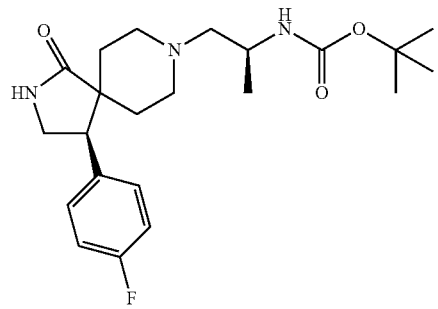 [SMILES: C[C@@H](CN1CCC2(CC1)C(=O)NC[C@@H]2c1ccc(F)cc1)NC(=O)OC(C)(C)C]

A reaction mixture containing 0.25 g (1.0 mmol) of (R)-4-(4-fluorophenyl)-2,8-diazaspiro[4.5]decan-1-one, 0.25 g (1.44 mmol) of the (S)-tert-butyl 1-oxopropan-2-ylcarbamate, 2 mL of THF, 1 mL of DCM, and 1 g (2.5 mmol) of MP-sodium triacetoxyborohydride resin was rotated overnight. The reaction mixture was filtered and the solvents were removed under reduced pressure. The residue was subjected to silica gel chromatography to give 250 mg (61%) of tert-butyl (S)-1-((R)-4-(4-fluorophenyl)-1-oxo-2,8-diazaspiro[4.5]decan-8-yl)propan-2-ylcarbamate as a colorless oil.

1HNMR (400 MHz, CD$_3$OD) δ ppm 7.35-7.31 (m, 2H), 7.10-7.06 (m, 2H), 3.85 (brs, 1H), 3.73-3.68 (m, 1H), 3.55-3.51 (m, 2H), 3.39-3.27 (m, 1H), 3.10-2.87 (m, 2H), 2.78-2.59 (m, 3H), 2.01-1.72 (m, 5H), 1.42 (s, 9H), 1.32-1.20 (m, 1H), and 1.11 (d, 3H, J=2.4 Hz); LCMS m/z: 406.2 (M+H)$^+$.

f. Step F: (R)-8-((S)-2-aminopropyl)-4-(4-fluorophenyl)-2,8-diazaspiro[4.5]decan-1-one bis 2,2,2-trifluoroacetate

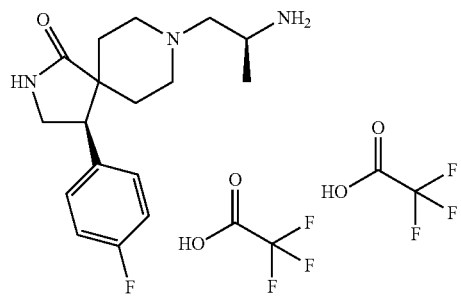

To a solution containing 250 mg (0.62 mmol) of tert-butyl (S)-1-((R)-4-(4-fluorophenyl)-1-oxo-2,8-diazaspiro[4.5]decan-8-yl)propan-2-ylcarbamate and 5 mL of DCM was added ~1 mL of TFA. The reaction mixture was allowed to stir at room temperature overnight. Solvents were removed under reduced pressure and the residue was used without further purification. LCMS m/z: 306.2 (M+H)$^+$.

g. Step G: N—((S)-1-((R)-4-(4-Fluorophenyl)-1-oxo-2,8-diazaspiro[4.5]decan-8-yl)propan-2-yl)-3-phenylpropiolamide 2,2,2-trifluoroacetate

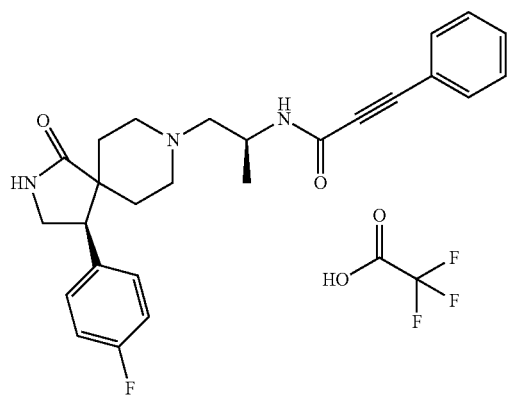 [SMILES: C[C@@H](CN1CCC2(CC1)C(=O)NC[C@@H]2c1ccc(F)cc1)NC(=O)C#Cc1ccccc1 ; O=C(O)C(F)(F)F]

Using general method A, 10 mg of N—((S)-1-((R)-4-(4-fluorophenyl)-1-oxo-2,8-diazaspiro[4.5]decan-8-yl)propan-2-yl)-3-phenylpropiolamide 2,2,2-trifluoroacetate was produced from 16 mg (0.11 mmol) of 3-phenylpropiolic acid and 53 mg (0.1 mmol) of (R)-8-((S)-2-aminopropyl)-4-(4-fluorophenyl)-2,8-diazaspiro[4.5]decan-1-one bis 2,2,2-trifluoroacetate: 1HNMR (400 MHz, CD$_3$OD) δ ppm 7.58 (m, 2H), 7.49-7.46 (m, 1H), 7.44-7.7.40 (m, 2H), 7.35 (brm, 2H), 7.15-7.09 (m, 2H), 4.45 (brs, 1H), 3.99-3.40 (m, 6H), 3.27-3.10 (m, 2H), 2.21-1.85 (m, 3H), 1.49-1.32 (m, 2H), and 1.25 (d, 3H), J=6.8 Hz); LCMS m/z: 434.3 (M+H)$^+$.

4. Example 2

(S)-4-fluoro-N-(2-(4-(4-fluorophenyl)-1-oxo-2,8-diazaspiro[4.5]decan-8-yl)ethyl)benzamide 2,2,2-trifluoroacetate a. Step A: (S)-4-(4-Fluorophenyl)-2,8-diazaspiro[4.5]decan-1-one

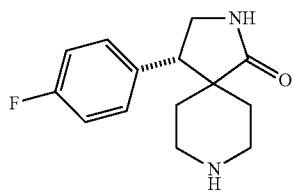 [SMILES: O=C1NC[C@@H](c2ccc(F)cc2)C12CCNCC2]

A solution containing 0.99 g (2.84 mmol) of early eluting fraction from the ChiralPak OJ column and 15 mL of DCM was treated with 1.5 mL of TFA. The reaction mixture was allowed to stir overnight. An additional 1.0 mL of TFA was added and the reaction mixture was allowed to stir for an additional 5 h. The solvents were removed under reduced pressure and the residue was partitioned between aqueous KOH and EtOAc. The water layer was further extracted with DCM and the combined organic layers were dried over MgSO$_4$ and filtered. The solvents were removed under reduced pressure to give 611 mg (85%) of (S)-4-(4-fluorophenyl)-2,8-diazaspiro[4.5]decan-1-one as a tan foamy solid: LCMS m/z: 249.2 [M+H]$^+$, [α]$_D$–3.3 (c=1.00, MeOH).

b. Step B: (S)-tert-Butyl 2-(4-(4-fluorophenyl)-1-oxo-2,8-diazaspiro[4.5]decan-8-yl)ethylcarbamate

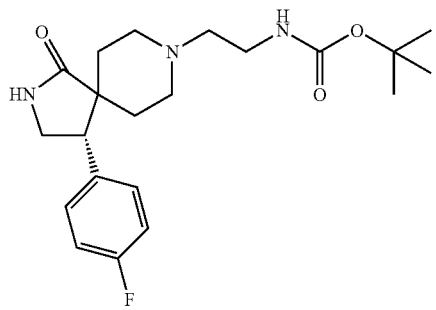 [SMILES: CC(C)(C)OC(=O)NCCN1CCC2(CC1)C(=O)NC[C@H]2c1ccc(F)cc1]

A mixture containing 0.25 g (1.0 mmol) of (S)-4-(4-fluorophenyl)-2,8-diazaspiro[4.5]decan-1-one, 0.2 g (1.41 mmol) of tert-butyl 2-oxoethylcarbamate, 2 mL of THF, 1 mL of DCM, and 1 g (2.5 mmol) of MP-sodium triacetoxyborohydride resin was rotated overnight. The reaction mixture was filtered and the solvents were removed under reduced pressure. The residue was subjected to silica gel chromatography to give 131 mg (33%) of (S)-tert-butyl 2-(4-(4-fluorophenyl)-1-oxo-2,8-diazaspiro[4.5]decan-8-yl)ethylcarbamate as a colorless oil: 1HNMR (400 MHz, CD$_3$OD) δ ppm 7.35-7.32 (m, 2H), 7.12-7.07 (m, 2H), 3.68 (dd, 1H, J=10.4 and 7.6 Hz), 3.57 (dd, 1H, J=10.4 and 6.4 Hz), 3.32-3.28 (m, 3H), 3.11-3.08 (m, 2H), 2.87-2.84 (m, 3H), 2.02-1.80 (m, 4H), 1.41 (s, 9H), and 1.34-1.27 (m, 2H); LCMS m/z: 392.3 (M+H)$^+$.

C. Step C: (S)-8-(2-Aminoethyl)-4-(4-fluorophenyl)-2,8-diazaspiro[4.5]decan-1-one bis(2,2,2-trifluoroacetate)

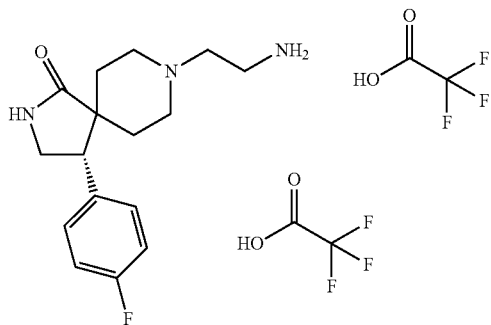 [SMILES: NCCN1CCC2(CC1)C(=O)NC[C@H]2c1ccc(F)cc1 ; O=C(O)C(F)(F)F ; O=C(O)C(F)(F)F]

To a solution containing 130 mg (0.33 mmol) of (S)-tert-butyl 2-(4-(4-fluorophenyl)-1-oxo-2,8-diazaspiro[4.5]decan-8-yl)ethylcarbamate and 5 mL of DCM was added 1 mL of TFA. The reaction mixture was allowed to stir at room temperature overnight. The solvents were removed under reduced pressure and the residue was used without further purification: LCMS m/z: 292.2 (M+H)$^+$.

d. Step D: (S)-4-Fluoro-N-(2-(4-(4-fluorophenyl)-1-oxo-2,8-diazaspiro[4.5]decan-8-yl)ethyl)benzamide 2,2,2-trifluoroacetate

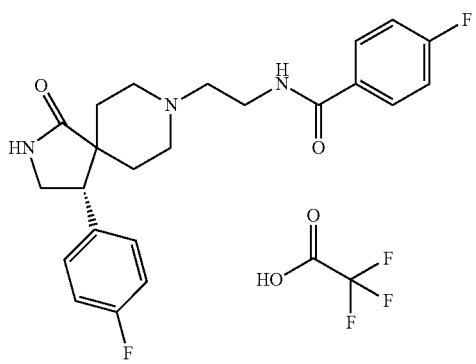 [SMILES: O=C(NCCN1CCC2(CC1)C(=O)NC[C@H]2c1ccc(F)cc1)c1ccc(F)cc1 ; O=C(O)C(F)(F)F]

Using General Method A, 12 mg of a rotameric mixture of (S)-4-fluoro-N-(2-(4-(4-fluorophenyl)-1-oxo-2,8-diazaspiro[4.5]decan-8-yl)ethyl)benzamide 2,2,2-trifluoroacetate 4-fluorobenzoic acid was produced from 52 mg (S)-8-(2-aminoethyl)-4-(4-fluorophenyl)-2,8-diazaspiro[4.5]decan-1-one bis(2,2,2-trifluoroacetate) and 15 mg of 4-fluorobenzoic acid: 1HNMR (400 MHz, CD$_3$OD) δ ppm 8.09-8.05 (m, 0.5H), 7.88 (dd, 1.5H, J=8.8 and 5.6 Hz), 7.38-7.35 (m, 1.5H), 7.23-7.17 (m, 2.5H), 7.14-7.10 (m, 2H), 3.88-3.84 (m, 1H), 3.72-3.48 (m, 8H), 3.37-3.30 (m, 4H), 2.25 (brm, 1H), 2.05-1.94 (m, 2H), and 1.44-1.37 (m, 1H); LCMS m/z: 414.2 (M+H)$^+$.

5. Example 3

(S)—N-(2-(4-(4-Fluorophenyl)-1-oxo-2,8-diazaspiro[4.5]decan-8-yl)ethyl)-2-naphthamide 2,2,2-trifluoroacetate

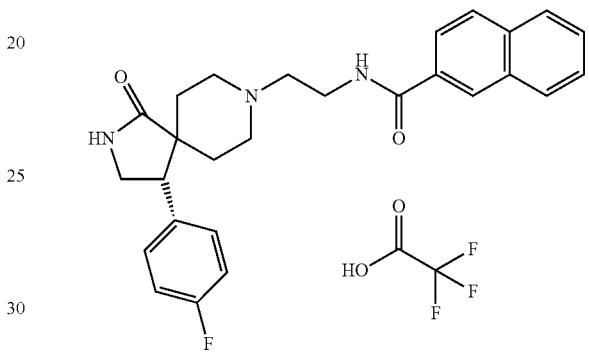

Using General Procedure B, 9 mg of (S)—N-(2-(4-(4-fluorophenyl)-1-oxo-2,8-diazaspiro[4.5]decan-8-yl)ethyl)-2-naphthamide 2,2,2-trifluoroacetate was produced from 52 mg (S)-8-(2-aminoethyl)-4-(4-fluorophenyl)-2,8-diazaspiro[4.5]decan-1-one bis(2,2,2-trifluoroacetate) and 21 mg of 2-naphthoyl chloride: 1HNMR (400 MHz, CD$_3$OD) δ ppm 8.39 (s, 1H), 7.99-7.87 (m, 4H), 7.63-7.58 (m, 2H), 7.37 (brm, 2H), 7.12 (m, 2H), 3.94-3.87 (m, 1H), 3.79-3.45 (m, 8H), 3.38-3.35 (m, 4H), 2.24-2.10 (m, 1H), 2.08-1.89 (m, 2H), and 1.45-1.32 (m, 1H); LCMS m/z: 446.2 (M+H)$^+$.

Various compounds prepared according to the disclosed methods are shown in Table 2, below, with characterizing data.

TABLE 2

COMPOUND CHARACTERIZATION

| Example | Structure | Nomenclature | LCMS m/z [M + H]$^+$ |
|---|---|---|---|
| 4 (NGH) | 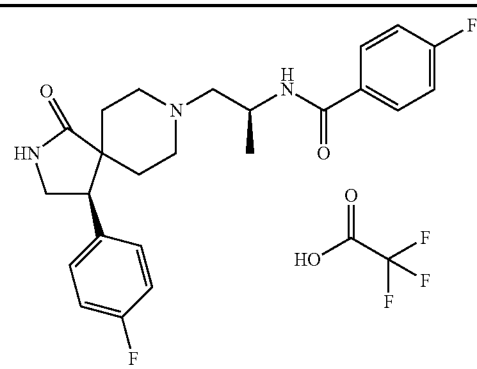 | 4-fluoro-N-((S)-1-((R)-4-(4-fluorophenyl)-1-oxo-2,8-diazaspiro[4.5]decan-8-yl)propan-2-yl)benzamide 2,2,2-trifluoroacetate | 428.2 |

TABLE 2-continued

COMPOUND CHARACTERIZATION

| Example | Structure | Nomenclature | LCMS m/z [M + H]+ |
|---|---|---|---|
| 5 (POA) | 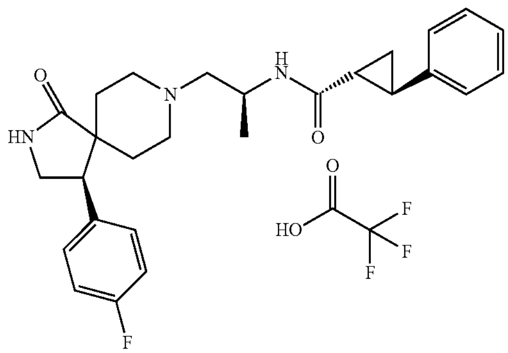 | trans-N-((S)-1-((R)-4-(4-fluorophenyl)-1-oxo-2,8-diazaspiro[4.5]decan-8-yl)propan-2-yl)-2-phenylcyclopropane-carboxamide 2,2,2-trifluoroacetate | 450.3 |
| 6 (PIG) | 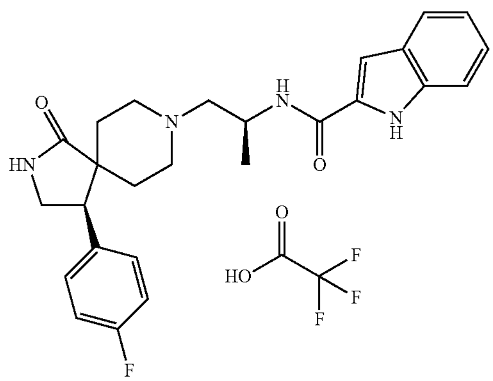 | N-((S)-1-((R)-4-(4-fluorophenyl)-1-oxo-2,8-diazaspiro[4.5]decan-8-yl)propan-2-yl)-1H-indole-2-carboxamide 2,2,2-trifluoroacetate | 449.3 |
| 7 (P0L) | 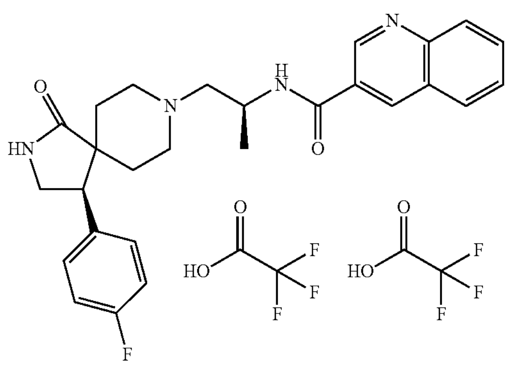 | N-((S)-1-((R)-4-(4-fluorophenyl)-1-oxo-2,8-diazaspiro[4.5]decan-8-yl)propan-2-yl)quinoline-3-carboxamide bis(2,2,2-trifluoroacetate) | 461.3 |
| 8 (P0Q) | 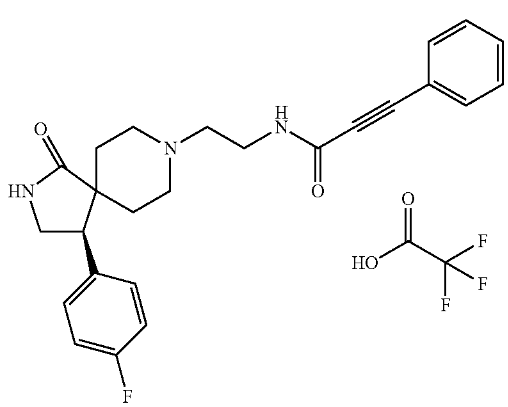 [SMILES: O=C(C#Cc1ccccc1)NCCN1CCC2(CC1)C(=O)NC[C@@H]2c1ccc(F)cc1 ; O=C(O)C(F)(F)F] | (R)-N-(2-(4-(4-fluorophenyl)-1-oxo-2,8-diazaspiro[4.5]decan-8-yl)ethyl)-3-phenylpropiolamide 2,2,2-trifluoroacetate | 420.2 |

TABLE 2-continued

COMPOUND CHARACTERIZATION

| Example | Structure | Nomenclature | LCMS m/z [M + H]+ |
|---|---|---|---|
| 9 (NFW) | 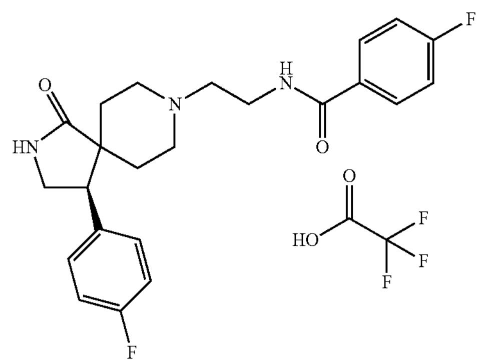 | (R)-4-fluoro-N-(2-(4-(4-fluorophenyl)-1-oxo-2,8-diazaspiro[4.5]decan-8-yl)ethyl)benzamide 2,2,2-trifluoroacetate | 414.2 |
| 10 (P1E) | 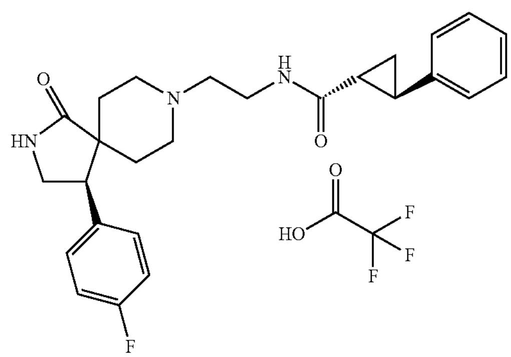 | trans-N-(2-((R)-4-(4-fluorophenyl)-1-oxo-2,8-diazaspiro[4.5]decan-8-yl)ethyl)-2-phenylcyclopropane-carboxamide 2,2,2-trifluoroacetate | 436.2 |
| 11 (P23) | 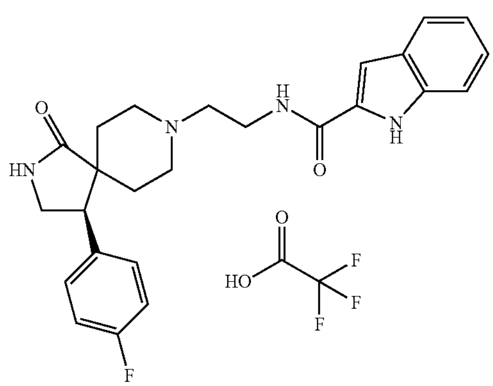 [SMILES: O=C(NCCN1CCC2(CC1)C(=O)NC[C@@H]2c1ccc(F)cc1)c1cc2ccccc2[nH]1 ; O=C(O)C(F)(F)F] | (R)-N-(2-(4-(4-fluorophenyl)-1-oxo-2,8-diazaspiro[4.5]decan-8-yl)ethyl)-1H-indole-2-carboxamide 2,2,2-trifluoroacetate | 435.2 |
| 12 (P1P) | 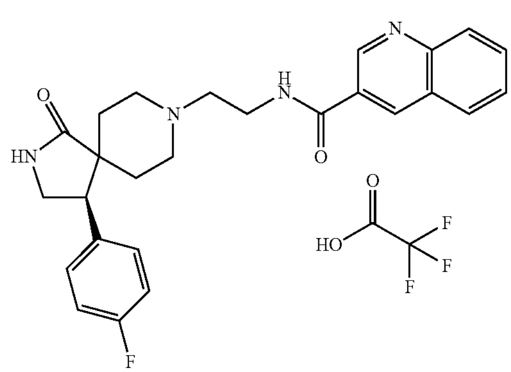 | (R)-N-(2-(4-(4-fluorophenyl)-1-oxo-2,8-diazaspiro[4.5]decan-8-yl)ethyl)quinoline-3-carboxamide bis(2,2,2-trifluoroacetate) | 447.3 |

TABLE 2-continued

COMPOUND CHARACTERIZATION

| Example | Structure | Nomenclature | LCMS m/z [M + H]+ |
|---|---|---|---|
| 13 (NJ5) | 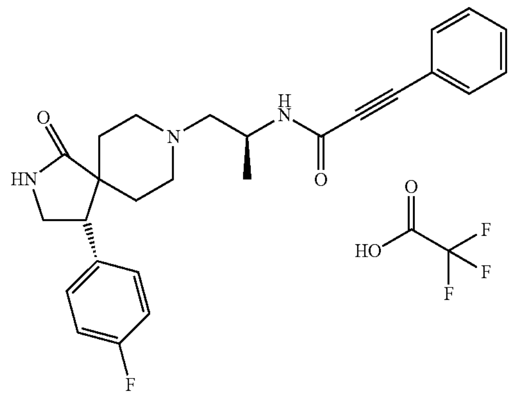 | N-((S)-1-((S)-4-(4-fluorophenyl)-1-oxo-2,8-diazaspiro[4.5]decan-8-yl)propan-2-yl)-3-phenylpropiolamide 2,2,2-trifluoroacetate | 434.2 |
| 14 (P2B) | 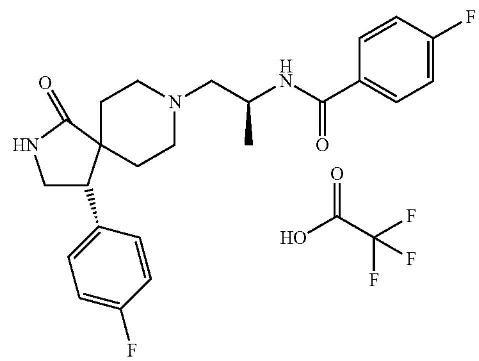 | 4-fluoro-N-((S)-1-((S)-4-(4-fluorophenyl)-1-oxo-2,8-diazaspiro[4.5]decan-8-yl)propan-2-yl)benzamide 2,2,2-trifluoroacetate | 428.3 |
| 15 (NGQ) | 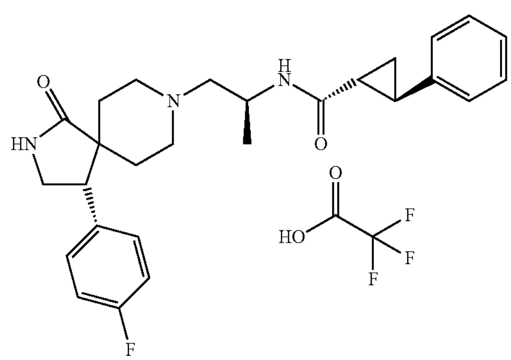 | trans-N-((S)-1-((S)-4-(4-fluorophenyl)-1-oxo-2,8-diazaspiro[4.5]decan-8-yl)propan-2-yl)-2-phenylcyclopropane-carboxamide 2,2,2-trifluoroacetate | 450.3 |
| 16 (NG3) | 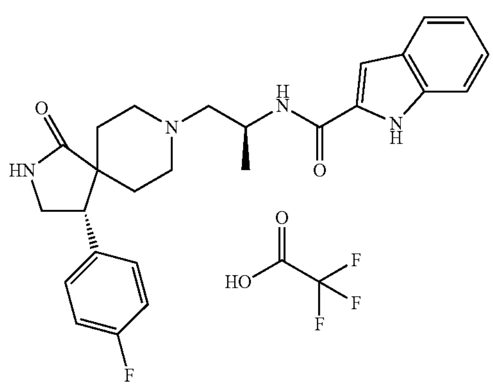 | N-((S)-1-((S)-4-(4-fluorophenyl)-1-oxo-2,8-diazaspiro[4.5]decan-8-yl)propan-2-yl)-1H-indole-2-carboxamide 2,2,2-trifluoroacetate | 449.3 |

TABLE 2-continued

COMPOUND CHARACTERIZATION

| Example | Structure | Nomenclature | LCMS m/z [M + H]+ |
|---|---|---|---|
| 17 (P2E) | 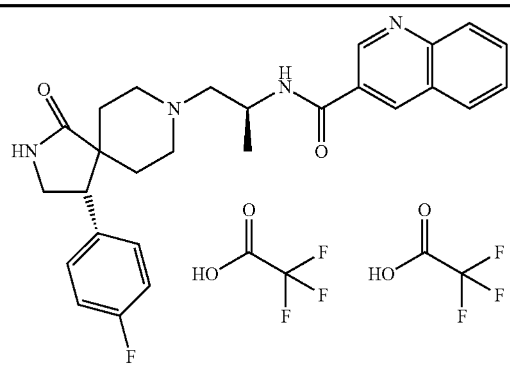 | N-((S)-1-((S)-4-(4-fluorophenyl)-1-oxo-2,8-diazaspiro[4.5]decan-8-yl)propan-2-yl)quinoline-3-carboxamide bis(2,2,2-trifluoroacetate) | 461.3 |
| 18 (NFT) | 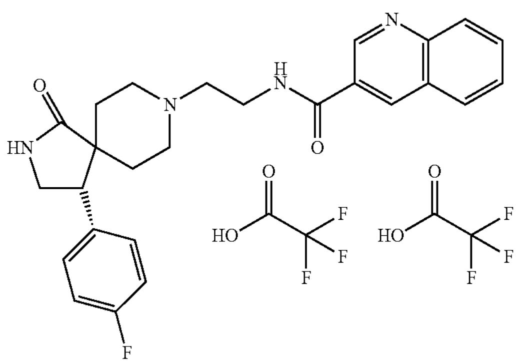 | (S)-N-(2-(4-(4-fluorophenyl)-1-oxo-2,8-diazaspiro[4.5]decan-8-yl)ethyl)quinoline-3-carboxamide bis(2,2,2-trifluoroacetate) | 447.2 |
| 19 (P22) | 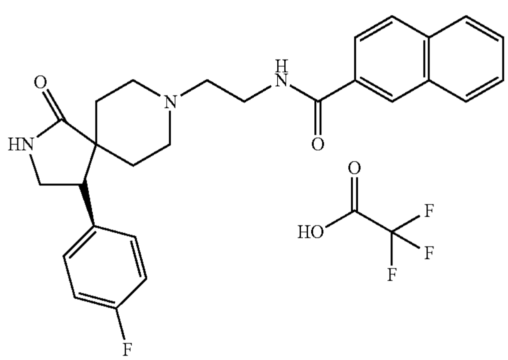 | (S)-N-(2-(4-(4-fluorophenyl)-1-oxo-2,8-diazaspiro[4.5]decan-8-yl)ethyl)-2-naphthamide 2,2,2-trifluoroacetate | 446.3 |
| 20 (P1Q) | 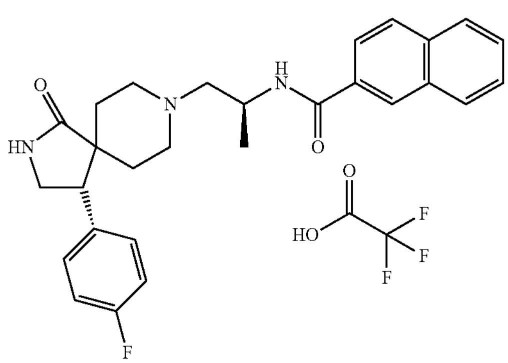 | N-((S)-1-((S)-4-(4-fluorophenyl)-1-oxo-2,8-diazaspiro[4.5]decan-8-yl)propan-2-yl)-2-naphthamide 2,2,2-trifluoroacetate | 460.3 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound comprising a structure represented by a formula:

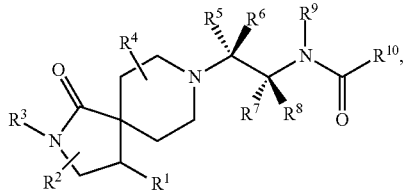

wherein each ----- independently comprises an optional covalent bond;
wherein $R^1$ is an optionally substituted C3 to C9 organic residue selected from aryl, heteroaryl, cycloalkyl, heterocycloalkyl, cycloalkenyl, and heterocycloalkenyl;
wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue;
wherein $R^3$ comprises hydrogen, an optionally substituted C1 to C6 alkyl, an optionally substituted C3 to C6 cycloalkyl, or a hydrolysable residue;
wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue;
wherein each of $R^5$ and $R^6$ independently comprises hydrogen, halide, hydroxyl, trifluoromethyl, amino, cyano, nitro, azide, carboxamido, alkoxy, thiol, alkylsulfonyl, or an optionally substituted C1 to C6 alkyl;
wherein each of $R^7$ and $R^8$ independently comprises hydrogen, halide, hydroxyl, trifluoromethyl, amino, cyano, nitro, azide, carboxamido, alkoxy, thiol, alkylsulfonyl, or an optionally substituted C1 to C6 alkyl;
wherein $R^9$ comprises hydrogen, an optionally substituted C1 to C6 alkyl, an optionally substituted C3 to C6 cycloalkyl, or a hydrolysable residue;
wherein $R^{10}$ comprises an optionally substituted C1 to C12 organic residue selected from alkyl, aryl, heteroaryl, cycloalkyl, heterocycloalkyl, cycloalkenyl, and heterocycloalkenyl,
or a pharmaceutically acceptable salt thereof.

2. The compound of claim 1, wherein $R^1$ is optionally substituted aryl selected from phenyl and naphthyl.

3. The compound of claim 1, wherein $R^8$ is hydrogen.

4. The compound of claim 1, wherein $R^8$ is selected from halide, hydroxyl, trifluoromethyl, amino, cyano, nitro, azide, carboxamido, alkoxy, thiol, alkylsulfonyl, and an optionally substituted C1 to C6 organic residue.

5. The compound of claim 1, wherein $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

6. The compound of claim 1, wherein $R^8$ is methyl.

7. The compound of claim 1, wherein $R^7$ is hydrogen and wherein $R^8$ is selected from halide, hydroxyl, trifluoromethyl, amino, cyano, nitro, azide, carboxamido, alkoxy, thiol, alkylsulfonyl, and an optionally substituted C1 to C6 organic residue.

8. The compound of claim 1, wherein $R^7$ is hydrogen and wherein $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

9. The compound of claim 1, wherein $R^{10}$ is an optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

10. The compound of claim 1, having a structure represented by a formula:

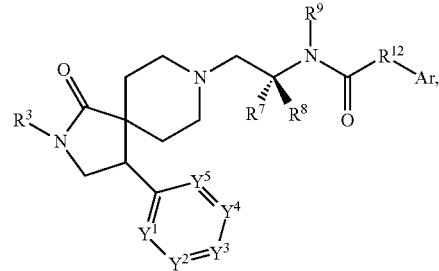

wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl;
wherein each of $Y^1$, $Y^2$, $Y^3$, $Y^4$, and $Y^5$ independently comprises N or C—$R^{11}$, wherein each $R^{11}$ independently comprises hydrogen, halide, hydroxyl, trifluoromethyl, amino, cyano, nitro, azide, carboxamido, alkoxy, thiol, alkylsulfonyl, or an optionally substituted C1 to C6 organic residue;
wherein $R^{12}$ is a covalent bond, a C1 to C3 alkyl, or a C1 to C3 cycloalkyl; and
wherein Ar is an optionally substituted C4 to C10 organic residue selected from aryl and heteroaryl.

11. The compound of claim 10, wherein no more than two of $Y^1$, $Y^2$, $Y^3$, $Y^4$, and $Y^5$ are N.

12. The compound of claim 10, wherein Ar is phenyl, indolyl, quinolinyl, naphthyl, or fluorophenyl.

13. The compound of claim 10, wherein $R^{12}$ has a structure:

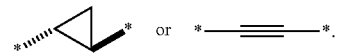

14. A method for preparing a compound comprising the steps of:
a. providing a compound having a structure:

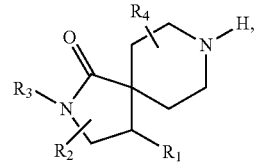

wherein $R^1$ is an optionally substituted C3 to C9 organic residue selected from aryl, heteroaryl, cycloalkyl, heterocycloalkyl, cycloalkenyl, and heterocycloalkenyl;
wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue;

wherein $R^3$ comprises hydrogen, an optionally substituted C1 to C6 alkyl, an optionally substituted C3 to C6 cycloalkyl, or a hydrolysable residue; and wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue, and b. reacting with a compound having a structure:

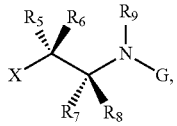

wherein each of $R^5$ and $R^6$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl;

wherein each of $R^7$ and $R^8$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl;

wherein $R^9$ comprises hydrogen, an optionally substituted C1 to C6 alkyl, an optionally substituted C3 to C6 cycloalkyl, or a hydrolysable residue, wherein G is a protecting group, and wherein X is a leaving group.

15. The method of claim 14, wherein providing is chiral separation.

16. The method of claim 14, further comprising the step of reacting with a compound having a structure:

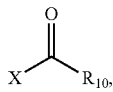

wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, and wherein X is a leaving group.

17. A method for the treatment of cancer in a mammal comprising the step of administering to the mammal at least one compound having a structure represented by the formula:

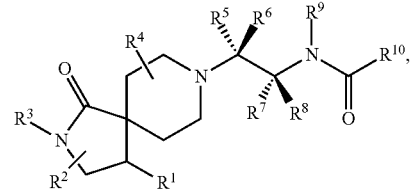

wherein each ----- independently comprises an optional covalent bond;

wherein $R^1$ is an optionally substituted C3 to C9 organic residue selected from aryl, heteroaryl, cycloalkyl, heterocycloalkyl, cycloalkenyl, and heterocycloalkenyl;

wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue;

wherein $R^3$ comprises hydrogen, an optionally substituted C1 to C6 alkyl, an optionally substituted C3 to C6 cycloalkyl, or a hydrolysable residue;

wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue;

wherein each of $R^5$ and $R^6$ independently comprises hydrogen, halide, hydroxyl, trifluoromethyl, amino, cyano, nitro, azide, carboxamido, alkoxy, thiol, alkylsulfonyl, or an optionally substituted C1 to C6 alkyl;

wherein each of $R^7$ and $R^8$ independently comprises hydrogen, halide, hydroxyl, trifluoromethyl, amino, cyano, nitro, azide, carboxamido, alkoxy, thiol, alkylsulfonyl, or an optionally substituted C1 to C6 alkyl;

wherein $R^9$ comprises hydrogen, an optionally substituted C1 to C6 alkyl, an optionally substituted C3 to C6 cycloalkyl, or a hydrolysable residue;

wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt thereof.

18. The method of claim 17, wherein the mammal is a human.

19. The method of claim 17, wherein the method further comprises the step of identifying a mammal in need of treatment of the disorder.

20. The method of claim 17, wherein the cancer is selected from breast cancer, renal cancer, gastric cancer, colorectal cancer, lymphoma, cancers of the brain, genitourinary tract cancer, lymphatic system cancer, stomach cancer, larynx cancer, lung cancer, pancreatic cancer, and malignant melanoma.

* * * * *